United States Patent [19]
Allen et al.

[11] Patent Number: 5,240,928
[45] Date of Patent: Aug. 31, 1993

[54] SUBSTITUTED QUINAZOLINONES AS ANGIOTENSIN II ANTAGONISTS

[75] Inventors: Eric E. Allen, Edison; Stephen E. de Laszlo, Atlantic Highlands; Prasun K. Chakravarty, Edison; William J. Greenlee, Teaneck; Arthur A. Patchett; Thomas F. Walsh, both of Westfield, all of N.J.

[73] Assignee: Merck & Co., Inc., Rahway, N.J.

[21] Appl. No.: 665,518

[22] Filed: Mar. 6, 1991

Related U.S. Application Data

[63] Continuation-in-part of Ser. No. 537,891, Jun. 18, 1990, abandoned, which is a continuation-in-part of Ser. No. 527,630, May 23, 1990, abandoned, which is a continuation-in-part of Ser. No. 375,217, Jul. 3, 1989, abandoned.

[51] Int. Cl.$^5$ .................. A61K 31/505; A01N 43/54; C07D 239/90; C07D 239/91
[52] U.S. Cl. .................. 514/259; 514/260; 544/284; 544/287; 544/289
[58] Field of Search ............... 514/259, 260; 544/287, 544/284, 289

[56] References Cited

U.S. PATENT DOCUMENTS

| | | | |
|---|---|---|---|
| 3,936,453 | 2/1976 | Hardtmann | 260/256.4 |
| 4,880,804 | 11/1989 | Carini et al. | 514/234.5 |

FOREIGN PATENT DOCUMENTS

| | | |
|---|---|---|
| 58696/90 | 1/1991 | Australia . |
| 253310 | 1/1988 | European Pat. Off. . |
| 407342 | 1/1991 | European Pat. Off. . |
| 411766 | 2/1991 | European Pat. Off. . |
| 419048 | 3/1991 | European Pat. Off. . |

OTHER PUBLICATIONS

Chiu et al, "Non-Peptide Angiotensin II Receptor Antagonists . . . " European Journal of Pharmacology 157(1988) 13-21.

Wong et al., European Journal of Pharmacology, 202, pp. 323-330 (1991).

*Primary Examiner*—Mukund J. Shah
*Assistant Examiner*—Matthew V. Grumbling
*Attorney, Agent, or Firm*—Robert J. North; Joseph F. DiPrima

[57] ABSTRACT

Novel substituted quinazolinones of the formula (I), which are useful as angiotensin II antagonists, are disclosed.

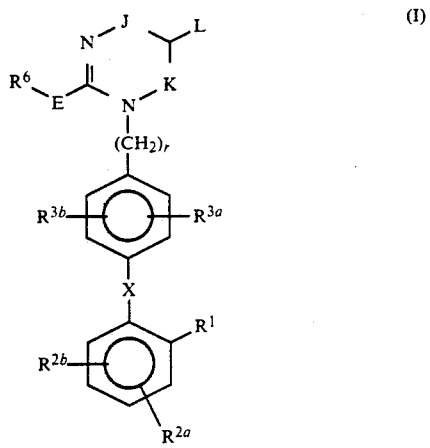

14 Claims, No Drawings

SUBSTITUTED QUINAZOLINONES AS ANGIOTENSIN II ANTAGONISTS

INTRODUCTION OF THE INVENTION

This is a continuation-in-part of copending application Ser. No. 537,891, filed Jun. 18, 1990, now abandoned, which is a continuation-in-part of application Ser. No. 527,630, filed May 23, 1990 now abandoned, which is a continuation-in-part of now abandoned application Ser. No. 375,217 filed Jul. 3, 1989.

This invention relates to novel substituted quinazolinone compounds and derivatives thereof which are useful as angiotensin II antagonists in the treatment of elevated blood pressure and congestive heart failure. Thus, the substituted quinazolinone compounds of the invention are useful as antihypertensives and elavated intraocular pressure.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of AII are known to inhibit the effect of this hormone by competitively blocking the receptors, but their experimental and clinical applications have been limited by their partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyl, Vol. 5, pp. 246-271, Elsevier Science Publisher, Amsterdam, The Netherlands, 1984].

Recently, several non-peptide compounds have been described as AII antagonists. Illustrative of such compounds are those disclosed in U.S. Pat. Nos. 4,207,324; 4,340,598; 4,576,958; 4,582,847 and 4,880,804 in European Patent Applications 028,834; 245,637; 253,310; and 291,969; and in articles by A. T. Chiu, et al. [*Eur. J. Pharm. Exp. Therap*, 157, 13-21 (1988)] and by P. C. Wong, et al. [*J. Pharm. Exp. Therap*, 247, 1–7(1988), *Hypertension*, 13, 489–497 (1989)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

DETAILED DESCRIPTION OF THE INVENTION

This invention relates to novel substituted quinazolinone compounds and derivatives thereof which are useful as angiotensin II antagonists, as antihypertensives, in the treatment of congestive heart failure and in the treatment of elevated intraocular pressure. The compounds of this invention have the general formula (I):

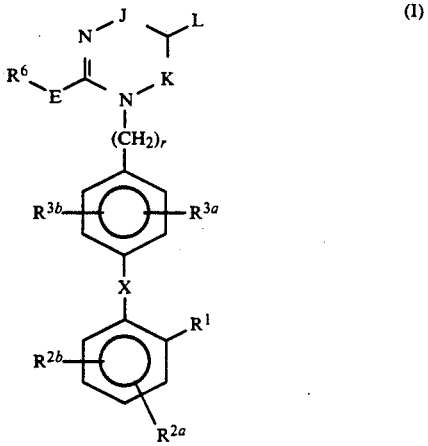

wherein:

L is connected with J or K to form an aromatic ring as defined below;

J is —C(=M)— or J and L are connected together to form a 6 carbon aromatic ring substituted with $R^{7a}$, $R^{7b}$, $R^{8a}$ and $R^{8b}$, provided that only one of J and K is —C(=M)—;

K is —C(=M)— or K and L are connected together to form a 6 carbon aromatic ring substituted with $R^{7a}$, $R^{7b}$, $R^{8a}$ and $R^{8b}$, provided that only one of J and K is —C(=M)—;

M is O or $NR^{22}$;

$R^1$ is
(a) —$CO_2R^4$,
(b) —$SO_3R^5$,
(c) —$NHSO_2R^{23}$,
(d) —$PO(OR^5)_2$,
(e) —$SO_2$—NH—$R^{23}$,

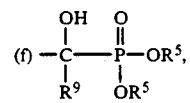

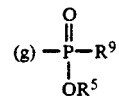

(h) —$SO_2NH$—CO—$R^{23}$,
(i) —$CH_2SO_2NH$—CO—$R^{23}$,
(j) —CONH—$SO_2R^{23}$,
(k) —$CH_2CONH$—$SO_2R^{23}$,
(l) —$NHSO_2NHCO$—$R^{23}$,
(m) —$NHCONHSO_2$—$R^{23}$,

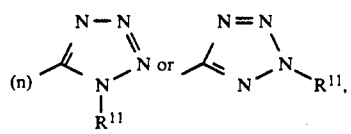

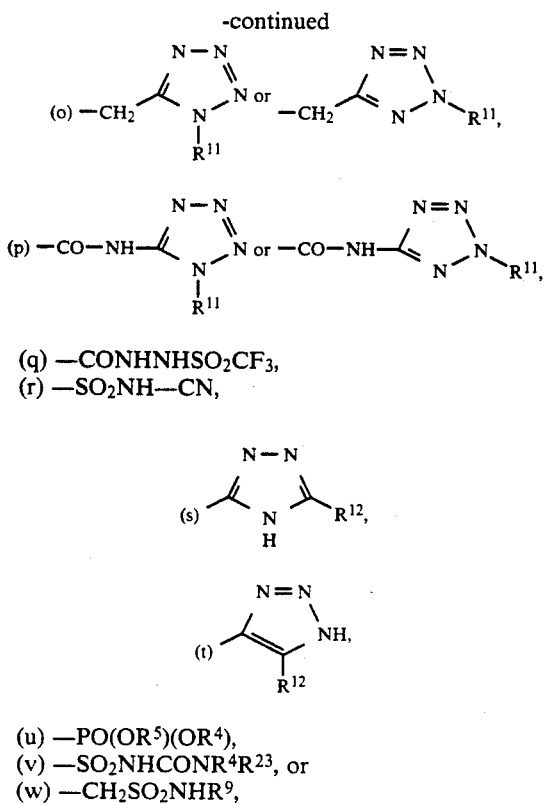

(q) —CONHNHSO₂CF₃,
(r) —SO₂NH—CN, (u) —PO(OR⁵)(OR⁴),
(v) —SO₂NHCONR⁴R²³, or
(w) —CH₂SO₂NHR⁹, wherein heteroaryl is an unsubstituted, monosubstituted or disubstituted five or six membered aromatic ring which can optionally contain from 1 to 3 heteroatoms selected from the group consisting of O, N or S and wherein the substituents are members selected from the group consisting of —OH, —SH, —C₁-C₄-alkyl, —C-1-C₄-alkoxy, —CF₃, halo (Cl, Br, F, I), —NO₂, —CO₂H, —CO₂—(C₁-C₄-alkyl), —NH₂, —NH(-C₁-C₄-alkyl) and —N(C₁-C₄-alkyl)₂;

R²ᵃ and R²ᵇ are each independently
(a) H,
(b) halogen, (Cl, Br, I, F),
(c) NO₂,
(d) NH₂,
(e) C₁-C₄-alkylamino,
(f) di(C₁-C₄-alkyl)amino,
(g) SO₂NHR⁹,
(h) CF₃,
(i) C₁-C₆-alkyl,
(j) C₁-C₆-alkoxy,
(k) C₁-C₆-alkyl-S-,
(l) C₂-C₆-alkenyl,
(m) C₂-C₆-alkynyl;
(n) aryl as defined below,
(o) aryl (C₁-C₄-alkyl), or
(p) C₃-C₇-cycloalkyl;

R³ᵃ is
(a) H,
(b) halogen (Cl, Br, I, F),
(c) C₁-C₆-alkyl,
(d) C₁-C₆-alkoxy, or
(e) C₁-C₆-alkoxyalkyl;

R³ᵇ is
(a) H,
(b) halogen (Cl, Br, I, F),
(c) NO₂,
(d) C₁-C₆-alkyl,
(e) C₁-C₆-acyloxy, or
(f) C₃-C₇-cycloalkyl,
(g) C₁-C₆-alkoxy,
(h) —NHSO₂R⁴,
(i) hydroxy(C₁-C₄-alkyl),
(j) aryl(C₁-C₄-alkyl),
(k) C₁-C₄-alkylthio,
(l) C₁-C₄-alkyl sulfinyl,
(m) C₁-C₄-alkyl sulfonyl,
(n) NH₂,
(o) C₁-C₄-alkylamino,
(p) di(C₁-C₄-alkyl)amino,
(q) fluoro-C₁-C₄-alkyl-,
(r) —SO₂—NHR⁹,
(s) aryl as defined below,
(t) furyl,
(u) CF₃,
(v) C₂-C₆-alkenyl, or
(w) C₂-C₆-alkynyl;

wherein aryl is phenyl or naphthyl optionally substituted with one or two substituents selected from the group consisting of halogen (Cl, Br, I, F), N(R⁴)₂, CO₂R⁴, C₁-C₄-alkyl, C₁-C₄-alkoxy, NO₂, CF₃, C₁-C₄-alkylthio, or OH;

R⁴ is H, aryl or heteroaryl as defined above or straight chain or branched C₁-C₆ alkyl optionally substituted with aryl as defined above;

R⁴ᵃ is aryl as defined above or straight chain or branched C₁-C₆-alkyl optionally substituted with aryl as defined above $$R^5 \text{ is } H, \ -\overset{R^4}{\underset{|}{CH}}-O-\overset{O}{\underset{\|}{C}}-R^{4a};$$

E is a single bond, —NR¹³(CH₂)ₛ—, —S(O)ₓ(CH₂)ₛ— where x is 0 to 2 and s is 0 to 5, —CH(OH)—, —O—, or CO—;

R⁶ is
(a) aryl as defined above optionally substituted with 1 or 2 substituents selected from the group consisting of halogen (Cl, Br, I, F), —O—C₁-C₄-alkyl, C₁-C₄-alkyl, —NO₂, —CF₃, —SO₂NR⁹R¹⁰, —S—C₁-C₄-alkyl, —OH, —NH₂, C₃-C₇-cycloalkyl, and C₃-C₁₀-alkenyl;
(b) straight chain or branched C₁-C₆-alkyl, C₂-C₅-alkenyl or C₂-C₅-alkynyl each of which can be optionally substituted with a substituent selected from the group consisting of aryl as defined above, C₃-C₇-cycloalkyl, halogen (Cl, Br, I, F), CF₃, CF₂CF₃, —NH₂, —NH(C₁-C₄-alkyl), —OR⁴ —N(C₁-C₄-alkyl)₂, —NH—SO₂R⁴, —COOR⁴, and —SO₂NHR⁹; or
(c) an unsubstituted, monosubstituted or disubstituted heteroaromatic 5 or 6 membered cyclic ring which can contain one or two members selected from the group consisting of N, O, S, and wherein the substituents are members selected from the group consisting of —OH, —SH, C₁-C₄-alkyl, C₁-C₄-alkoxy, —CF₃, halogen (Cl, Br, I, F), or NO₂;
(d) C₃-C₇-cycloalkyl;
(e) perfluoro-C₁-C₄-alkyl, or
(f) H;

R⁷ᵃ and R⁷ᵇ are independently
(a) H,
(b) straight chain or branched C₁-C₆-alkyl, C₂-C₆-alkenyl or C₂-C₆-alkynyl,
(c) halogen (Cl, Br, I, F)

(d) —CF₃, or
(e) when R⁷ᵃ and R⁷ᵇ are bonded to adjacent carbon atoms, they can be joined to form a phenyl ring;

R⁸ᵃ and R⁸ᵇ are independently
(a) H,
(b) C₁–C₆-alkyl optionally substituted with a substituent selected from the group consisting of —OH, -guanidino, C₁–C₄-alkoxy, —N(R⁴)₂, COOR⁴, —CON(R⁴)₂, —O—COR⁴, —aryl, -heteroaryl, —S(O)ₓ—R²³, -tetrazol-5-yl, —CONHSO₂R²³, —SO₂NH-heteroaryl, —SO₂NHCOR²³, —PO(OR⁴)₂, —PO(OR⁴)R⁹, —SO₂NH—CN, —NR¹⁰COOR²³, morpholino, N—(C₁–C₆-alkyl)piperazine, or —COR⁴,
(c) —CO-aryl,
(d) —C₃–C₇-cycloalkyl,
(e) halogen (Cl, Br, I, F),
(f) —OH,
(g) —OR²³,
(h) —C₁–C₄-perfluoroalkyl,
(i) —S(O)ₓ—R²³,
(j) —COOR⁴,
(k) —SO₃H,
(l) —NR⁴R²³,
(m) —NHCOR²³,
(n) —NHCOOR²³,
(o) —SO₂NR⁹R¹⁰,
(p) —NO₂,
(q) —NHSO₂R²³,
(r) —NHCONR⁴R²³,

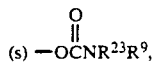
(s) —OCNR²³R⁹, (t) -aryl or -heteroaryl as defined above,
(u) —NHSO₂CF₃,
(v) —SO₂NH-heteroaryl,
(w) —SO₂NHCOR²³,
(x) —CONHSO₂R²³,
(y) —PO(OR⁴)₂,
(z) —PO(OR⁴)R⁹,
(aa) -tetrazol-5-yl,
(bb) —CONH(tetrazol-5-yl),
(cc) —COR⁴,
(dd) —SO²NHCN

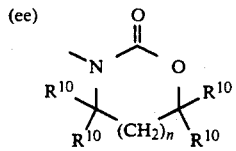
(ee)

where n = 0 or 1, (ff) —CO—heteroraryl, or
(gg) —NHSO₂NR²³R⁹;

R⁹ is H, C₁–C₅-alkyl, aryl or arylmethyl;
R¹⁰ is H, C₁–C₄-alkyl;
R¹¹ is H, C₁–C₆-alkyl, C₁–C₄-alkenyl, C₁–C₄-alkoxy alkyl, or

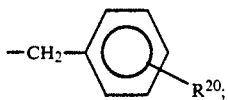

R¹² is —CN, —NO₂, —CF₃ or —CO₂R⁴;
R¹³ is H, (C₁–C₄-alkyl)CO—, C₁–C₆-alkyl, allyl, C₃–C₆-cycloalkyl, aryl or arylmethyl;
R¹⁴ is H, C₁–C₈-alkyl, C₁–C₈-perfluoroalkyl, C₃–C₆-cycloalkyl, aryl or arylmethyl;
R¹⁵ is H, C₁–C₆-alkyl;
R¹⁶ is H, C₁–C₆-alkyl, C₃–C₆-cycloalkyl, aryl or arylmethyl;
R¹⁷ is —NR⁹R¹⁰, —OR¹⁰, —NHCONH₂, —NHCSNH₂,

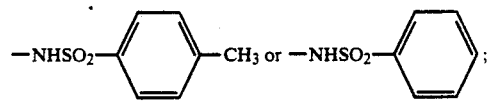

R¹⁸ and R¹⁹ are independently C₁–C₄-alkyl or taken together are —(CH₂)_q— where q is 2 or 3;
R²⁰ is H, —NO₂, —NH₂, —OH or —OCH₃;
R²¹ is H, aryl, or C₁–C₄-alkyl optionally substituted with aryl, —NH₂, —NH(C₁–C₄-alkyl), —N(C₁–C₄-alkyl)₂, —CO₂R⁴, —OH, —SO₃H, or —SO₂NH₂;
R²² is
(a) aryl as defined above,
(b) heteroaryl as defined above, or
(c) C₁–C₄-alkyl optionally substituted with a substituent selected from the group consisting of aryl as defined above, heteroaryl as defined above, —OH, —NH₂, —NH(C₁–C₄-alkyl), —N(C₁–C₄-alkyl)₂, —CO₂R⁴, halogen (Cl, Br, F, I), and —CF₃;
R²³ is
(a) aryl as defined above,
(b) heteroaryl as defined above,
(c) C₃–C₇-cycloalkyl,
(d) C₁–C₆-alkyl optionally substituted with a substituent selected from the group consisting of aryl as defined above, heteroaryl as defined above, —OH, —SH, C₁–C₄-alkyl, —O(C₁–C₄-alkyl), —S(C₁–C₄-alkyl), —CF₃, halogen (Cl, Br, F, I), —NO₂, —CO₂H, CO₂—C₁–C₄-alkyl, —NH₂, —NH(C₁–C₄-alkyl), —N(C₁–C₄-alkyl)₂, —PO₃H₂, —PO(OH)(O—C₁–C₄-alkyl), or —PO(OR⁴)R⁹, or
(e) perfluoro-C₁–C₄-alkyl;

X is
(a) a carbon-carbon single bond,
(b) —CO—,
(c) —O—,
(d) —S—,

(e) —N—, R¹³

(f) —CON—, R¹⁵

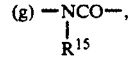
(g) —NCO—, R¹⁵

(h) —OCH₂—,
(i) —CH₂O—,
(j) —SCH₂—,
(k) —CH₂S—,
(l) —NHC(R⁹)(R¹⁰),
(m) —NR⁹SO₂—,
(n) —SO₂NR⁹—,
(o) —C(R⁹)(R¹⁰)NH—, (p) —CH═CH—,
(q) —CF═CF—,
(r) —CH═CF—,
(s) —CF═CH—,
(t) —CH₂CH₂—,
(u) —CF₂CF₂—,

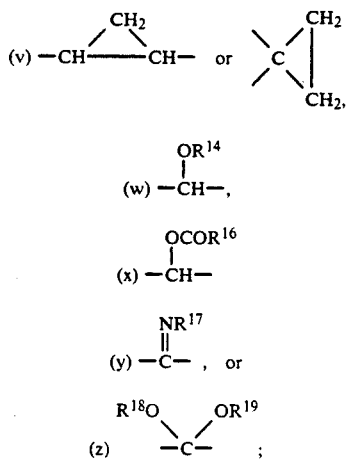

(w) —CH(OR¹⁴)—, (x) —CH(OCOR¹⁶)—

(y) —C(═NR¹⁷)—, or (z) —C(OR¹⁸)(OR¹⁹)—;

r is 1 or 2; and
the pharmaceutically acceptable salts thereof.

One embodiment of the compounds of formula (I) are those compounds wherein:
J is —C(O)—;
K and L are connected together to form a 6 carbon aromatic ring substituted with $R^{7a}$, $R^{7b}$, $R^{8a}$ and $R^{8b}$;
$R^1$ is
(a) —COOH,

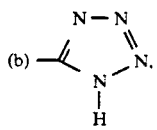

(c) —NH—SO₂R²³;
(d) —SO₂NH-heteroaryl as defined above,
(e) —CH₂SO₂NH-heteroaryl as defined above,
(f) —SO₂NH—CO—R²³,
(g) —CH₂SO₂NH—CO—R²³,
(h) —CONH—SO₂R²³,
(i) —CH₂CONH—SO₂R²³,
(j) —NHSO₂NHCO—R²³, or
(k) —NHCONHSO₂—R²³, $R^{2a}$ is H;
$R^{2b}$ is H, F, Cl, CF₃, C₁-C₆-alkyl, C₂-C₄-alkenyl, or C₂-C₄-alkynyl;
$R^{3a}$ is H;
$R^{3b}$ is H, F, Cl, CF₃, C₁-C₄-alkyl, C₂-C₄-alkenyl, C₂-C₄-alkynyl, C₅-C₆-cycloalkyl, —COOCH₃, —COOC₂H₅, —SO₂—CH₃, NH₂, —N(C₁-C₄-alkyl)₂ or —NH—SO₂CH₃;
E is a single bond, —O— or —S—;
$R^6$ is
(a) C₁-C₅ alkyl optionally substituted with a substituent selected from the group consisting of C₃-C₅-cycloalkyl, Cl, CF₃, CCl₃, —O—CH₃, —OC₂H₅, —S—CH₃, —S—C₂H₅, phenyl, or F,
(b) C₂-C₅-alkenyl or C₂-C₅-alkynyl, or,
(c) C₃-C₅-cycloalkyl;
$R^{7a}$ and $R^{7b}$ are each H;

$R^{8a}$ and $R^{8b}$ are independently
(a) H,
(b) C₁-C₄-alkyl optionally substituted with COOR⁴, OCOR⁴ᵃ, OH, or aryl,
(c) C₂-C₄-alkenyl,
(d) —OH,
(e) —NO₂,
(f) —NHCOR²³,
(g) —C₁-C₄-alkoxy,
(h) —NHCO₂R²³,
(i) —NR⁴R²³,
(j) halogen (Cl, F, Br),
(k) —CF₃,
(l) —CO₂R⁴,
(m) —CO-aryl as defined above,
(n) —S(O)ₓ—C₁-C₄-alkyl,
(o) —SO₂—NH—C₁-C₄-alkyl,
(p) —SO₂—NH-aryl as defined above,
(q) —NHSO₂CH₃,
(r) aryl as defined above, or
(s) —NHCONR⁴R²³;
X is a single bond;
r is one.

In a class of this embodiment are those compounds of Formula (I) wherein:
$R^1$ is
(a) —COOH,

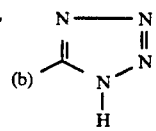

(c) —NH—SO₂—R²³,
(d) —SO₂NH-heteroaryl as defined above,
(e) —SO₂NH—CO—R²³, or
(f) —CONH—SO₂R²³;
E is a single bond;
r is one;
$R^{2a}$, $R^{2b}$, $R^{3a}$ and $R^{3b}$ are each H, —C₁-C₆-alkyl, —C₂-C₄-alkynyl, —Cl, —F, —NO₂, or —CF₃;
$R^6$ is —C₁-C₄-alkyl, -cyclopropyl, —CH₂CH₂CH₂CF₃, —CH₂CH₂CF₃, —C₂-C₅-alkenyl, or -cyclopropylmethyl;
$R^{8a}$ and $R^{8b}$ are each independently H, —C₁-C₄-alkyl, —NO₂, —NR⁴R²³, —OCH₃, —NHCOOR²³, —Cl, —CH₂COOH, —S(O)ₓ—C₁-C₄-alkyl, NHCONR⁴R²³, CH₂OCO(C₁-C₄—alkyl), NHCOR²³, CO₂R⁴, or —F.

In a subclass of this class are those compounds of Formula (I) wherein:
$R^1$ is
(a) COOH,

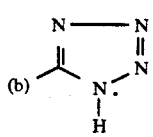

(c) —SO₂NHCOR²³,
(d) —CONHSO₂R²³, or
(e) —NHSO₂CF₃;
$R^{2a}$, $R^{2b}$, $R^{3a}$ and $R^{3b}$ are each H, —C₁-C₄-alkyl, —Cl or F;

R[6] is -n-propyl, ethyl, -n-butyl, -trans-2-butenyl, $CH_2CH_2CF_3$, $-CH_2CH_2CH_2CF_3$-cyclopropyl, or -cyclopropylmethyl;

R[8a] and R[8b] are each independently H, $-NO_2$, $-C_1-C_4$-alkyl, $-NH_2$, $-NHCOCH_3$, $-S(O)_x-(C_1-C_4$-alkyl), $-N(CH_3)_2$, $-OCH_3$, $-NHCOCH_2NH_2$, $-NHCOCH_2N(CH_3)_2$, $-COOH$, $-COOCH_3$, $-CH_2OCOCH_3$, Cl, $-CH_2COOCH_3$, $-NHCON(R^4)_2$, $-NHCO_2R^4$, $-CH_2COOH$, $-OCH_3$, $CH_2OH$, or NHMe.

Exemplifying this embodiment are the following compounds:

(1) 2-Butyl-1-[(2'-carboxybiphen-4-yl)methyl]quinazolin-4(1H)-one;
(2) 2-Butyl-1-[(2'-(tetrazol-5-yl)biphen-4-yl)methyl]-quinazolin-4(1H)-one;
(3) 2-Propyl-1-[(2'-(tetrazol-5-yl)biphen-4-yl)methyl]-quinazolin-4(1H)-one;
(4) 2-Butyl-6-methyl-1-[(2'-(tetrazol-5-yl)biphen-4-yl)methyl]quinazolin-4(1H)-one;
(5) 2-Butyl-6-dimethylamino-1-[(2'-(tetrazol-5-yl)biphen-4-yl)methyl]quinazolin-4(1H)-one;
(6) 2-Butyl-5-methyl-1-[(2'-(tetrazol-5-yl)biphen-4-yl)methyl]quinazolin-4(1H)-one;
(7) 2-Butyl-7-methyl-1-[(2'-(tetrazol-5-yl)biphen-4-yl)methyl]quinazolin-4(1H)-one;
(8) 2-Butyl-6-nitro-1[(2'-(tetrazol-5-yl)biphen-4-yl)methyl]quinazolin-4(1H)-one;
(9) 2-Butyl-8-methyl-1-[(2'-(tetrazol-5-yl)biphen-4-yl)methyl]quinazolin-4(1H)-one; and,
(10) 2-Butyl-5-carboxy-1-[(2'-(tetrazol-5-yl)biphen-4-yl)methyl]quinazolin-4(1H)-one.

In a second embodiment are those compounds of formula (I) wherein:

K is $-C(O)-$;

J and L are connected together to form a 6 carbon aromatic ring substituted with R[7a], R[7b], R[8a] and R[8b]; and, the class and sub-class of this embodiment are as defined above.

Exemplifying this embodiment are the following compounds:

(1) 2-Butyl-3-[(2'-carboxybiphen-4-yl)methyl]quinazolin-4(3H)-one;
(2) 2-Butyl-3-[(2'-carboxybiphen-4yl)methyl]-5-methyl-quinazolin-4(3H)-one;
(3) 2-Butyl-3-[(2'-carboxybiphen-4-yl)methyl]-naphtho[2,3-e]quinazolin-4(3H)-one;
(4) 2-Butyl-3-[(2'-carboxybiphen-4-yl)methyl]-7-methylquinazolin-4(3H)-one;
(5) 2-Butyl-3-[(2'-carboxybiphen-4-yl)methyl]-8-methylquinazolin-4(3H)-one;
(6) 2-Butyl-3-[(2'-carboxybiphen-4-yl)methyl]-6-methylquinazolin-4(3H)-one;
(7) 2-Butyl-3-[(2'-carboxybiphen-4-yl)methyl]-6-nitroquinazolin-4(3H)-one;
(8) 2-Butyl-3-[(2'-carboxybiphen-4-yl) methyl]-6,8-dimethylquinazolin-4(3H)-one;
(9) 6-Amino-2-butyl-3-[(2'-carboxybiphen-4-yl)methyl]-quinazolin-4(3H)-one;
(10) 6-Acetamido-2-butyl-3-[(2'-carboxybiphen-4-yl)methyl]quinazolin-4(3H)-one;
(11) 2-Butyl-3-[(2'-carboxybiphen-4-yl)methyl]-6-isopropylquinazolin-4(3H)-one;
(12) 2-Butyl-6-ethyl-3-[(2'-(tetrazol-5-yl)biphen-4-yl)methyl]quinazolin-4(3H)-one;
(13) 2-Butyl-7-chloro-3-[(2'-(tetrazol-5-yl)biphen-4-yl)methyl]quinazolin-4(3H)-one;
(14) 2-Butyl-6-isopropyl-3-[(2'-(tetrazol-5-yl)biphen-4-yl)methyl]quinazolin-4(3H)-one;
(15) 2-Butyl-6-methyl-3-[(2'-(tetrazol-5-yl)biphen-4-yl)methyl]quinazolin-4(3H)-one;
(16) 2-Butyl-3-[(2'-(tetrazol-5-yl)biphen-4-yl)methyl]-quinazolin-4(3H)-one;
(17) 6-Methyl-2-propyl-3-[(2'-(tetrazol-5-yl)biphen-4-yl)methyl]quinazolin-4(3H)-one;
(18) 2-Butyl-6-(N-isobutyloxycarbonyl)amino-3-[(2'-(tetrazol-5-yl)biphen-4-yl)methyl]quinazolin-4(3H)-one;
(19) 2-Butyl-3-[(2'-(tetrazol-5-yl)biphen-4-yl)methyl]-6-thiomethylquinazolin-4(3H)-one;
(20) 2-Butyl-6-methylsulfonyl-3-[(2'-(tetrazol-5-yl)biphen-4-yl)methyl]quinazolin-4(3H)-one;
(21) (N-Benzyl)amino-2-butyl-3-[(2'-(tetrazol-5-yl)biphen-4-yl)methyl]-6-quinozolin-4(3H)-one;
(22) 6-Acetamido-2-butyl-3-[(2'-tetrazol-5-yl)biphen-4-yl)methyl]quinazolin-4(3H)-one;
(23) 2-Butyl-3-[(2'-(tetrazol-5-yl)-biphen-4-yl)methyl]-6-valeroylamidoquinazolin-4(3H)-one;
(24) 2-Butyl-6-(N-carbobenzyloxy)amino-3-[(2'-(tetrazol-5-yl)biphen-4-yl)methyl]quinazolin-4(3H)-one;
(25) 2-Butyl-6-hydroxymethyl-3-[(2'-tetrazol-5-yl)biphen-4-yl)methyl]quinazolin-4(3H)-one;
(26) 2-Butyl-5-hydroxymethyl-3-[(2'-(tetrazol-5-yl)biphen-4-yl)methyl]quinazolin-4(3H)-one;
(27) 2-Butyl-6-(N-methyl)amino-3-[(2'-(tetrazol-5-yl)biphen-4-yl)-methyl]quinazolin-4(3H)-one;
(28) 2-n-Butyl-6-(N,N-dimethyl)amino-3-[(2'-(tetrazol-5-yl)biphen-4-yl)methyl]quinazolin-4(3H)-one;
(29) 2-Butyl-6-methoxy-3-[(2'-tetrazol-5-yl)biphen-4-yl)methyl]quinazolin-4(3H)-one;
(30) 2-Butyl-6-(N-glycyl)amino-3-[(2'-(tetrazol-5-yl)biphen-4-yl)methyl]quinazolin-4(3H)-one;
(31) 2-Butyl-6-(N-isopropylcarbamoyl)amino-3-[(2'-(tetrazol-5-yl)biphen-4-yl)methyl]quinazolin-4(3H)-one;
(32) 6-(N-Isopropylcarbamoyl)amino-2-propyl-3-[(2'-(tetrazol-5-yl)biphen-4-yl)methyl]quinazolin-4(3H)-one;
(33) 2-Butyl-6-methylsulfinyl-3-[(2'-(tetrazol-5-yl)biphen-4-yl)methyl]quinazolin-4(3H)-one;
(34) 2-Butyl-6-propylsulfinyl-3-[(2'-(tetrazol-5-yl)biphen-4-yl)methyl]quinazolin-4(3H)-one;
(35) 6-Acetoxymethyl-2-butyl-3-[(2'-(tetrazol-5-yl)biphen-4-yl)methyl]quinazolin-4(3H)-one;
(36) 2-Butyl-6-carboxy-3-[(2'-(tetrazol-5-yl)biphen-4-yl)methyl]quinazolin-4(3H)-one;
(37) 2-Butyl-6-carbomethoxy-3-[(2'-(tetrazol-5-yl)biphen-4-yl)methyl]quinazolin-4(3H)-one;
(38) 5-Acetoxymethyl-2-butyl-3-[(2'-(tetrazol-5-yl)biphen-4-yl)methyl]quinazolin-4(3H)-one;
(39) 2-Butyl-5-carboxy-3-[(2'-(tetrazol-5-yl)biphen-4-yl)methyl]quinazolin-4(3H)-one;
(40) 2-Butyl-5-carbomethoxy-3-[(2'-(tetrazol-5-yl)biphen-4-yl)methyl]quinazolin-4(3H)-one;
(41) 2-Butyl-5-carbomethoxymethyl-3-[(2'-(tetrazol-5-yl)biphen-4-yl)methyl]quinazolin-4(3H)-one;
(42) 2-Butyl-5-carbomethoxy-6-methyl-3-[(2'-(tetrazol-5-yl)biphen-4-yl)methyl]quinazolin-4(3H)-one;
(43) 2-(trans-2-Butenyl)-6-methylsulfinyl-3-[(2'-(tetrazol-5-yl)biphen-4-yl)methyl]quinazolin-4(3H)-one;
(44) 6-Methylsulfinyl-3-[(2'-(tetrazol-5-yl)biphen-4-yl)methyl]-2-(3,3,3-trifluoropropyl)quinazolin-4(3H)-one;

(45) 6-Methylsulfinyl-3-[(2'-(tetrazol-5-yl)biphen-4-yl)methyl]-2-(4,4,4-trifluorobutyl)quinazolin-4(3H)-one;
(46) 2-Butyl-6-methyl-3-[(2'-(N-phenylsulfonyl)carboxamidobiphen-4-yl)methyl]quinazolin-4(3H)-one;
(47) 2-Butyl-6-(N-isopropylcarbamoyl)amino-3-[(2'-(N-phenylsulfonyl)carboxamidobiphen-4-yl)methyl]-quinazolin-4(3H)-one;
(48) 2-Butyl-5-carboxy-3-[(2'-(N-methylsulfonyl)carboxamidobiphen-4-yl)methyl]quinazolin-4(3H)-one;
(49) 3-[(2'-(N-(Acetyl)aminosulfonyl)-biphen-4-yl)methyl]-2-butyl-5-carbomethoxyquinazolin-4(3H)-one;
(50) 3-[(2'-(N-Benzoyl)aminosulfonyl)-biphen-4-yl)methyl]-2-butyl-6-isopropylquinazolin-4(3H)-one;
(51) 2-Butyl-6-isopropyl-3-[(2'-(N-(trifluoromethyl)aminosulfonyl)-biphen-4-yl)methyl]quinazolin-4(3H)-one;
(52) 2-Butyl-6-methyl-3-[(2'-trifluoromethylsulfonamidobiphen-4-yl)methyl]quinazolin-4(3H)-one;
(53) 6-Amino-2-butyl-3-[(2'-(tetrazol-5-yl)biphen-4-yl)methyl]quinazolin-4(3H)-one;
(54) 2-Butyl-6-isopropyl-3-[(2'-(N-pyrimidin-2-yl)sulfonamidobiphen-4-yl)methyl]quinazolin-4(3H)-one;
(55) 2-Butyl-6-isopropyl-3-[(2'-(N-1,3,5-triazin-2-yl)sulfonamidobiphen-4-yl)methyl]quinazolin-4(3H)-one;
(56) 3-(2'-(N-(Acetyl)aminosulfonyl)-biphen-4-yl)methyl-2-butyl-6-isopropylquinazolin-4(3H)-one;
(57) 2-Butyl-6-nitro-3-[(2'-(tetrazol-5-yl)biphen-4-yl)methyl]quinazolin-4(3H)-one;
(58) 6-Amino-2-butyl-3-[(2'-(tetrazol-5-yl)biphen-4-methyl]quinazolin-4(3H)-one;
(59) 2-Butyl-3-(4'-fluoro-2'-(tetrazol-5-yl)biphen-4-yl)methyl-6-isopropylquinazolin-4(3H)-one.
(60) 2-Butyl-3-[2'-(N-benzenesulfonyl)carboxamidobiphen-4-yl)methyl]-6-isopropylquinazolin-4(3H)-one;
(61) 2-Butyl-3-[2'-(N-cyclopropylcarbonyl)sulfonamidomethylbiphen-4-yl)methyl]-6-isopropylquinazolin-4(3H)-one;
(62) 2-Butyl-3-[2'-(N-(4-fluorobenzyl)sulfonamidomethylbiphen-4-yl)methyl]-6-isopropylquinazolin-4(3H)-one; and
(63) 2-Butyl-3-[2'-(N-benzoyl)sulfonamidomethylbiphen-4-yl)methyl]-6-isopropylquinazolin-4(3H)-one.

In a third embodiment are those compounds of formula (I) wherein:
K is —C(=NR$^{22}$)—;
J and L are connected together to form a 6 carbon aromatic ring substituted with R$^{7a}$, R$^{7b}$, R$^{8a}$ and R$^{8b}$; and, the class and sub-class of this embodiment are as defined above.

Exemplifying this embodiment are the following compounds:
(1) N-Methyl-2-butyl-6(N-isopropylcarbamoyl)amino-3-[(2'-(tetrazol-5-yl)biphen-4-yl)methyl]quinazolin-4(3H)-imine;
(2) N-Propyl-2-butyl-6-methylsulfinyl-3-[(2'-(tetrazol-5-yl)biphen-4-yl)methyl]quinazolin-4(3H)-imine;
(3) N-Carboxymethyl-2-butyl-6-propylsulfinyl-3-[(2'-(tetrazol-5-yl)biphen-4-yl)methyl]quinazolin-4(3H)-imine;
(4) N-Methyl-6-acetoxymethyl-2-butyl-3-[(2'-(tetrazol-5-yl)biphen-4-yl)methyl]quinazolin-4(3H)-imine;
(5) N-Phenyl-2-butyl-6-carboxy-3-[(2'-(tetrazol-5-yl)biphen-4-yl)methyl]quinazolin-4(3H)-imine;
(6) N-Ethyl-2-butyl-6-carbomethoxy-3-[(2'-(tetrazol-5-yl)biphen-4-yl)methyl]quinazolin-4(3H)-imine;
(7) N-Methyl-5-acetoxymethyl-2-butyl-3-[(2'-(tetrazol-5-yl)biphen-4-yl)methyl]quinazolin-4(3H)-imine;
(8) N-(Pyridin-4-yl)methyl 2-butyl-5-carboxy-3-[(2'-(tetrazol-5-yl)biphen-4-yl)methyl]quinazolin-4(3H)-imine;
(9) N-(2-Carboxy)ethyl-2-butyl-5-carboxymethyl-3-[(2'-(tetrazol-5-yl)biphen-4-yl)methyl]quinazolin-4(3H)-imine;
(10) N-Methyl-2-butyl-5-carbomethoxy-3-[(2'-tetrazol-5-yl)biphen-4-yl)methyl]quinazolin-4(3H)-imine;
(11) N-Methyl-2-butyl-5-carbomethoxy-3-[(2'-(tetrazol-5-yl)biphen-4-yl)methyl]quinazolin-4(3H)-imine;
(12) N-Ethyl-2-butyl-5-carbomethoxy-6-methyl-3-[(2'-(tetrazol-5-yl)biphen-4-yl)methyl]quinazolin-4(3H)-imine;
(13) N-Butyl-2-(2-trans-butenyl)-6-methylfulfinyl-3-[(2'-(tetrazol-5-yl)biphen-4-yl)methyl]quinalozin-4(3H)-imine;
(14) N-Methyl-6-methylsulfinyl-3-[(2'-(tetrazol-5-yl)-biphen-4-yl)-methyl]-2-(3,3,3-trifluoropropyl)-quinazolin-4(3H)-imine;
(15) N-Benzyl-6-methylsulfinyl-3-[(2'-(tetrazol)5-yl)-biphen-4-yl)methyl]-2-(4,4,4-trifluorobutyl)-quinazolin-4(3H)-imine;
(16) N-Benzyl-2-butyl-6-methyl-3-[(2'-(N-phenylsulfonyl)carboxamidobiphen-4-yl)methyl]quinazolin-4(3H)-imine;
(17) N-(4-Chloro)phenyl-2-butyl-6-(N-isopropylcarbamoyl)amino-3-[(2'-(N-phenylsulfonyl)carboxamidobiphen-4-yl)methyl]quinazolin-4(3H)-imine;
(18) N-Methyl-2-butyl-5-carboxy-3-[(2'-(N-methylsulfonyl)carboxymidobiphen-4-yl)methyl]quinazolin-4(3H)-imine;
(19) N-Methyl-3-[2'-(N-(acetyl)aminosulfonyl-biphen-4-yl)methyl]-2-butyl-5-carbomethoxyquinazolin-4(3H)-imine;
(20) N-Methyl-3-[2'-(N-(benzoyl)aminosulfonyl)-biphen-4-yl)-methyl]-2-butyl-6-isopropylquinazolin-4(3H)-imine;
(21) N-Methyl-2-butyl-6-isopropyl-3[2'-(N-trifluoroacetyl)aminosulfonyl)-biphen-4-yl)-methyl]quinazolin-4-(3H)-imine;
(22) N-Methyl-2-butyl-6-isopropyl-3-[(2'-(N-2-pyrimidinoyl)aminosulfonyl)-biphen-4-yl-methyl]-quinazolin-4(3H)-imine;
(23) N-Methyl-2-butyl-6-isopropyl-3-[(2'-(N-(1,3,5-triazin-2-yl)aminosulfonyl)-biphen-4-yl)methyl]-quinazolin-4(3H)-imine;
(24) N-Methyl-3-[(2'-(N-(acetyl)aminosulfonyl)methyl-biphen-4-yl)methyl]-2-butyl-6-isopropylquinazolin-4(3H)-imine; and,
(25) N-Methyl-3-[(2'-(N-(acetyl)aminosulfonylmethyl)-biphen-4-yl)methyl]-2-butyl-6-isopropylquinazolin-4(3H)-imine.

In naming compounds of Formula (I) which contain a biphenylmethyl substituent, it should be noted that the following two names for compound (i) shown below are considered to be equivalent:

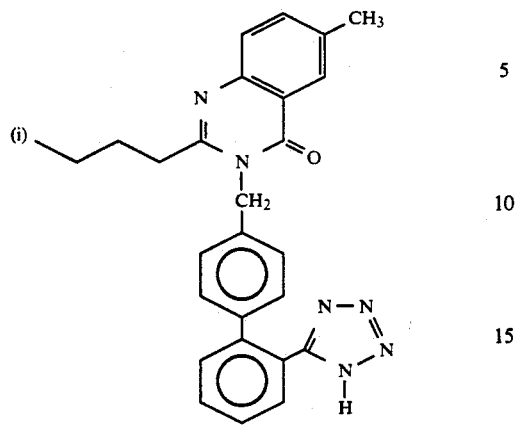

(1) 2-Butyl-6-methyl-3-[(2'-(tetrazol-5-yl)biphen-4-yl)methyl]quinazolin-4(3H)-one; or, (2) 2-n-Butyl-6-methyl-3-[(2'-(tetrazol-5-yl)[1,1']biphenyl-4-yl)methyl]quinazolin-4(3H)-one.

| ABBREVIATIONS USED IN SCHEMES | |
|---|---|
| DMAP | Dimethylaminopyridine |
| —OTs | p-toluenesulphonate |
| —OTf | Trifluoromethanesulfonate |
| DMF | Dimethylformamide |
| DBU | 1,8-Diazabicyclo[5.4.0]undecane |
| FABMS | Fast Atom bombardment mass spectroscopy |
| THF | Tetrahydrofuran |
| DMSO | Dimethylsulfoxide |
| EtAc | Ethyl acetate |
| HOAc | Acetic Acid |
| TFA | Trifluoroacetic acid. |

Scheme 1 illustrates the preparation of 1,2-disubstituted quinazolin-4(1H)-ones of Formula 1 wherein J=—C(O)— and E is a single bond. An appropriately substituted anthranilonitrile is acylated using the requisite acyl chloride. The resulting amide is alkylated with sodium hydride and the appropriate alkyl halide (or pseudohalide). The resulting tertiary amide is then rearranged/cyclized with basic hydrogen peroxide[1]. 2-Substituted quinazolin-4-(1H)-ones 6 wherein E is a single bond and K is —C(O)— may be prepared from substituted anthranilonitriles as described in Scheme 1. The appropriately substituted anthranilonitrile is acylated using the requisite acyl chloride to give 2 then cyclized with basic hydrogen peroxide to give 6.

SCHEME 1

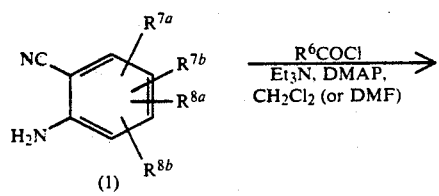

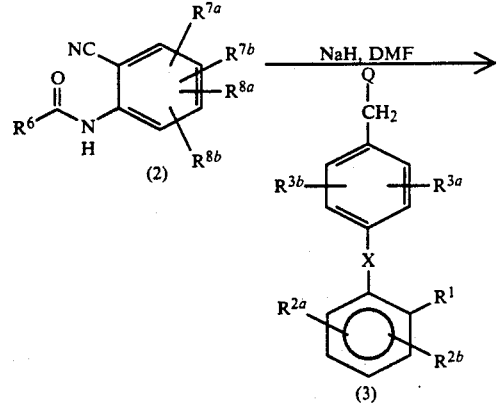

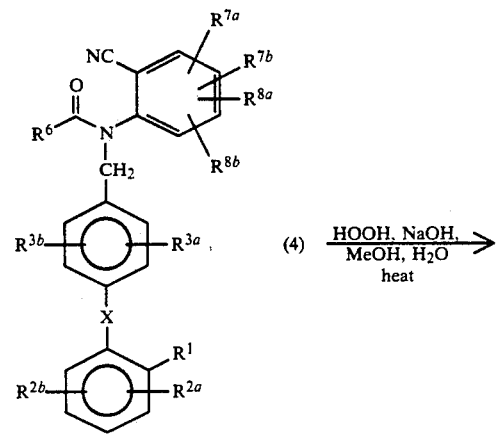

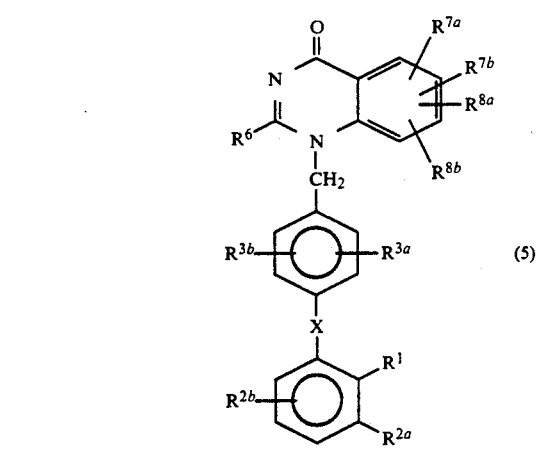

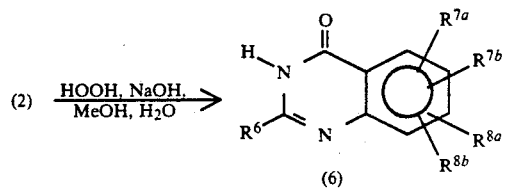

SCHEME 2

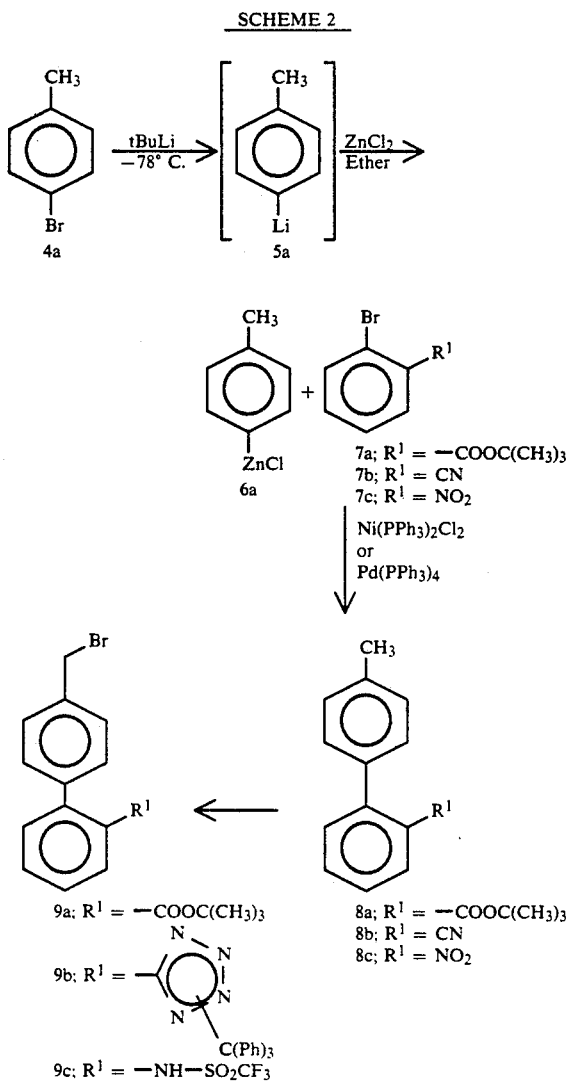

The benzyl halides (3) including the more preferred alkylating agents (9a and 9b, Reaction Scheme 2) can be prepared as described in European Patent Applications 253,310 and 291,969 and the references cited therein. However, a preferred method to prepare the biphenyl precursors 8a, 8b and 8c using Ni(O) or Pd(O) catalyzed cross-coupling reaction [E. Negishi, T. Takahashi, and A. O. King, *Org. Synthesis*, 66, 67 (1987)] is outlined in Reaction Scheme 2. As shown in Reaction Scheme 2, treatment of 4-bromotoluene (4a) with t-BuLi, followed by the addition of a solution of $ZnCl_2$, produces the organo-zinc compound (6a). Compound (6a) is then coupled with 7a or 7b in the presence of $Ni(PPh_3)_2Cl_2$ catalyst to produce the desired biphenyl compound 8a or 8b ($PPh_3$=triphenylphosphine). Similarily, 1-iodo-2-nitro-benzene (7c) is coupled with organo-zinc compound 6a in the presence of $Pd(PPh_3)_4$ catalyst [prepared by treating $Cl_2Pd(PPh_3)_2$ with $(i-Bu)_2AlH$ (2 equiv.)] to give the biphenyl compound 8c. These precursors, 8a, 8b and 8c, are then transformed into halomethylbiphenyl derivatives 9a, 9b and 9c, respectively, according to procedures decribed in European Patent Applications 253,310 and 291,969.

When there is additional substitution on the second phenyl ring ($R^{2a}$, $R^{2b}$=hydrogen) the preferred method to prepare the biphenyl precursors 8d and 8e, using the Pd(O) catalyzed cross-coupling reaction [J. K. Stille, *Angew. Chem. Int. Ed. Engl.*, 25, 508 (1986)], is outlined in reaction Scheme 2a. As shown in reaction Scheme 2a, p-tolyltrimethyltin (6a) is coupled with 7d or 7e in refluxing toluene in the presence of 5 mole % of $Pd(PPh_3)_4$ to produce the desired biphenyl compounds 8d and 8e. Table I illustrates the synthetic utility of this protocol. Compounds 8d ($R^2=NO_2$) and 8e ($R^2=NO_2$) could be converted to their respective chlorides by catalytic hydrogenation, diazotization and treatment with copper (I) chloride. The biphenyl fluorides which could not be obtained by direct coupling to a fluoro arylbromide were prepared from 8d ($R^2=NO_2$) and 8e ($R^2=NO_2$) via reduction, formation of the diazonium tetrafluoroborate salt and thermal decomposition. These precursors 8d ($R^2=NO_2$ or F or Cl) and 8e ($R^2=NO_2$ or F or Cl) are then transformed into the halomethyl biphenyl derivatives 9d and 9e respectively according to the procedures described in European Patent Applications 253,310 and 292,969.

REACTION SCHEME 2a

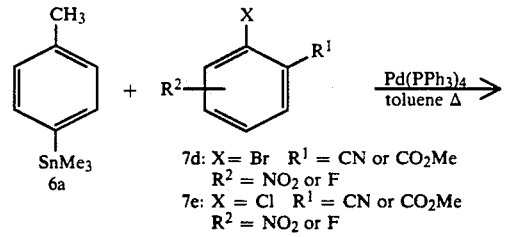

7d: X= Br  $R^1$ = CN or $CO_2Me$
  $R^2$ = $NO_2$ or F
7e: X = Cl  $R^1$ = CN or $CO_2Me$
  $R^2$ = $NO_2$ or F

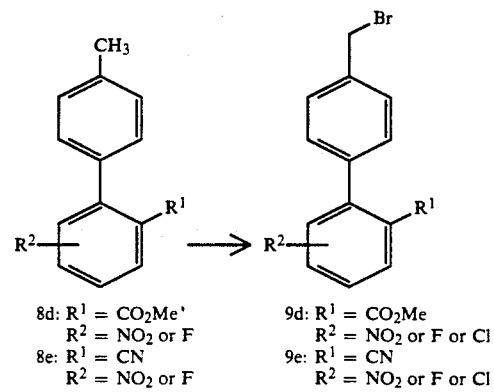

8d: $R^1$ = $CO_2Me$
  $R^2$ = $NO_2$ or F
8e: $R^1$ = CN
  $R^2$ = $NO_2$ or F

9d: $R^1$ = $CO_2Me$
  $R^2$ = $NO_2$ or F or Cl
9e: $R^1$ = CN
  $R^2$ = $NO_2$ or F or Cl

TABLE I
Biphenyl Synthesis

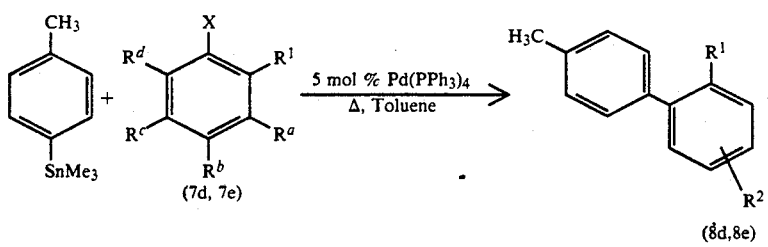

| X | $R^1$ | $R^a$ | $R^b$ | $R^c$ | $R^d$ | Product ($R^2$) | Rf (solvent) | Yield |
|---|---|---|---|---|---|---|---|---|
| Br | CO$_2$Me | NO$_2$ | H | H | H | 8d (3'-nitro) | 0.35 (15:1 Hex/EtOAc) | 71% |
| Br | CN | H | NO$_2$ | H | H | 8e (4'-nitro) | 0.62 (2 × 6:1 Hex/EtOAc) | 74% |
| Br | CO$_2$Me | H | F | H | H | 8d (4'-fluoro) | 0.43 (15:1 Hex/EtOAc) | 83% |
| Cl | CO$_2$Me | H | H | NO$_2$ | H | 8d (5'-nitro) | 0.22 (15:1 Hex/EtOAc) | 70% |
| Br | CO$_2$Me | H | H | H | NO$_2$ | 8d (6'-nitro) | 0.24 (15:1 Hex/EtOAc) | 79% |
| Br | CN | H | F | H | H | 8e (4'-fluoro) | 0.44 (15:1 Hex/EtOAc) | 64% |
| Cl | CN | H | H | F | H | 8e (5'-fluoro) | 0.40 (15:1 Hex/EtOAc) | 62% |

Scheme 3 shows an alternate preparation of 2-substituted quinazolin-4(3H)-ones (6) starting with the corresponding anthranilic acid. The appropriately substituted anthranilic acid (10) is treated with two equivalents of the requisite acyl chloride in DMF with triethylamine and DMAP at 0° C. This is then heated to 110° C. for two hours after which time excess ammonium carbonate is added.[2]

SCHEME 3

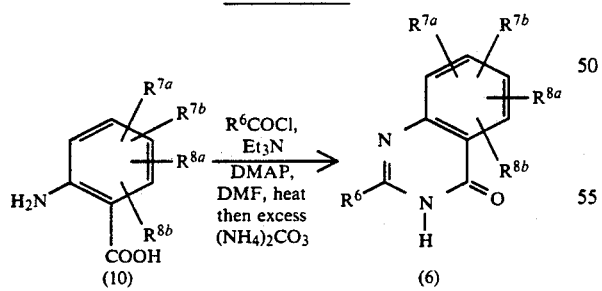

Scheme 4 illustrates the general preparation of 2,3-disubstituted quinazolin-4(3H)-ones (11a) of formula (I) wherein E is a single bond and K is —C(O)—. An appropriately substituted 2-substituted quinazolin-4(1H)-one (6) (see Scheme 1 or Scheme 3) is alkylated using sodium hydride and the appropriate alkyl halide (or pseudohalide). This reaction sometimes gives some O-alkylated product, generally less than 20% of the isolated reaction products.

SCHEME 4

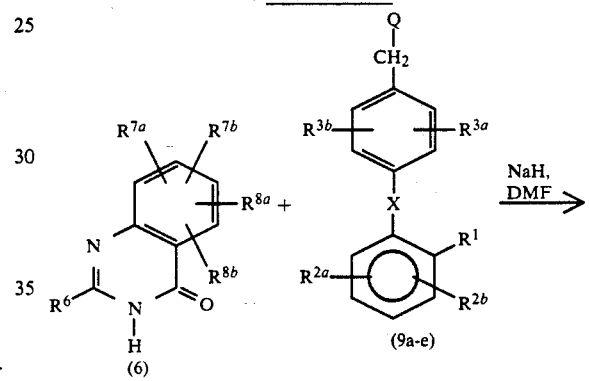

Schemes 5, 6, and 7 provide an alternate route to compounds of Formula (1) (11b) wherein E is a single bond, K is —C(O)—, and r is 1 or 2.

Two methods for preparing 3,1,4-benzoxazones (10) are illustrated in Scheme 5. Substituted anthranilic acids (10) may be acrylated and cyclized by heating them in DMF with an acyl chloride, triethylamine and DMAP.[3] Alternatively, they may also be prepared by heating an appropriately substituted anthranil (13) with an acyl chloride in pyridine.[4]

The necessary alkyl amine may then be prepared from the alkyl halide (or pseudohalide) using the standard literature procedures (Scheme 6)[5]. The amine where r=2 may be prepared from (9a-e) using procedures known to those skilled in the art where appropriate protecting groups are used for $R^1$, $R^{2a}$, $R^{2b}$, $R^{3a}$ and $R^{3b}$. Then, the amine and the 3,1,4-benzoxazone are heated together to give the desired 2,3-disubstituted quinazolinone (11b) (Scheme 7).

SCHEME 7

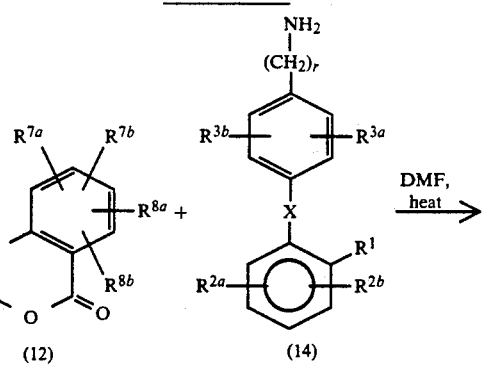

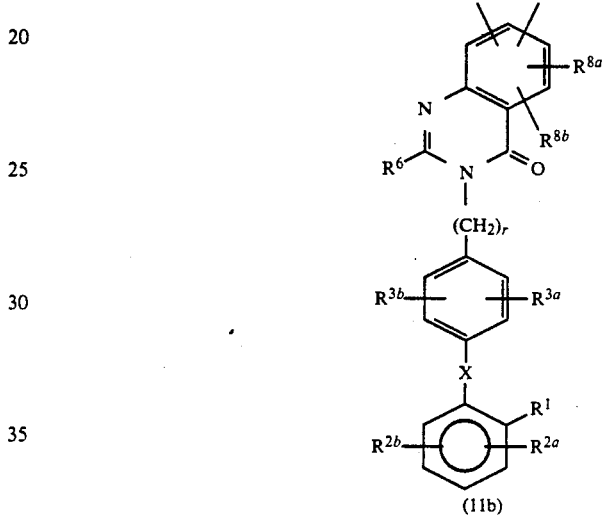

SCHEME 5

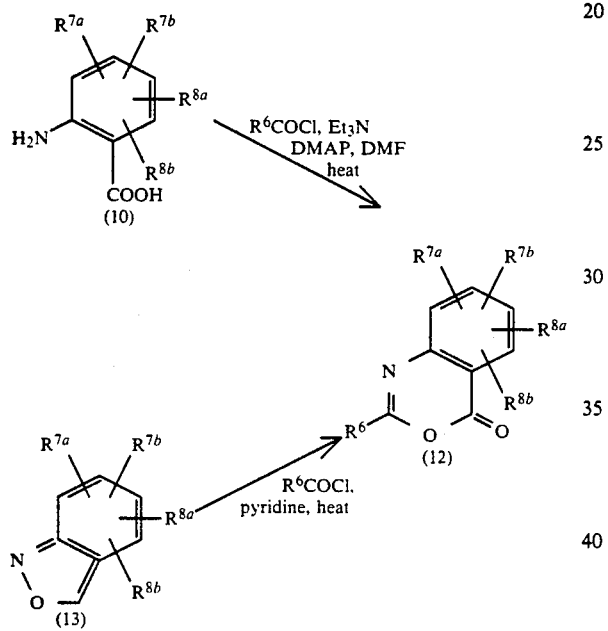

SCHEME 6

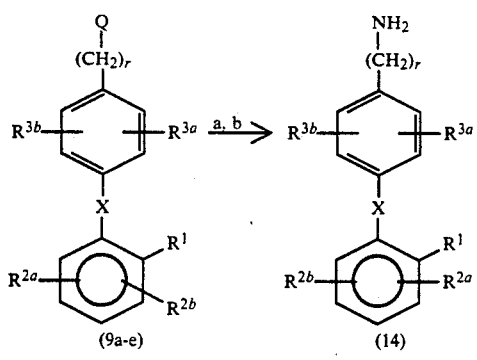

for r = 1:
a) LiN$_3$/DMSO
b) P(Ph)$_3$, H$_2$O
for r = 2:
a) Na$^+$ $^-$CH$_2$NO$_2$, DMF
b) H$_2$, 10% Pd/C Substituted 2-alkylthioquinazolin-4(3H)-ones wherein K is —C(O)— and E is —S— (15) may be prepared from their corresponding substituted anthranilic acids as shown in Scheme 8. The amine (14) from Scheme 6 can be converted to its isothiocyanate (16) upon treatment with thiophosgene. This may then be reacted with an appropriately substituted anthranilic acid to give the desired 3-alkyl-2-mercaptoquinazolin-4(3H)-one.(17)[6] A second alkylation of the mercapto group then gives the desired 2-alkylthio-3-alkyl-quinazolin-4(3H)-one.(15)[7]

SCHEME 8

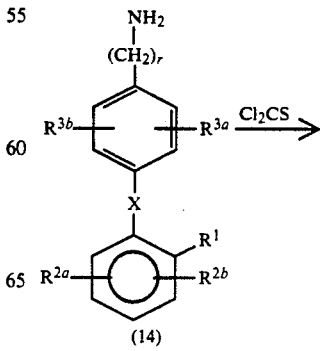

SCHEME 8

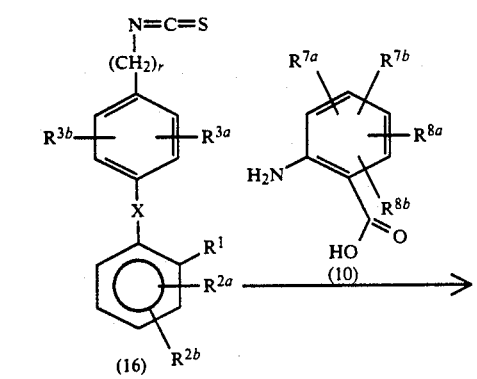

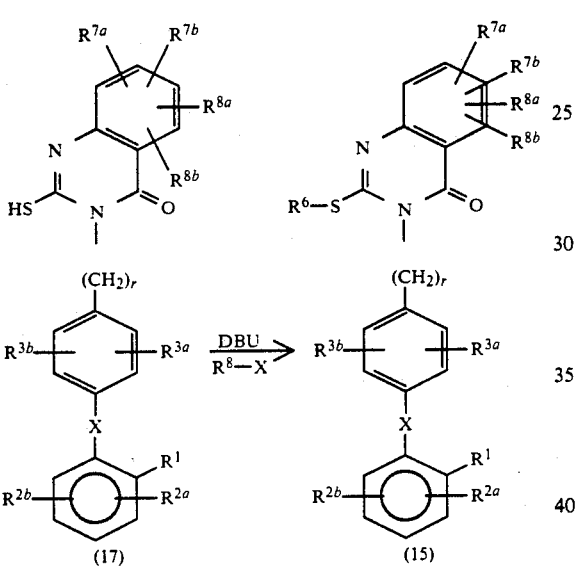

Similarly, 2-alkoxyquinazolin-4(3H)-ones wherein K is —C(O)— and E is —O— may be prepared from their corresponding substituted anthranilic acids as shown in Scheme 9.[8] Alkylation with the appropriate alkyl halide 9a-e according to the methods developed by Lange and Sheibley [9] then gives the final product 19.

SCHEME 9

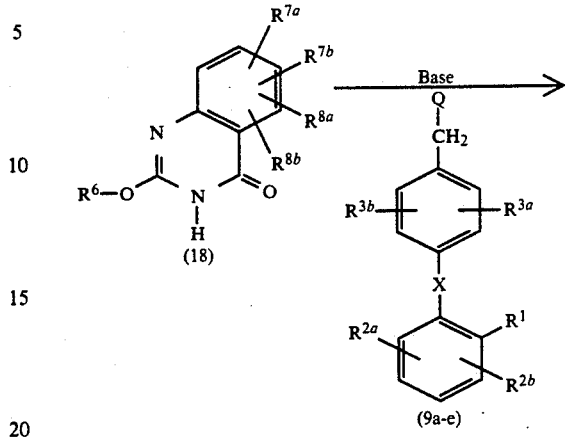

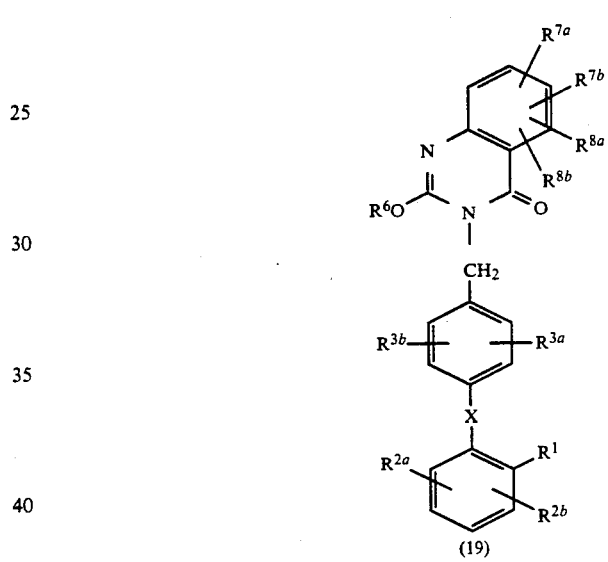

Scheme 10 illustrates a route to the isomeric 1,2-disubstituted quinazolin-4(1H)-ones (20) wherein J is —C(O)— and where E is S or O. An anthranilonitrile 1 is acylated with an alkyl haloformate or an alkylthiol haloformate to give 21.[10] This may then be deprotonated and alkylated with the appropriate alkyl halide to give the intermediate carbamate nitrile 22.[11] Conversion of the intermediate then occurs when the material is treated with basic hydrogen peroxide to yield the desired product 20.

SCHEME 9

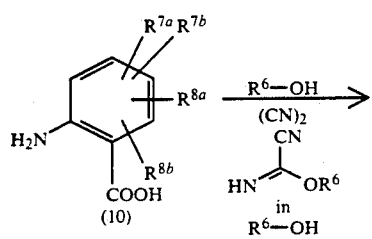

SCHEME 10

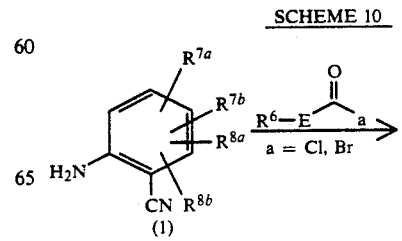

-continued
SCHEME 10
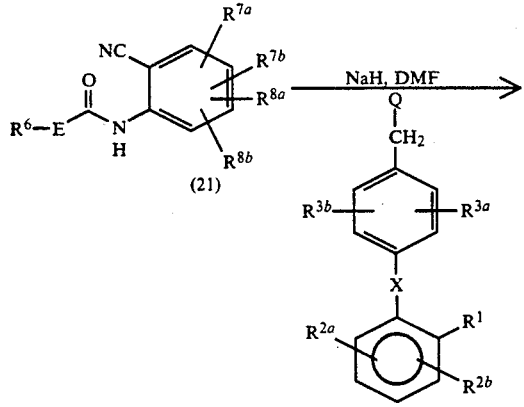
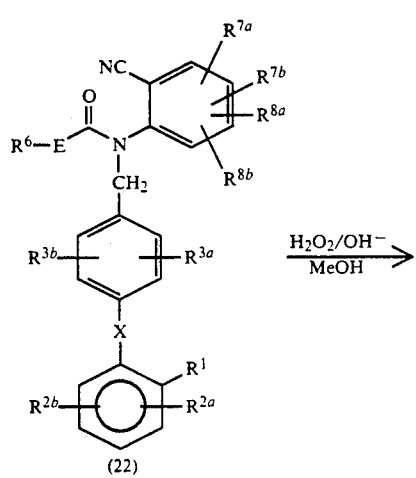
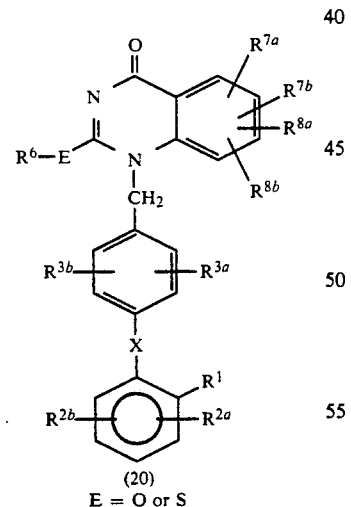
E = O or S
SCHEME 11
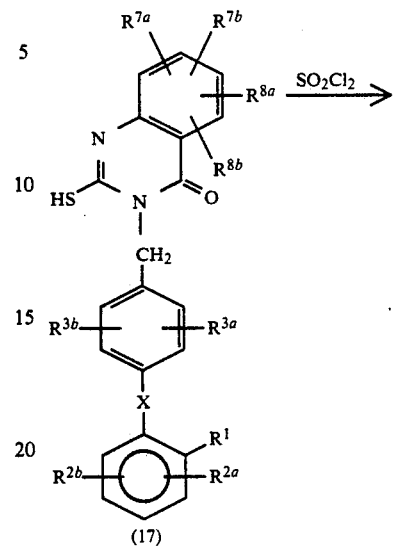
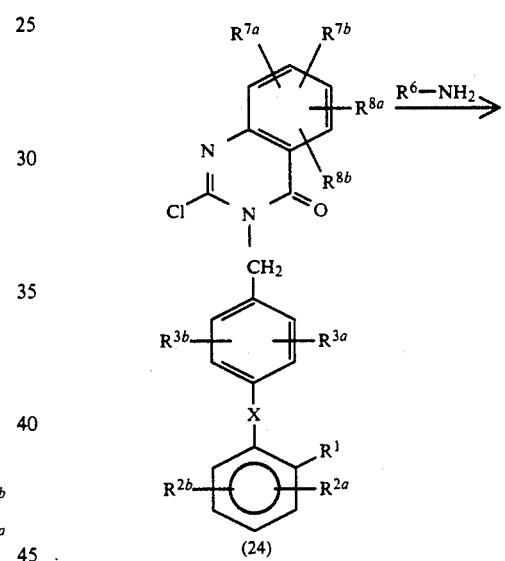
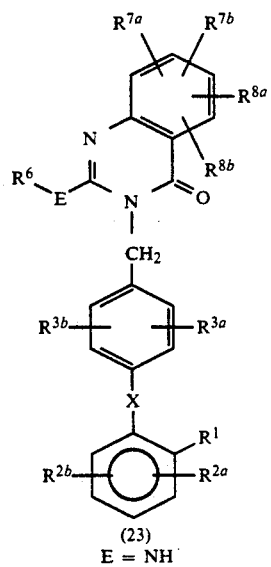
E = NH
Scheme 11 illustrates the method by which a 2-amino-3-alkylquinazolinone 23 can be made. The 2-mercaptoquinazolinone (17) shown in Scheme 8 can be treated with sulfuryl chloride to give the corresponding 2-chloroquinazolinone 24.[12] Displacement of the chloride with an $R^6$ amine then gives 23 with E=NH.[13]

Scheme 12 illustrates the method by which a 2-amino-1-alkylquinazolinone 24 can be made. The products from Scheme 10 where E is sulfur (20) can be used as a synthetic intermediate if the initial $R^6$ is a protecting group such as benzyl or t-butyl.[14] Deprotection and subjection of the resulting 2-mercapto-1-alkyl-quinazolinone to the same conditions used in Scheme 11 will result in the formation of the desired 2-amino-1-alkylquinazolinone. Alternatively, the sulfide may be displaced directly by an $R^6$ amine as shown in Scheme 13 ($R^6$—S— and $R^6$—NH$_2$ may or may not have the same $R^6$).

-continued
SCHEME 12

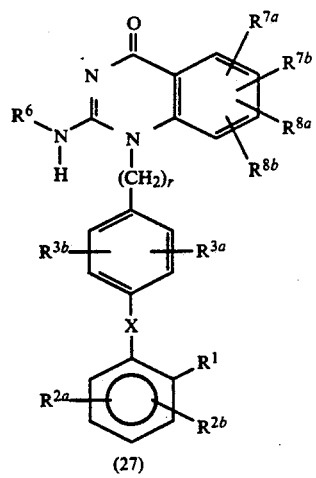

(27)

SCHEME 12

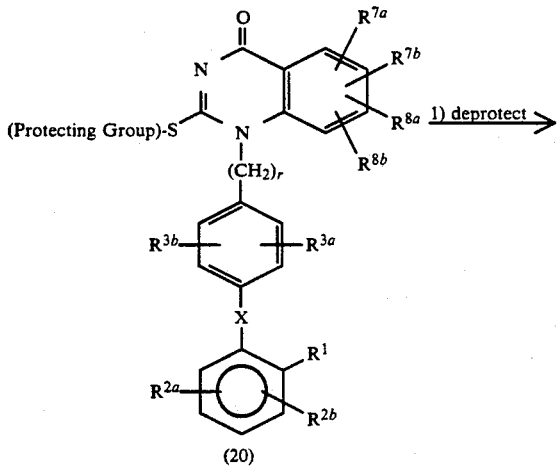

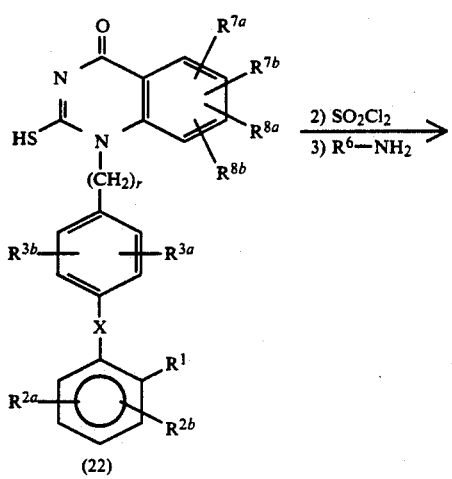

SCHEME 13

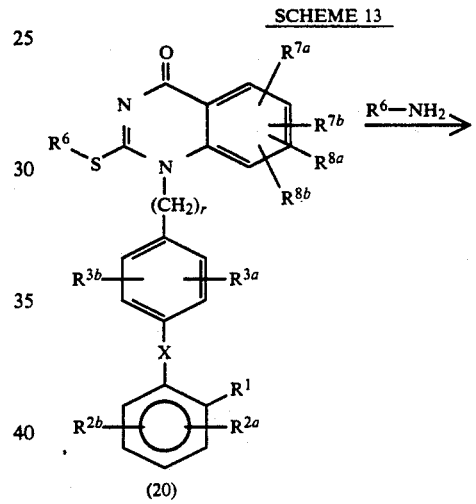

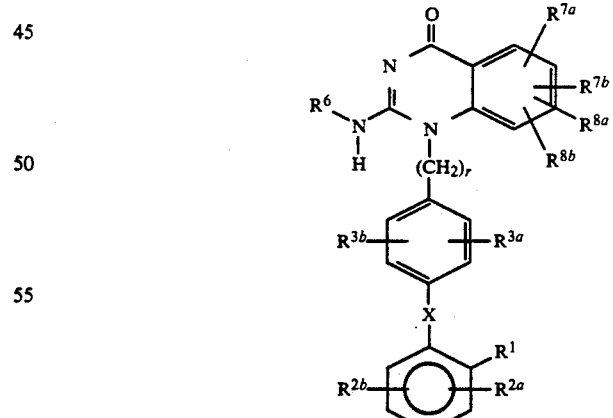

Scheme 14 illustrates the method by which a quinazolin-4(3H)-imine 27 may be prepared. A 3-substituted or unsubstituted quinazolin-4(3H)-one 25 can be converted to a quinazolin-4(3H)-thione 26 by the action of Lewesson's reagent. Addition of amine and heating will result in the formation of an imine 27 as shown.

SCHEME 14

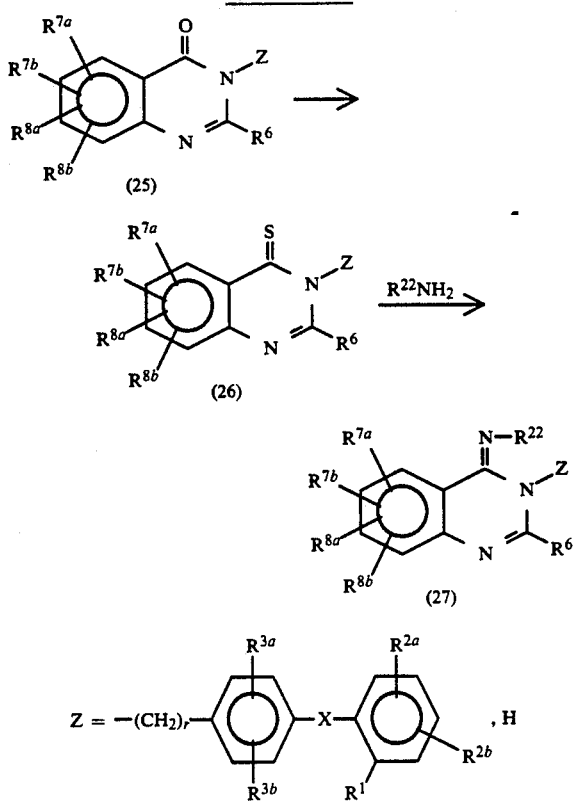

Compounds of formula I where R¹ is —CONH-SO$_2$R$^{23}$ (where R$^{23}$=alkyl, aryl or heteroaryl) may be prepared from the corresponding carboxylic acid derivatives (28) as outlined in Scheme 15. The carboxylic acid (28), obtained as described in Scheme 4, can be converted into the corresponding acid chloride by treatment with refluxing thionyl chloride or preferably with oxalylchloride and a catalytic amount of dimethylformamide at low temperature [A. W. Burgstahler, L. O. Weigel, and C. G. Shaefer-*Synthesis*, 767, (1976)]. The acid chloride then can be treated with the alkali metal salt of R$^{23}$SO$_2$NH$_2$ to form the desired acylsulfonamide 29. Alternatively, these acylsulfonamides may be also prepared from the carboxylic acids using N,N-diphenylcarbamoyl anhydride intermediates [F. J. Brown et al, European Patent Application, EP 199543; K. L. Shepard and W. Halczenko-*J. Het. Chem.*, 16, 321 (1979)]. Preferably the carboxylic acids can be converted into acyl-imidazole intermediates, which then can be treated with an appropriate aryl or alkylsulfonamide and diazabicycloundecane (DBU) to give the desired acylsulfonamide 29 [J. T. Drummond and G. Johnson, *Tet. Lett.*, 29, 1653 (1988)].

Compounds of formula I where R¹ is SO$_2$NHCOR$^{23}$ may be prepared as outlined in Scheme 16. The nitro compound 8c (prepared as described in Scheme 2) can be reduced to the corresponding amino compound and converted into aromatic diazoniun chloride salt, which then can be reacted with sulfur-dioxide in the presence of a copper (II) salt to form the corresponding arylsulfonyl chloride 30 [H. Meerwein, G. Dittmar, R. Gollner, K. Hafner, F. Mensch and O. Steifort, *Chem. Ber.*, 90, 841 (1957); A. J. Prinsen and H. Cerfontain, *Recueil*, 84, 24 (1965); E. E. Gilbert, *Synthesis*, 3 (1969) and references cited therein]. The sulfonyl chloride can be reacted with ammonia in aqueous solution or in an inert organic solvent [F. H. Bergheim and W. Baker, *J. Amer. Chem. Soc.*, 66, (1944), 1459], or with dry powdered ammonium carbonate, [E. H. Huntress and J. S. Autenrieth, *J. Amer. Chem. Soc.*, 63 (1941), 3446; E. H. Huntress and F. H. Carten, *J. Amer. Chem. Soc.*, 62, (1940), 511] to form the sulfonamide 31. The benzylbromide 33 may be prepared from the sulfonamide 31 as outlined in Scheme 16, and then can be reacted with an alkali metal salt of an appropriate heterocyclic compound to form the key sulfonamide 34. The sulfonamide 34 may be also prepared from the aromatic sulfonyl chloride 39, which may be prepared from the aryl amine 38 as outlined in Scheme 17. The acylation of 34 with appropriate acyl chlorides (or acyl-imidazoles or other acylating agents) may produce the desired acylsulfonamides 35.

The compounds bearing R¹ as —SO$_2$NHR$^{23}$ (where R$^{23}$ is heteroaryl) may be prepared by reacting the aromatic sulfonyl chloride 39 with appropriate heteroaryl amines as outlined in Scheme 17. The sulfonyl chloride 39 may be the preferred intermediate for the synthesis of this class of compounds. The aromatic sulfonyl chlorides may also be prepared by reacting the sodium salt of aromatic sulfonic acids with PCl$_5$ or POCl$_3$ [C. M. Suter, *The Organic Chemistry of Sulfur*, John Wiley & Sons, 459, (1944)]. The aromatic sulfonic acid precursors may be prepared by chlorosulfonation of the aromatic ring with chlorosulfonic acid [E. H. Huntress and F. H. Carten, *J. Amer. Chem. Soc.*, 62, 511 (1940)].

SCHEME 15

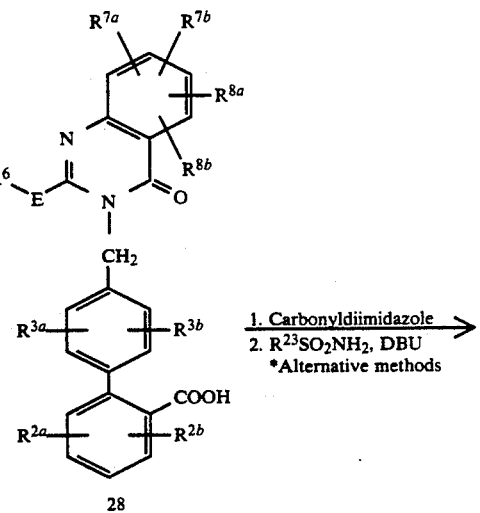

1. Carbonyldiimidazole
2. R$^{23}$SO$_2$NH$_2$, DBU
*Alternative methods

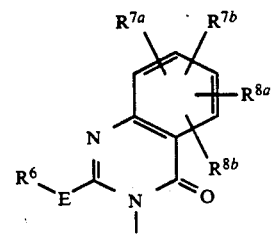

-continued
SCHEME 15
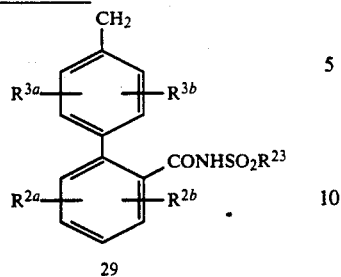
*Alternative Methods:
a) (i) SOCl₂, reflux
   (ii) R²³SO₂NH⁻M⁺ (where M is Na or Li)
b) (i) (COCl)₂-DMF, −20° C.
   (ii) R²³SO₂NH⁻M⁺
c) (i) N(N,N-Diphenylcarbamoyl)pyridinium chloride/Aq. NaOH
   (ii) R²³SO₂NH⁻M⁺.
SCHEME 16
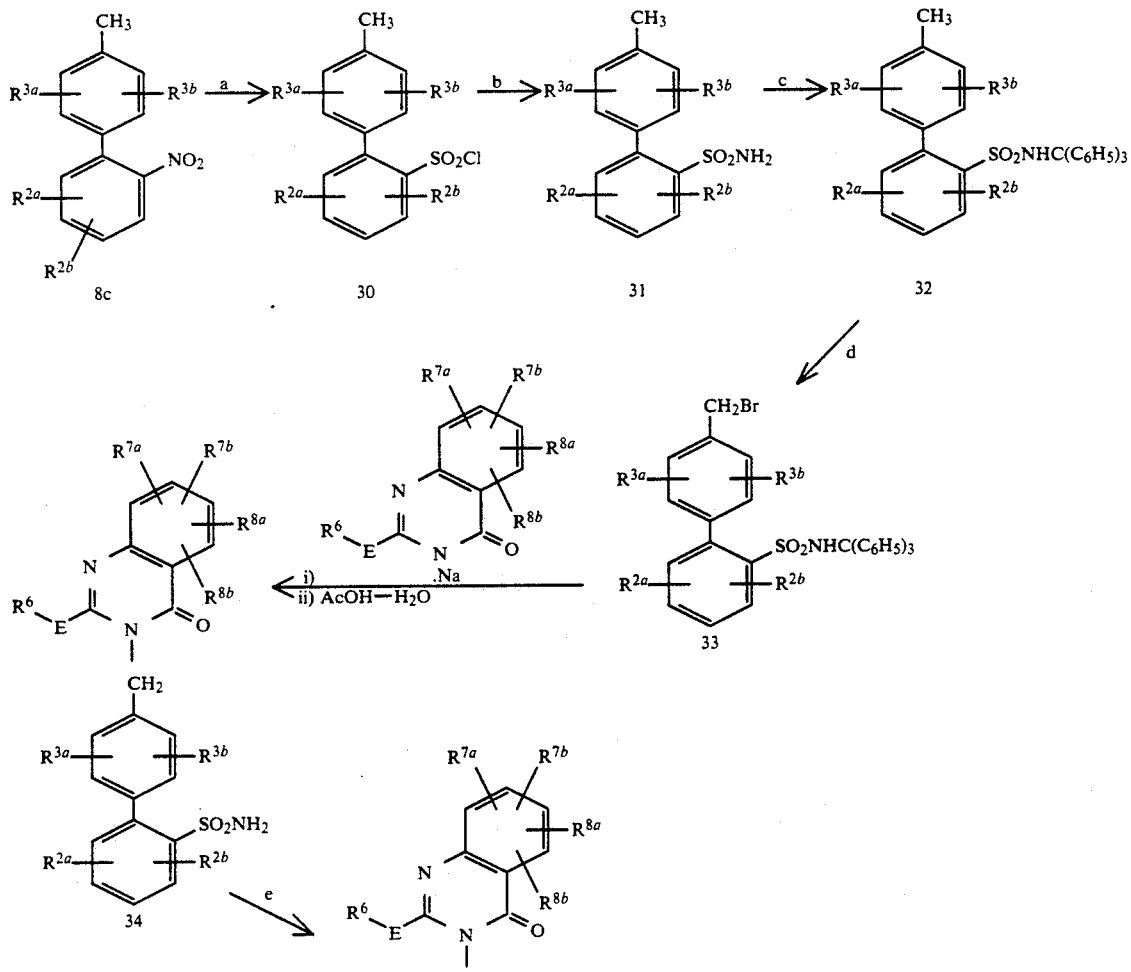

-continued
SCHEME 16
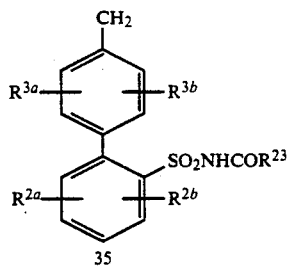
a. (i) H₂/Pd—C
   (ii) NaNO₂—HCl,
   (iii) SO₂, AcOH, CuCl₂
b. NH₃ or (NH₄)₂CO₃
c. (C₆H₅)₃CCl, Et₃N, CH₂Cl₂, 25° C.
d. N-Bromosuccinimide
e. $R^{23}$COCl or $R^{23}$CO—Im or other acylating agents.
SCHEME 17
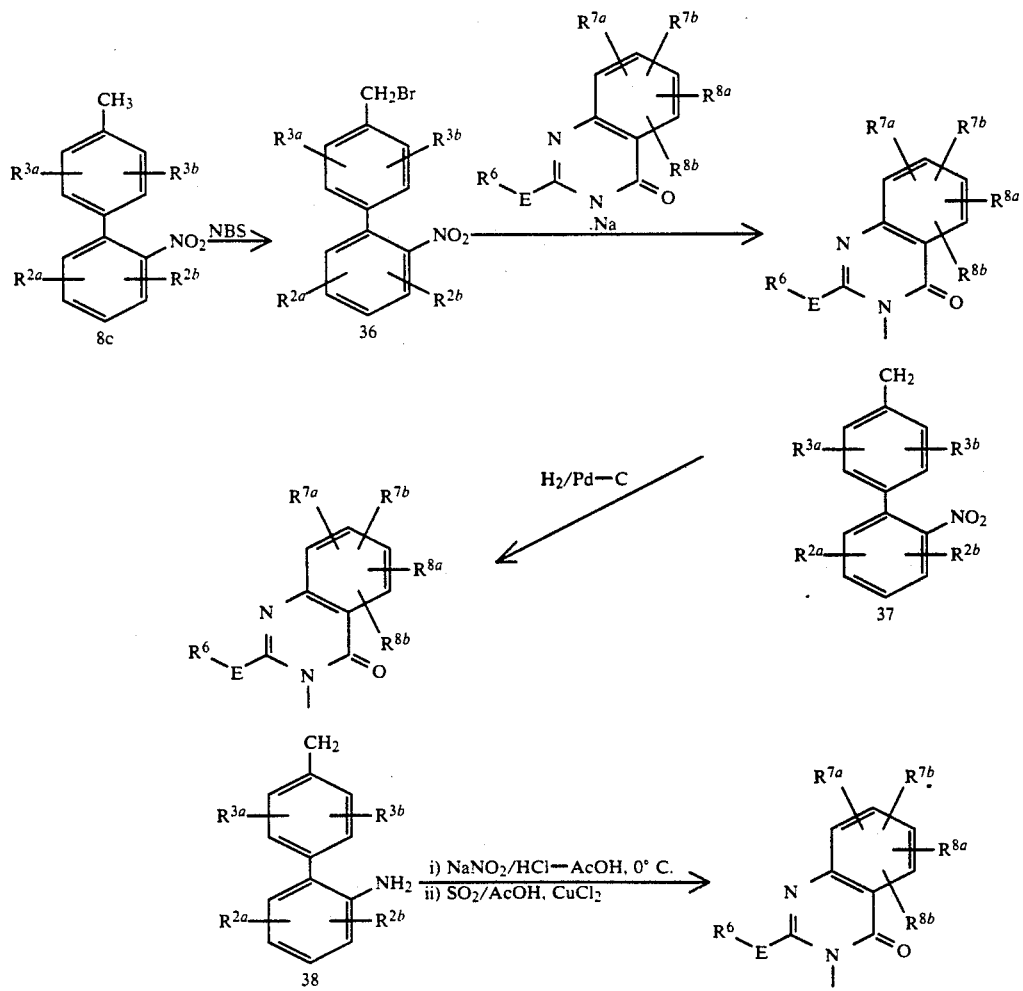

-continued
SCHEME 17

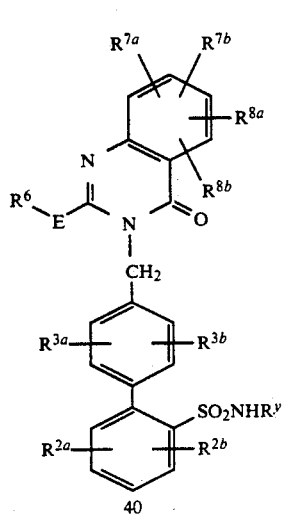

SCHEME 18

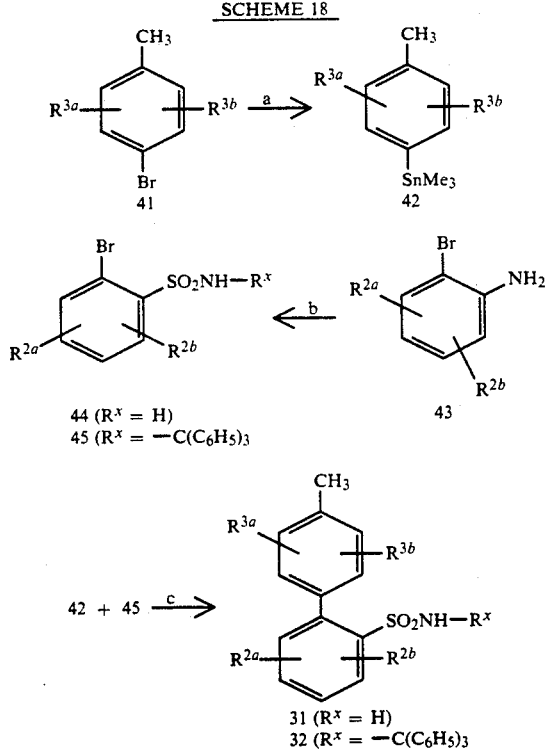

a. (i) t-BuLi/ether, −78° C.
   (ii) Me₃SnCl
b. (i) NaNO₂/HCl
   (ii) SO₂, CuCl₂
   (iii) $R^x$—NH₂
c. Pd(PPh₃)₄, Toluene, Reflux or (PPh₃)₂PdCl₂, DMF, 90° C.

The biaryl sulfonamides 31 and 32 (described in Scheme 16) can be prepared alternatively using palladium(O) catalyzed cross-coupling reactions of appropriate aryl-organotin precursors [J. K. Stille, *Pure Appl. Chem.*, 57, 1771 (1985); T. R. Bailey, *Tet. Lett.*, 27, 4407 (1986); D. A. Widdowson and Y. Z. Zhang, *Tetrahedron*, 42, 2111 (1986)], as outlined in Scheme 18. The organotin compound 42 [S. M. Moerlein, *J. Organometallic Chem.*, 319, 29 (1987)], obtained from the aromatic precursor 41, may be coupled with aryl sulfonamide 44 and 45 using Pd(PPh₃)₄ or (PPh₃)₂PdCl₂ as catalysts to give biaryl sulfonamide 31a and 32 respectively. Similarly, the benzyl bromides 50a and 50b may be alternatively prepared from the appropriate organotin precursor 48 using the Pd(O) catalyzed cross-coupling reaction as outlined in Scheme 19.

SCHEME 19

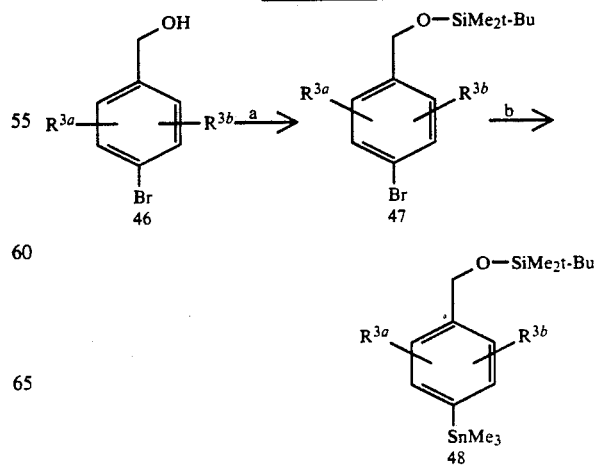

35
-continued
SCHEME 19
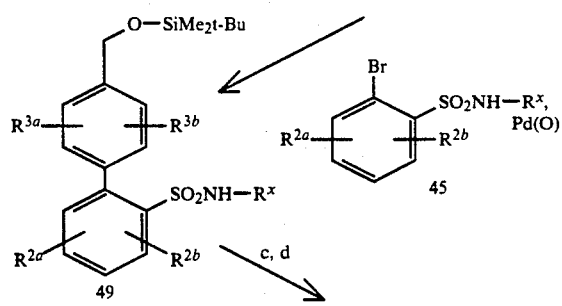
36
-continued
SCHEME 19
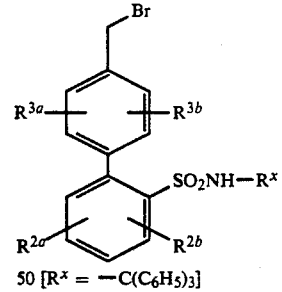
50 [R$^x$ = —C(C$_6$H$_5$)$_3$]
a. t-BuMe$_2$Si—Cl/Imidazole, DMF
b. t-BuLi, −78° C., Me$_3$SnCl
c. Tetrabutylammonium fluoride
d. CBr$_4$/Ph$_3$P.
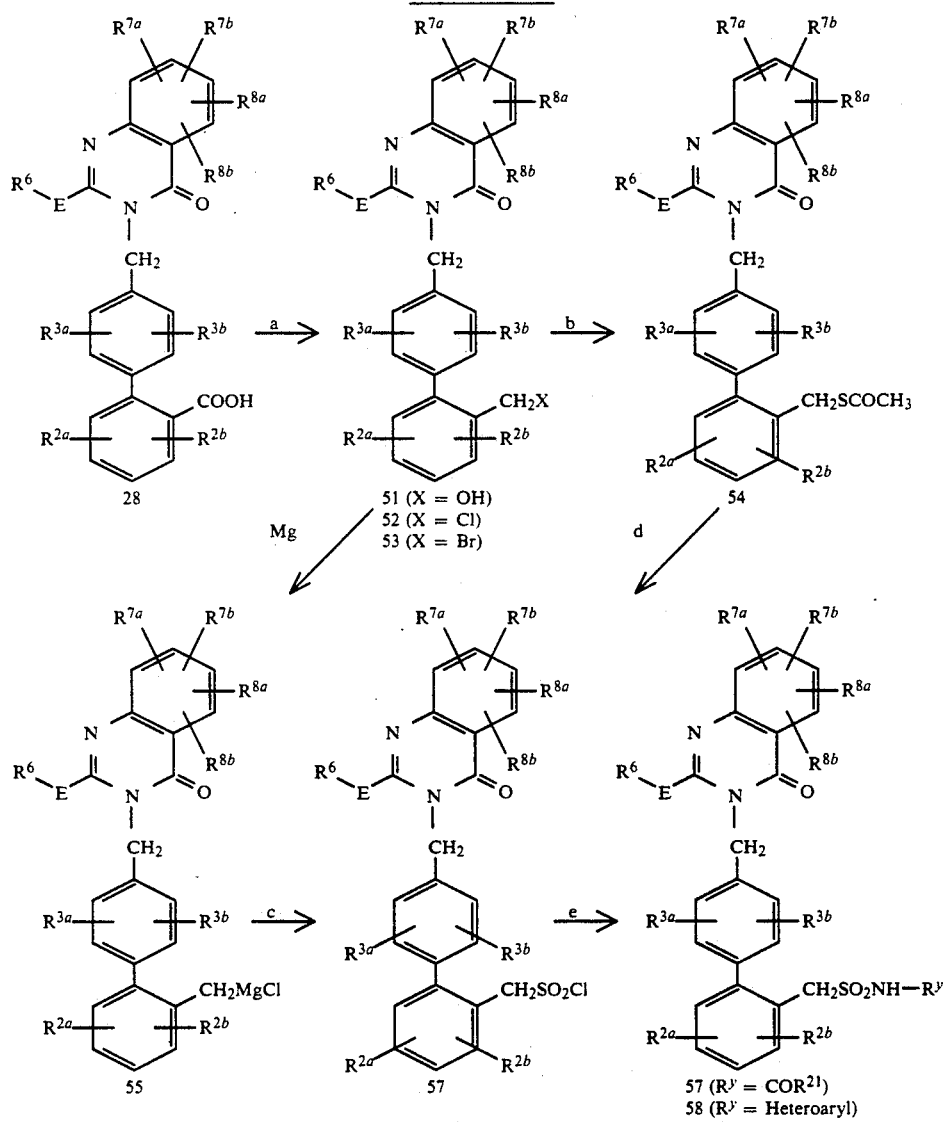
The compounds bearing R$^1$=—CH$_2$SO$_2$NHCOR$^{23}$ and —CH$_2$SO$_2$NHR$^{23}$ may be prepared as outlined in Scheme 20. The key precursor aryl-methanesulfonyl chloride 56 may be prepared either from the reaction of arylmethylmagnesium chloride 55, obtained from the corresponding benzyl chloride 52, with sulfuryl chloride [S. N. Bhattacharya, C. Earborn and D. P. M. Walton, *J. Chem. Soc.* C, 1265 (1968)], or by oxidation of the aryl-methylthioacetate 54 (prepared from the benzyl bromide 53 with chlorine in presence of trace amount of water [Bagnay and Dransch, *Chem. Ber.*, 93, 784 (1960)]. Alternatively, the aryl-methylthioacetate 54 can be oxidized with sulfuryl chloride in presence of acetic anhydride to form arylmethylsulfinyl chloride [S. Thea and G. Cevasco, *Tetra. Lett.*, 28, 5193 (1987)], which can be further oxidized with appropriate oxidizing agents to give the sulfonyl chloride 56. The compounds 57 and 58 can be obtained by reacting the sulfonyl chloride 56 with appropriate amines.

Compounds where $R^1=-NHSO_2NHR^{23}$ may be prepared by the reaction of appropriate primary amines with the sulfamide 60 [S. D. McDermott and W. J. Spillane, *Synthesis*, 192 (1983)], as described in Scheme 21. The compound 60 may be obtained from the corresponding N-t-butylsulfamide 59 after treatment with anhydrous trifluoroacetic acid [J. D. Catt and W. L. Matier, *J. Org. Chem.*, 39, 566 (1974)], which may be prepared by the reaction of the aromatic amine 38 with t-butylsulfamoyl chloride [W. L. Matier, W. T. Comer and D. Deitchman, *J. Med. Chem.*, 15, 538 (1972)].

SCHEME 21

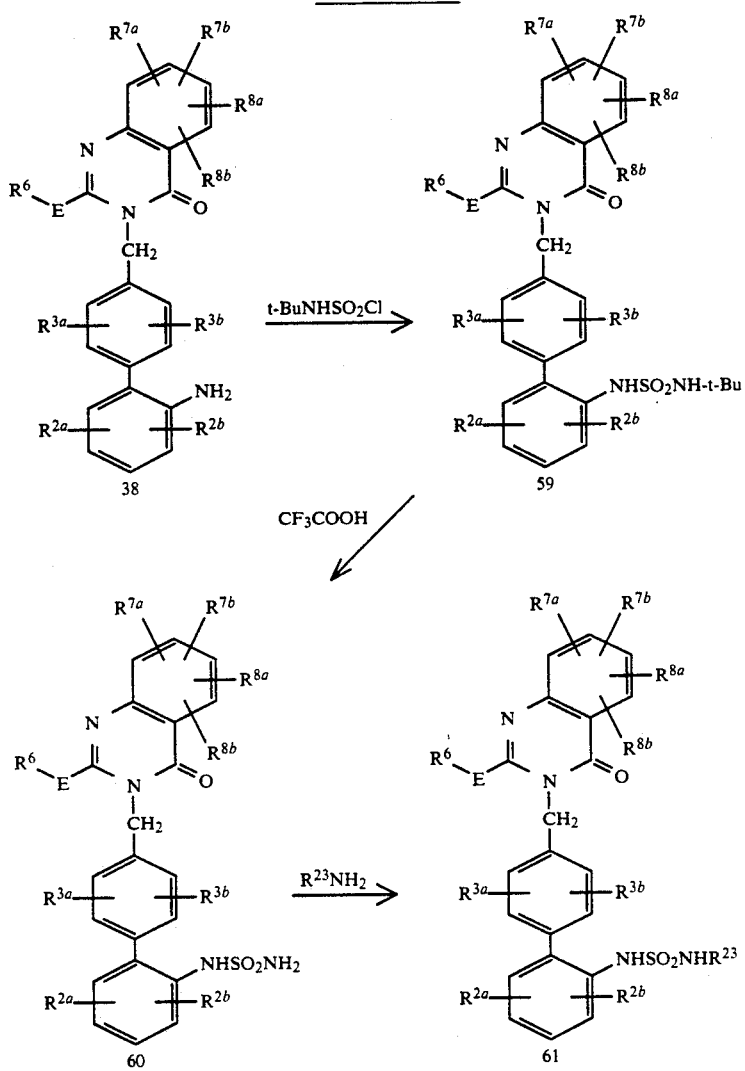

Further functionalization of compounds of Formula 1 where $R^{8a}$ or $R^{8b}$ is nitro is available through the following route (Scheme 22). The nitro group of 62 may be reduced to the amine 63 by reduction with hydrogen over palladium on carbon. The amine may then be acylated with acid chlorides to give amides under basic conditions. The acylation of the amine with chloroformates is best carried out in the presence of sodium hydride to form the anilinium anion. This anion reacts quickly with chloroformates to give the carbamates 64. The amine reacts slowly with isocyanates to give ureas 66. Trisubstituted ureas 67 may be prepared from the benzyl carbamate 64 ($R^{23}$=benzyl) by treatment with the magnesium salt of a secondary amine. The amine may be further derivatized or converted to other groups by means of chemical procedures well known to those skilled in the art.

SCHEME 22

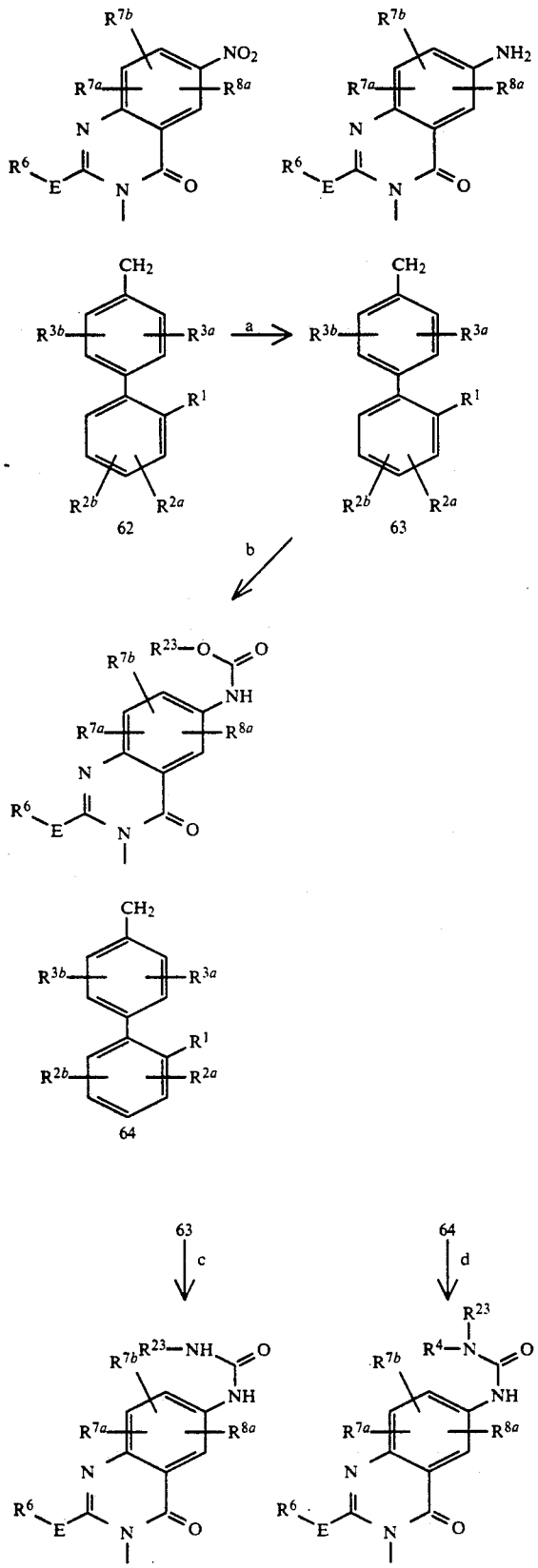

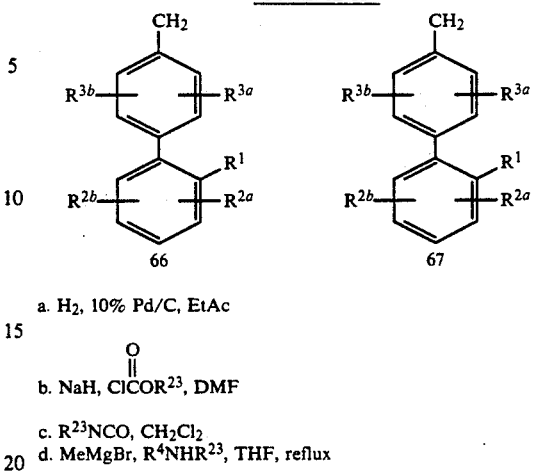

a. H₂, 10% Pd/C, EtAc b. NaH, ClCOR²³, DMF (with C=O)

c. R²³NCO, CH₂Cl₂ d. MeMgBr, R⁴NHR²³, THF, reflux

ADDITIONAL REFERENCES CITED IN SCHEMES

E. C. Taylor, R. J. Knopf, A. L. Borror, *J. Am. Chem. Soc.* (1960) 82, 3152. R. L. McKee, M. K. McKee, R. W. Bost, *J. Am. Chem. Soc.* (1946) 68, 1902. A. Khan, R. K. Saksena, *Pharmazie* (1988) 43H. 12.

M. T. Bogert, W. F. Hand, *J. Am. Chem. Soc.* (1906) 28, 94.

See A. Khan, reference 1. L. A. Errede, J. J. McBrady, H. T. Oien, *J. Org. Chem.* (1977) 42, 656. L. A. Errede, *J. Org. Chem.* (1976) 41 1763. L. A. Errede, H. T. Oien, D. R. Yarian, *J. Org. Chem.* (1977) 42, 12.

K. Wunsch, A. J. Boulton, *Adv. Het. Chem.* (1967) 8, pp 326-9, and references therein. I. R. Gambhir, S. S. Joshi, *J. Ind. Chem. Soc.* (1964) 41, 47.

Bayley, Stranding, Knowles, *Tetrahedron. Lett.* (1978) 3633. Rolla, *J. Org. Chem.* (1982) 47, 4327. Gibson, Bradshaw, *Angew, Chem, Int. Ed. Engl.* (1968) 7, 919.

R. G. Dave, G. S. Mewada, G. C. Amin, *J. Ind. Chem. Soc.* (1960) 37, 595.

J. E. McCarty, E. L. Haines, C. A. VanderWerf, *J. Am. Chem. Soc.* (1960) 82, 964. P. N. Bhargave, P. Ram, *Bull. Chem. Soc. Jap.* (1965) 38, 342. M. R. Chaurasia, A. K. Sharma, *Heterocycles* (1983) 20, 1549. K. Lempert, G. Doleschall, *Chem Ber.* (1963) 96, 1271. H. Singh, K. S. Narang, *J. Ind. Chem. Soc.* (1963) 40, 545. M. S. Dhatt, K. S. Narang, *J. Ind. Chem. Soc.* (1954) 31, 787. M. S. Dhatt, K. S. Narang, *J. Ind. Chem. Soc.* (1954) 31, 864. D. S. Bariana, H. S. Sachdev, K. S. Narang, *J. Ind. Chem. Soc.* (1955) 32, 647. Griess, *Ber. Deut, Chem. Ges.* (1869) 2, 415.

N. A. Lang, F. E. Sheibley, *J. Am. Chem. Soc.* (1933) 55, 1188.

H. B. Milne, S. L. Razniak, R. P. Bayer, D. W. Fish, *J. Am. Chem. Soc.* (1960) 82, 4582. E. J. Corey, M. G. Bock, A. P. Kozikowski, A. V. R. Rao, D. Floyd, B. Lipshutz, *Tetrahedron Lett.* (1978) 1051. M. Bergmann, L. Zervas, *Ber.* (1932) 65 1192.

R. L. Dannley, M. Lukin, *J. Org. Chem.* (1957) 22, 268. R. Zibuck, N. J. Liverton, A. B. Smith, *J. Am. Chem. Soc.* (1986) 10,8 2451.

D. J. Brown, *Fused Pyrimidines*, Part I Quinazolines, (1967), J. Wiley & Sons, p. 222.

D. J. Brown, *Fused Pyrimidines*, Part I Quinazolines, (1967), J. Wiley & Sons, p. 323.

T. W. Greene, *Protective Groups in Organic Synthesis*, (1981), J. Wiley & Sons, pp. 193-217.

It will be appreciated by those skilled in the art that the protecting groups used in these syntheses will be chosen to be compatible with subsequent reaction conditions. Ultimately, they will be removed to generate the active compounds of formula (I). For example, $R^1$ as carboxyl is often protected as its t-butyl ester which in the last step is removed by treatment with trifluoroacetic acid. Aqueous acetic acid employed overnight is a preferred method to remove a trityl protecting group to liberate an $R^1$ tetrazole group.

The compounds of this invention form salts with various inorganic and organic acids and bases which are also within the scope of the invention. Such salts include amminium salts, alkai metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluensulfonic, maleic, fumaric, camphorsulfonic. The nontoxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor binding assay using rabbit aortae membrane preparation:

Three frozen rabbit aortae (obtained from Pel-Freeze Biologicals) were suspended in 5 mM Tris-0.25M Sucrose, pH 7.4 buffer (50 ml) homogenized, and then centifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitracin and the suspension was used for 100 assays tubes. Samples tested for screening were done in duplicate. To the membrane preparation (0.25 ml) there was added $^{125}$I-Sar$^1$Ile$^8$-angiotensin II [obtained from New England Nuclear] (10 μl; 20,000 cpm) with or without the test sample and the mixture was incubated at 37° C. for 90 minutes. The mixture was then diluted with icecold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation (0.5 ml) there was added 3H-angiotensin II (50 mM) (10 μl) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^3$H-angiotensin II was presented as a measure of the efficacy of such compounds as AII antagonists.

The potential antihypertensive effects of the compounds described in the present invention may be evaluated using the methodology described below:

Male Charles River Sprague-Dawley rats (300-375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30-minute intervals and the increase in the diastolic blood pressure was recorded before and after drug or vehicle administration.

Using the methodology described above, representative compounds of the invention were evaluated and were found to exhibit an activity of at least $IC_{50} < 50$ μM thereby demonstrating and confirming the utility of the compounds of the invention as effective AII antagonists.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperplasia, and to minimize the atherosclerotic process. The application of the compound of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensis II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and as such are not to be considered as limiting the invention set forth in the claims appended hereto. All $^1$H-NMR spectra were recorded on a Varian XL-300 Fourier transform spectrometer. Chemical shifts are reported as (parts per million) downfield from tetramethyl silane. Mass spectra were obtained from the Merck and Co. mass spectral facility in Rahway N.J. Analytical TLC was conducted on E. M. Merck precoated silica plates (0.25 mm in glass, Kieselgel 60 F$_{254}$) with UV visualization. All chromatography was conducted on E. M. Merck silica gel. All reactions were carried out under an atmosphere of dry nitrogen under standard conditions for those skilled in the art.

PREPARATION OF BIPHENYL SYNTHETIC INTERMEDIATES

2-t-Butoxycarbonyl-4'-methylbiphenyl

To a solution of p-bromotoluene (30 g) in dry ether (150 ml) at −78° C., a solution of t-BuLi in pentane (1.7M) (210 ml) was added slowly over a period of 1.5 hours, using a dropping funnel. The bath was then removed and the mixture was stirred at room temperature for an additional 2 hours. The content of the flask was then added slowly (using a cannula) at room temperature to a premixed solution of ZnCl$_2$ in ether (1M, 180 ml) and dry THF (360 ml). The mixture was stirred for 2 hours at that temperature and then the slurry was added (using a cannula) to a solution of 2-t-butoxycarbonyl iodobenzene (35.6 g) and NiCl$_2$(Ph$_3$P)$_2$ (2.1 g) in dry THF (360 ml). The mixture, after stirring at room temperature overnight (18 hours), was poured slowly under stirring into ice-cold 0.5N HCl (1500 ml). The organic layer was separated, and the aqueous phase was extracted with ether (3×300 ml). The combined organic layer was washed with water, brine and then dried over MgSO$_4$. Removal of the solvent gave the crude product as an oil (32 g). The material was purified on a silica-gel flash column using ethyl acetate-hexane (1:12) to give the titled compound as an oil (24 g, 76%). $^1$H NMR (CDCl$_3$): δ 1.24 (s,9H), 2.42 (s,3H), 7.2–7.8 (m,8H); FAB-MS: m/e 269(M+H).

4-Bromomethyl-2'-t-butoxycarbonylbiphenyl

To a solution of 2-t-butoxycarbonyl-4'-methylbiphenyl (25.3 g, 95 mmol) in CCl$_4$ (200 ml) were added freshly opened N-bromosuccinimide (17.6 g, 0.099 mole) and dibenzoyl peroxide (2.28 g, 0.0094 moles). the mixture was refluxed for 4 hours, cooled to room temperature and filtered. The filtrate was washed with sat. NaHSO$_3$ (1×50 ml), sat. NaHCO$_3$ (1×50 ml), water (1×50 ml), sat. NaCl (1×50 ml) and dried over MgSO$_4$. The solution was filtered, and concentrated in vacuo. The residue was dissolved in 100 ml of hot hexane. Crystallization gradually took place as the solution cooled. The flask was finally cooled to −20° C. and the precipitate recovered by filtration. The solid was washed with ice cold hexanes and dried in vacuo to give 27 g (88%) of a white solid. $^1$H-NMR (CDCl$_3$): 1.23 (s, 9H), 4.53 (s, 2H), 7.2–7.5 (m, 7H), 7.68 (d, 1H).

2-Cyano-4'-methylbiphenyl

To a solution of p-bromotoluene (30 g) in dry ether (150 ml) at −78° C., a solution of t-BuLi in pentane (1.7M) (210 ml) was added slowly over a period of 1.5 hours, using a dropping funnel. The bath was then removed and the mixture was stirred at room temperature for an additional 2 hours. The contents of the flask was then added slowly (using a cannula) at room temperature to a premixed solution of ZnCl$_2$ in ether (1M) (180 ml) and dry THF (360 ml). The mixture was stirred for 2 hours at that temperature and then the slurry was added (using a cannula) to a solution of 2-bromobenzonitrile (21.3 g) and NiCl$_2$(Ph$_3$P)$_2$ (2.1 g) in dry THF (300 ml). The mixture, after stirring at room temperature overnight (18 hours), was poured slowly under stirring into ice-cold 1N HCl (1500 ml). The organic layer was separated, and the aqueous phase was extracted with ether (3×300 ml). The combined organic layer was washed with water, brine and then dried over MgSO$_4$. Removal of the solvent gave the crude product as a semisolid mass (34 g). The material was purified on a silica-gel flash column using ethyl acetate-hexane (1:12) to give the desired nitrile as a low-melting solid (28 g, 88%). $^1$H-NMR (CDCl$_3$): 2.42 (s, 3H), 7.2–7.8 (m, 8H); FAB-MS: m/e 194 (M+ +1).

Trimethylstannyl azide

To a concentrated solution of NaN$_3$ (1.2 kg, 18.5 moles) in water (3 L), a solution of trimethyltin chloride (600 g, 3 moles) in dioxane (400 ml) was added in three portions under vigorous stirring. A precipitate formed instantaneously. The mixture, after stirring overnight at room temperature, was filtered. The residue was washed with water, and dried under suction and then in vacuo over P$_2$O$_5$. Yield 541 g (88%), mp 120°–122° C.

5-[2-(4'-Methylbiphenyl)]tetrazole

To a solution of 2-cyano-4'-methylbiphenyl (390 g, 2.02 moles) in toluene (2.3 L) was added trimethyltin azide (525 g, 2.55 moles) at room temperature. The mixture was refluxed for 24 hours, cooled to room temperature, filtered, washed with toluene and sucked dry in a funnel. The precipitate was resuspended in toluene (3.5 L) and THF (250 mL) was added. Anhydrous HCl was bubbled in at a moderate rate at room temperature to give a clear solution (45 minutes). Addition of HCl gas was continued for another 20 minutes with stirring whereupon a white precipitate formed. The reaction mixture was stirred overnight. The solid product was filtered, washed with toluene followed with ether and then dried under vacuum. This produced 250 g (53% yield of the tetrazole. m.p. 152°–154° C.; $^1$H-NMR (CDCl$_3$): 2.40 (s, 3H), 7.19 (dd, 1H), 7.55 (m, 2H), 8.25 (dd, 1H).

N-Triphenylmethyl-5-[2-(4'-methylbiphenyl)]tetrazole

To a cloudy solution of 5-[2-(4'-methylbiphenyl)]tetrazole (250 g (1.06 mole) in CH$_2$Cl$_2$ (4 L) was added triphenylmethylchloride (310 g 1.11 mole) at room temperature. The reaction mixture was stirred and triethylamine (190 mL, 138 g, 1.36 mole) was added portionwise. After addition, the mixture was stirred at reflux for 90 minutes. The solution was cooled to room temperature, washed with water (2×1 L)and dried over MgSO$_4$, filtered through a silica gel plug and concentrated on the rotovap to a solid. This was crystallized from toluene to give the product as an off-white solid (425 g, 84%); m.p. 166°–168° C.; $^1$H-NMR (CDCl$_3$): 2.28 (s, 3H), 6.9–7.05 (m, 10H), 7.2–7.5 (m, 12H), 7.9 (dd, 1H).

N-Triphenylmethyl-5-[2-(4'-bromomethylbiphenyl)]tetrazole

To a solution of N-triphenylmethyl-5-[2-(4'-methylbiphenyl)]tetrazole (425 g, 0.89 moles) in CCl$_4$ (4.0 L) were added N-bromsuccinimide (159 g, 0.89 mole) and dibenzoyl peroxide (22 g, 0.089 moles). The mixture was refluxed for 2 hours, cooled to room temperature and filtered. The filtrate was concentrated in vacuo to give a thick oil. The addition of ether (2.0 L) to this oil resulted in a clear solution followed by crystallization, filtration gave a white solid (367 g, 74%). m.p.

137°–139.5° C.; $^1$H-NMR (CDCl$_3$): 4.38 (s, 2H), 6.9–8.0 (m, 23H).

N-Triphenylmethyl-5-[2-(4'-aminomethylbiphenyl)]-tetrazole

To a suspension of 11.15 g (22 mmol) of N-triphenylmethyl-5-[2-(4'-bromomethylbiphenyl)]-tetrazole in 55 mL of dry DMSO was added 1.23 g (25 mmol) of LiN$_3$. The mixture gradually cleared and was replaced by a new white precipitate. The mixture was stirred for 6 hours and filtered. The precipitate was washed with 50 mL of water. Some additional precipitate formed in the mixed filtrate; this was refiltered and the residue washed with 30 mL of MeOH and 100 mL of water. The solid product was dried in vacuo overnight. The crude azide (9.89 g, 20.8 mmol) was dissolved in 50 ml of dry THF and treated with 5.73 g (22 mmol) of triphenylphosphine portionwise. N$_2$ evolution was observed during the addition. After 4 hours the solution was treated with 0.63 mL (34 mmol) of water and stirred over night. The solution was concentrated in vacuo and the residue purified by flash chromatography over silica gel eluting with 95:5:0.01 CHCl$_3$:MeOH:NH$_4$OH. 6.83 g (15.4 mmol) of a white solid was recovered, 69% overall yield. $^1$H-NMR (CDCl$_3$): 3.74 (s, 2H), 6.88 (m, 5H), 7.06 (q, 4H, J=8.1 Hz), 7.22–7.52 (m, 13H), 7.95 (m, 1H).

Preparation of Additional Functionalized Biphenyls

Preparation of:
N-Triphenyl-5-(4'-bromomethyl-4chlorobiphen-2-yl)tetrazole

Step 1: 2-Cyano-4'-methyl-4-nitrobiphenyl

To a solution of p-tolyltrimethyltin (389 mg, 1.525 mmol) in dry toluene (5 mL) under N$_2$ was added 2-bromo-5-nitro-benzonitrile (276 mg, 1.22 mmol) and Pd(PPh$_3$)$_4$ (176 mg; 10 mol %). The reaction was stirred at reflux under N$_2$ for 24 hours and then cooled to room temperature. The mixture was diluted with EtOAc and the solid was removed by filtration through a pad of celite. The filtrate was concentrated in vacuo and the residue was purified by flash chromatography on a silica column eluting with Hex/EtOAc (10:1) to afford 214 mg (74%) of the titled compound as a slightly yellow solid. $^1$H-NMR: (300 MHz, CDCl$_3$) δ 2.42 (s, 3H), 7.32 (d, 2H), 7.48 (d, 2H), 7.69 (d, 1H), 8.45 (dd, 1H), 8.61 (s, 1H).

Step 2: N-Triphenylmethyl-5-(4'-methyl-4-nitrobiphen-2-yl)tetrazole

The titled compound was prepared starting from 2-cyano-4-nitro-4'-methylbiphenyl (Step 1) according to procedures described in European Patent Application EP 0,291,969. $^1$H-NMR: (300 MHz, CDCl$_3$) δ 2.28 (s, 3H), 6.89 (d, 6H), 6.98 (ABq, 4H), 7.22–7.37 (comp, 9H), 7.56 (d, 1H), 8.31 (dd, 1H), 8.75 (d, 1H).

Step 3: N-Triphenylmethyl-5-(4-chloro-4'-methylbiphen-2-yl)tetrazole

A solution of N-triphenylmethyl-5-(4'-methyl-4-nitrobiphen-2-yl)tetrazole (0.115 g, 0.224 mmol) in MeOH/DMF (2 mL/12 mL) was submitted to hydrogenation at 40 psi H$_2$ with 10% Pd on carbon (50 mg) at room temperature for 1 hour. The reaction was filtered through celite and the filtrate was concentrated in vacuo. The triphenyl methyl group had been lost during the hydrogenation. The crude 4-amino compound was dissolved in glacial acetic acid (3 mL) and added slowly to a cooled (0° C.) solution of NaNO$_2$ (28.8 mg, 0.417 mmol) in conc. sulfuric acid (1 mL). The diazonium solution was stirred well for 2 hours then slowly added to a cooled (0° C.) solution of CuCl (0.449 g; 20 equiv) in conc. HCl. This mixture was stirred for 30 minutes and then poured over H$_2$O and extracted with Et$_2$O/EtOAc. The combined organic extracts were washed with H$_2$O and brine, dried over MgSO$_4$ and concentrated in vacuo. The product was purified by flash chromatography on a silica column eluting with Hex/EtOAc/HOAc (80:20;1) to afford 27 mg (45% for 2 steps) of 5-(4-chloro-4'-methyl-biphen-2-yl)tetrazole. The free tetrazole was dissolved in CH$_2$Cl$_2$ (3.5 mL) and NEt$_3$(0.035 mL, 2.5 equiv) and Ph$_3$CCl (27 mg, 1.0 equiv) were added. After 30 minutes the reaction was diluted with Et$_2$O washed with 10% citric acid, 1N NaOH and brine. The organic was dried over anhydrous MgSO$_4$ and concentrated in vacuo to afford 51.2 mg (100%) of crude N-triphenylmethyl-5-(4-chloro-4'-methyl-biphen-2-yl)tetrazole. $^1$H NMR (300 MHz, CDCl$_3$) δ 2.26 (s, 3H), 6.91 (d, 6H), 6.94 (ABq, 4H), 7.20–7.25 (comp, 7H), 7.43 (dd, 1H), 7 99 (dd, 1H).

Step 4: N-Triphenylmethyl-5-(4'-bromomethyl-4-chlorobiphen-2-yl)tetrazole

The titled compound was prepared starting from N-triphenylmethyl-5-(4-chloro-4'-methyl-biphen-2-yl)tetrazole (step 1 to 3) according to procedures described in European Patent Application EP 0,291,969.

Preparation of: 4-Bromomethyl-2'-nitrobiphenyl

Step 1: 4-Methyl-2'-nitrobiphenyl

A 1 L three-necked 24/40 round-bottom flask equipped with a mechanical stirrer, a 250 mL constant pressure addition funnel with a nitrogen inlet at the top, and a septum was flame dried, cooled and then charged with a solution of 29.07 g (0.17 mol) of p-bromotoluene in 100 mL of anhydrous tetrahydrofuran under a nitrogen atmosphere. The solution was stirred and cooled to −78° C. and 200 mL (0.34 mol) of a 1.7M solution of t-butyllithium in pentane was added via the addition funnel over 30 minutes. When the addition was complete, the cooling bath was removed and the reaction mixture was stirred for 30 minutes and allowed to warm to room temperature. The dropping funnel was next charged with 170 mL (0.17 mol) of a 1.0M solution of zinc chloride in diethylether which was added to the reaction mixture over a 10 minute period. A separate 1 L three-necked 24/40 round-bottom flask equipped with a mechanical stirrer, a nitrogen inlet and a septum, was flame dried, cooled and then charged with 4.04 g (6.0 mmol) of bis(triphenylphosphine)palladium(II) chloride and 50 mL of anhydrous tetrahydrofuran under a nitrogen atmosphere. The stirrer was started and 8.0 mL of a 1.5M solution (12 mmol) of diisobutylaluminum hydride in toluene was added to the suspension via syringe. The catalyst was stirred an additional 10 minutes at room temperature, and then a solution of 23.23 g (0.115 mol) of 1-bromo-2-nitrobenzene in 100 mL of anhydrous tetrahydrofuran was added. The suspension of the tolylzinc chloride was then transferred to the second flask via a wide diameter cannula. The reaction mixture was stirred an additional 45 minutes at room temperature, then most of the tetrahydrofuran was removed on a rotary evaporator. The resulting oil was partitioned between ethyl acetate and 1.0N hydrochloric acid. The organic layer was washed successively with water and brine, then dried (MgSO$_4$), filtered and evaporated. The residual oil was purified on a silica gel flash chromatography column eluted with 10% ethyl acetate-hexane to afford after evaporation and drying in vacuo 15.43 g (63%) of the product as a viscous yellow oil: $^1$H-NMR (CDCl$_3$): δ 2.36 (s, 3H), 7.16-7.24 (m, 4H), 7.38-7.46 (m, 2H), 7.55-7.62 (m, 1H), 7.80 (d, J=10 Hz, 1H); MS (FAB) m/e 214 (MH+).

Step 2: 4-Bromomethyl-2'-nitrobiphenyl

A 2 L 24/40 three necked round-bottom flask equipped with a mechanical stirrer, a reflux condenser and a stopper, was charged with 15.427 g (72 mmol) of 4-methyl-2'-nitro[1,1'-biphenyl], 1.2 L of carbon tetrachloride, 14.164 g (80 mmol) of N-bromosuccinimide, and 0.50 g of 2,2'-azobis-(2-methylpropionitrile). The stirred reaction mixture was refluxed under a nitrogen atmosphere for 4 hours, then cooled to room temperature and filtered. The filtrate was evaporated in vacuo and the residual oil was purified on a silica gel flash chromatography column eluted with 10% ethyl acetate-hexane. Evaporation of the pure fractions afforded the product as a yellow crystalline solid (7.83 g, 37%) which had: mp 109°-110° C.; $^1$H-NMR (CDCl$_3$): δ 4.52 (s, 2H), 7.24-7.30 (m, 2H), 7.40-7.52 (m, 4H), 7.58-7.65 (m, 1H), 7.86 (d, J=10 Hz, 1H); MS (FAB) m/e 294 (MH+).

Preparation of
N-Triphenylmethyl-5-(4-fluoro-4'-bromomethyl-biphen-2-yl)tetrazole Step 1: 2-cyano-4-fluoro-4'-methylbiphenyl A solution of p-tolyltrimethyltin (1.26 g; 4.96 mmol) in dry toluene (8 mL) was degassed with a stream of N$_2$ for ca. 5 min. To this solution under N$_2$ was added 2-bromo-5-fluoro-benzonitrile (0.901 g; 4.51 mmol) and Pd(PPh$_3$)$_4$ (260 mg; 5 mol %). The reaction was stirred at reflux under N$_2$ for 12 hr and then cooled to room temperature. The reaction mixture was filtered through a pad of celite and the filtrate was concentrated in vacuo. The product was purified by flash chromatography on a silica column eluting with Hex/CH$_2$Cl$_2$ to afford 0.606 g (64%) of the title compound as a slightly yellow solid. $^1$H-NMR (300 MHz, CDCl$_3$) δ 2.40 (s, 3H), 7.28 (d, 2H), 7.34 (dd, 1H), 7.40 (d, 2H), 7.44 (t, 1H), 7.46 (dd, 1H); FAB mass spectrum, m/e 211 (m+, calcd for C$_{14}$H$_{10}$NF, 211).

Step 2: N-Triphenylmethyl-5-(4-fluoro-4'-methylbiphen-2-yl)tetrazole

The titled compound was prepared starting from 2-cyano-4-fluoro-4'-methylbiphenyl (step 1) according to procedures described in European Patent Application EP 0,291,969.

Step 3: N-Triphenylmethyl-5-(4-fluoro-4'-bromomethyl-biphen-2-yl)tetrazole

To a solution of N-Triphenylmethyl-5-(4-fluoro-4'-methyl-biphen-2-yl)tetrazole (454.4 mg; 0.9161 mmol) in dry CCl$_4$ (8 mL) was added N-bromosuccinimide (179.2 mg; 1.1 eq) and a catalytic amount of AIBN. The reaction was heated to reflux (105°-115°) under N$_2$. After 3 hrs. the reaction was cooled and filtered through a cotton plugged pipet to remove the succinimide formed. The solvent was removed and replaced by EtOAc/Et$_2$O. The reaction was washed with 1N NaOH and brine. The organic solution was dried over anhydrous MgSO$_4$, filtered, and concentrated in vacuo to afford the product. The crude product was used in the next reaction.

PREPARATION OF
2-ALKYL-QUINAZOLIN-4(1H)-ONES

EXAMPLE 1

2-Butyl-6-methylquinazolin-4(1H)-one

To a solution of 3.0 g (20 mmol) of 2-amino-5-methylbenzoic acid in 20 mL of dry DMF at 0° C. was added 200 mg of DMAP followed by 6.07 g (60 mmol) of triethyl amine and 5.02 g (40 mmol) of valeryl chloride. The resulting mixture was stirred at 0° C. for 30 minutes. The mixture was heated to 110° C. and monitored by TLC for the formation of the intermediate quinoxazolone (rf=0.8, 40% EtOAc/hexane). Following complete formation of the intermediate 10 g (100 mmol) of NH$_4$CO$_3$ was added cautiously. Heating was continued to ensure consumption of the quinoxazolone and formation of the polar (rf=0.4, 40% EtOAc/hexane) quinazolin-4(1H)-one. The reaction mixture was concentrated in vacuo and the residue was taken up in 50 mL of ether and 50 mL of water. The mixture was filtered and the filtrate discarded after washing the residue with 20 mL of ether. The residue was recrystalized from MeOH to give 1.07 g (5 mmol) of a white crystaline solid. 25% yield overall. $^1$H-NMR (CDCl$_3$): 0.94 (t, 3H, J=6.7 Hz), 1.50 (m, 2H), 1.83 (m, 2H), 2.49 (s, 3H), 2.78 (t, 2H), 7.60 (m, 2H), 8.05 (m, 1H). Anal (C$_{13}$H$_{16}$N$_2$O), C, H, N.

EXAMPLE 2

6-Methyl-2-propylquinazoline-4(1H)-one

The 2-propyl derivative was prepared in the identical fashion as the 2-butyl derivative through the use of butyryl chloride in place of valeryl chloride. The product was recrystallized from hexane/acetone to give white crystals. 32% yield. $^1$H-NMR (CDCl$_3$): 11.51 (bs, 1H), 8.08 (s, 1H), 7.60 (s, 2H), 2.78 (3 line m, 2H), 2.01 (s, 3H), 1.92 (m, 2H), 1.09 (t, 3H).

EXAMPLE 3

2-Butyl-7-methylquinazoline-4(1H)-one

Same procedure as in Example 1 with valeroyl chloride and 2-amino-4-methylbenzoic acid. The product was recrystallized from MeOH recovering 0.91 g (4.2 mmol). 21% yield overall. $^1$H-NMR (CDCl$_3$): 0.99 (t, 3H, J=7.4 Hz), 1.49 (m, 2H), 1.86 (m, 2H), 2.50 (s, 3H), 2.76 (t, 2H, J=7.81 Hz), 7.28 (d, 1H, J=8.3 Hz), 7.49 (s, 1H), 8.15 (d, 1H, J=8.3 Hz). Anal (C$_{13}$H$_{16}$N$_2$O), C, H, N.

EXAMPLE 4

2-Butyl-naphtho[2,3-e]quinazoline-4(1H)-one

Same procedure as in Example 1 with valeroyl chloride and 2-aminonapthoic acid. Product was recrystallized from MeOH. A contaminant co-crystallizes with the desired product. The contaminant is 25% of the product by $^1$H-NMR. Recovered 1.6 g (59% yield). $^1$H-NMR (CDCl$_3$): 0.97 (t, 3H, J=7.3 Hz), 1.42 (m, 2H), 1.75 (m, 2H), 2.48 (t, 2H, J=7.4 Hz), 7.42 (t, 1H, J=7.8 Hz), 7.54 (t, 1H, J=8.3 Hz), 7.77 (d, 1H, J=7.8 Hz), 7.82 (d, 1H, J=8.31 Hz), 8.07 (s, 1H), 9.08 (s, 1H), 10.89 (bs, 1H).

EXAMPLE 5

2-Butyl-5-methylquinazoline-4(1H)-one

Same procedure as in Example 1 with valeroyl chloride and 2-amino-6-methylbenzoic acid on a 16 mmol scale. The concentrated reaction mixture was diluted with 50 mL ether and 50 mL H$_2$O. The mixture was agitated for several minutes and then filtered in vacuo. On filtration further crystalline material formed in the filtrate. The filtrate was filtered again. This procedure was repeated a further two times. The precipitates were collected and combined. The ethereal phase was decanted from the aqueous phase, and concentrated to 15 mL. 25 mL of hexanes was then added and the mixture filtered. The combined precipitates were recrystallized from MeOH/H$_2$O to give 0.73 g (3.37 mmol) of fluffy white crystals. 21% yield. $^1$H-NMR (CDCl$_3$): 0.98 (t, 3H, J=7.38 Hz), 1.48 (m, 2H), 1.87 (m, 2H), 2.75 (dd, 2H, J=8.09 Hz), 2.89 (s, 3H), 7.20 (d, 1H, J=6.73 Hz), 7.56 (m, 2H), 11.68 (bs, 1H).

EXAMPLE 6

2-Butyl-6,8-dimethylquinazoline-4(1H)-one

Same procedure as in Example 1 with valeroyl chloride and 2-amino-5,8-dimethylbenzoic acid on a 12 mmol scale. The product collected from filtration of the ether/water mixture was recrystalized from MeOH. $^1$H-NMR and TLC indicated that the product isolated was a 50% mixture of the desired quinazoline and a contaminant. An aliquot of 0.5 g of this material was concentrated onto 5 mL of flash silica and applied to the surface of a flash chromatography column. The column was eluted with 60% EtOAc/hexanes. The first eluted compound (0.14 g) was collected as a TLC homogeneous sample of the desired product. $^1$H-NMR (CDCl$_3$): 0.99 (t, 3H, J=7.32 Hz), 1.48 (m, 2H), 1.85 (m, 2H), 2.44 (s, 3H), 2.58 (s, 3H), 2.75 (dd, 2H, J=7.87,7.87 Hz), 7.43 (s, 1H), 7.91 (s, 1H), 10.70 (bs, 1H).

EXAMPLE 7

2-Butyl-8-methylquinazoline-4(1H)-one

Same procedure as in Example 1 with valeroyl chloride and 2-amino-6-methylbenzoic acid on a 1 mmol scale. The concentrated reaction mixture was diluted with 20 mL ether/20 mL H$_2$O. The mixture was filtered. The ethereal phase was seperated, dried (MgSO$_4$), filtered and concentrated. The residue was flash chromatographed over silica eluting with 50% EtOAc/hexanes to give rise to 48 mg (0.22 mmol) of a fluffy yellow solid. 22% yield. $^1$H-NMR (CDCl$_3$): 1.02 (t, 3H), 1.52 (m, 2H), 1.88 (m, 2H), 2.62 (s, 3H), 2.79 (dd, 2H), 7.35 (dd, 1H), 7.61 (d, 1H), 8.12 (d, 1H). FABMS: 217 (M$^+$+1) calc for C$_{13}$H$_{16}$N$_2$O.

EXAMPLE 8

2-Butyl-6-isopropylquinazolin-4(1H)-one

Same procedure as in Example 1 with valeroyl chloride and 2-amino-5-isopropylbenzoic acid on a 16 mmol scale. The concentrated reaction mixture was partitioned between 20 mL water and 20 mL of ether. A fine white precipitate was removed by filtration and recrystallized from MeOH/water. The first crop gave rise to 0.56 g of fluffy white crystals. $^1$H-NMR (CDCl$_3$): 0.99 (t, 3H, J=7.3 Hz), 1.32 (d, 6H, J=6.89 Hz), 1.48 (m, 2H), 1.85 (m, 2H), 2.77 (3 line m, 2H, J=7.9 Hz), 3.06 (m, 1H), 7.65 (m, 2H), 8.11 (s, 1H), 11.22 (bs, 1H). FABMS: 245 (M$^+$+1) calc for C$_{15}$H$_{20}$N$_2$O.

EXAMPLE 9

2-Butyl-6-thiomethylquinazolin-4(1H)-one

Same procedure as that described in Example 1. However on addition of ether/water to the reaction mixture a precipitate of the quinazolinone was not formed. The aqueous phase was extracted with ether and the combined ethereal extracts were washed with brine and dried over MgSO$_4$. The mixture was filtered and concentrated in vacuo to give a mixture of the desired product and 2-(N-valeroyl-amino)-5-thiomethylbenzamide. This mixture was heated with 2 equivalents of 1N NaOH solution in water at 100° C. until a clear solution was obtained. The solution was cooled, acidified, and filtered to give a pale yellow precipitate. The product was recrystalized from MeOH to give a 73% overall yield of the title compound. $^1$H-NMR (CDCl$_3$-300 MHz): 1.00 (t, 3H, J=7.3 Hz), 1.50 (m, 2H), 1.86 (m, 2H), 2.58 (s, 3H), 2.76 (3 line m, 2H, J=7.9 Hz), 7.62 (m, 2H), 8.03 (d, 1H, J=1.9 Hz), 11.11 (bs, 1H).

EXAMPLE 10

2-Butyl-6-nitroquinazolin-4(1H)-one

To a mixture of 326 mg (2 mmol) of 2-cyano-4-nitroaniline in 10 mL of CH$_2$Cl$_2$ at 0° C. was added 0.34 mL (2.4 mmol) of triethylamine and 25 mg of DMAP. To this mixture was added 0.26 ml of valeryl chloride dropwise. The reaction mixture was allowed to warm to room temperature over 1.5 hours and then concentrated in vacuo. The residue was dissolved in 40 ml of EtOAc and washed with 25 ml of water, 25 ml of saturated NaHCO$_3$ and 25 ml of brine. The organic phase was dried over Na$_2$SO$_4$, filtered and concentrated. The residue (0.46 g) was purified by flash chromatography. The residue was absorbed onto 0.6 g of silica which was applied to the surface of a 5.5"×0.75" silica flash chromatography column. The product was eluted with 20% EtOAc/hexanes to give 0.21 g of N-valeryl-2-cyano-4-nitro-anilide (44% yield). 0.1 g (0.42 mmol) of the amide was dissolved in 1.5 mL of MeOH. To this solution was added 138 μL of a 30% hydrogen peroxide solution followed by 330 μL of a 3N NaOH solution. The solution was refluxed for 1.5 hours, cooled and concentrated in vacuo. The residue was dissolved in 10 mL of water. Dropwise addition of a saturated solution of NH$_4$Cl caused the product to precipitate out as 90 mg (0.36 mmol) of a yellow powder. (87% yield. $^1$H-NMR (CDCl$_3$): 1.02 (t, 3H, J=7.32 Hz), 1.52 (m, 2H), 1.90 (m, 2H), 2.82 (dd, 2H, J=8.03 Hz), 7.82 (d, 1H, J=9.01 Hz), 8.56 (dd, 1H, J=2.6, 8.9 Hz), 9.14 (d, 1H, J=2.71 Hz).

EXAMPLE 11

2-Butylquinazolin-4(1H)-one

To a solution of 500 mg 2-aminobenzonitrile (4.23 mmol), 514 mg triethylamine (5.08 mmol), and 50 mg DMAP (0.41 mmol) in 6 mL CH$_2$Cl$_2$ at 0° C. was added 562 mg valeryl chloride (4.66 mmol) dropwise over 1 minute. The mixture was warmed to room temperature and stirred for twenty minutes. The mixture was then diluted with water and brine and then was extracted three times with ether. The combined organic material was dried over MgSO$_4$, stripped of solvent in vacuo, and was purified by flash chromatography eluting with 20% ethyl acetate in hexane to give 2-valerylamidobenzonitrile. $R_f$ 0.22 in 20% ethyl acetate in hexane. $^1$H-NMR (300 MHz, CDCl$_3$): 8.42 (d, 1H), 7.60–7.10 (m, 2H), 6.72 (m, 1H), 4.40 (br s, 1H), 2.46 (t, 2H), 1.74 (m, 2H), 1.43 (m, 2H), 0.97 (t, 3H).

To a solution of 5.1 g of the amide in 90 mL methanol were added 21 mL 3N NaOH and 10 ml 30% H$_2$O$_2$ at room temperature. The mixture was refluxed for 30 minutes and concentrated in vacuo. Water and sat. NH$_4$Cl was added and the mixture extracted 3 times with ether. The combined organic extracts were dried over MgSO$_4$, filtered and concentrated in vacuo and the residue was recrystallized from hexane/acetone to give two crops of the product as white needles. 2.2 g, 43% yield. $R_f$ 0.16 in 20% EtOAc in CH$_2$Cl$_2$. $^1$H-NMR (CDCl$_3$): 8.29 (m, 1H), 7.81–7.68 (m, 2H), 7.47 (m, 1H), 2.79 (3 line m, 2H), 1.87 (m, 2H), 1.51 (m, 2H), 1.00 (t, 1H).

EXAMPLE 12

6-Bromomethyl-2-butylquinazolin-4(1H)-one

To a suspension of 2.6 g (12 mmol) of the product of Example 2 in 100 mL of dry CCl$_4$ was added 2.56 g of N-bromosuccinimide followed by 200 mg of benzoyl peroxide. The reaction mixture was heated to reflux for 45 minutes at which time a precipitate formed throughout. The reaction mixture was concentrated in vacuo and the residue partitioned between 150 mL of EtOAc and 100 mL of water. The mixture was shaken and then filtered to give 1.59 g of the title compound (45% yield). The filtrate was seperated into two phases and the organic phases was washed with 75 mL of sat. NaHCO$_3$ solution followed by 75 mL of water and 75 mL of brine. The organic phase was dried over MgSO$_4$, filtered and the filtrate was concentrated in vacuo. The residue was purified by recrystalization from EtOAc to give 0.52 g (1.76 mmol) of the same product as was recovered above. Total yield 60%. $^1$H-NMR (CDCl$_3$): 1.00 (t, 3H, J=7.33 Hz), 1.49 (m, 2H), 1.84 (m, 2H), 2.77 (3 line m, 2H, J=7.7 Hz), 4.61 (s, 2H), 7.68 (d, 1H, J=8.4 Hz), 7.80 (dd, 1H, J=8.4, 2.1 Hz), 8.27 (d, 1H, J=2.1 Hz), 11.02 (bs, 1H).

EXAMPLE 13

5-Bromomethyl-2-butylquinazolin-4(1H)-one

The product of Example 5 was treated as in Example 13 to give a 71% yield of a white solid. $^1$H-NMR (CDCl$_3$): 1.0 (t, 3H, J=7.3 Hz), 1.53 (m, 2H), 2.90 (m, 2H), 2.81 (3 line m, 2H, J=7.98 Hz), 5.31 (s, 2H), 7.45 (m, 1H), 7.71 (m, 2H), 11.28 (bs, 1H).

EXAMPLE 14

6-Acetoxymethyl-2-butylquinazolin-4(1H)-one

To a solution of 2.1 g (7.0 mmol) of the quinazolinone prepared in Example 12 in 15 mL of dry DMF was added 1.74 g (20.0 mmol) of sodium acetate. The mixture was heated to 60° C. for 3 hours. The reaction mixture was concentrated in vacuo and the residue dissolved in 100 mL of CH$_2$Cl$_2$. The solution was washed with water (3×20 mL), brine (1×20 mL) and dried over MgSO$_4$. The mixture was filtered and concentrated in vacuo. The residue was recrystallized from MeOH/H$_2$O to give 1.31 g (4.8 mmol) of a colorless solid. 68% yield. $^1$H-NMR (CDCl$_3$): 0.99 (t, 3H, J=7.32 Hz), 1.50 (m, 2H), 1.83 (m, 2H), 2.14 (t, 3H), 2.77 (3 line m, 2H, J=7.71 Hz), 5.23 (s, 2H), 7.69–7.78 (m, 2H), 8.25 (s, 1H), 10.90 (bs, 2H).

EXAMPLE 15

5-Acetoxymethyl-2-butylquinazolin-4(1H)-one

The product of Example 13 was treated as in Example 14 to give after recrystallization from EtOAc a 77% yield of the desired acetylated product. $^1$H-NMR (CDCl$_3$): 0.98 (t, 3H, J=7.38 Hz), 1.50 (m, 2H), 1.88 (m, 2H), 2.19 (s, 3H), 2.77 (3 line m, 2H, J=7.93 Hz), 5.85 (s, 2H), 7.48 (m, 1H), 7.70 (m, 2H), 11.65 (bs, 1H).

EXAMPLE 16

6-Nitro-2-propylquinazolin-4(1H)-one

To a solution of 16.3 g (0.1 mol) of 2-amino-5-nitrobenzonitrile in 200 ml of CH$_2$Cl$_2$ at 0° C. was added 21 ml (0.15 mol) of triethyl amine followed by 0.3 g of DMAP and 11.71 g (0.11 mol) of butyryl chloride. The reaction mixture was warmed to room temperature and then heated over night at 50° C. The solution was washed with 1N HCl (1×20 ml), water (1×20 ml), saturated NaHCO$_3$ (2×20 ml) and brine (1×20 ml) and dried over MgSO$_4$. The solution was filtered and concentrated in vacuo. The residue was dissolved in 200 ml of MeOH to which was added 44 ml (0.22 mol) of 5M NaOH solution followed by the dropwise addition of 25 ml (0.22 mol) 30% H$_2$O$_2$ and 50 ml of water. The mixture was refuxed for 4 hours, cooled and filtered. The filtrate was acidified with 1N HCl and the resulting precipitate recovered by filtration. The residue was recrystalized from MeOH to give 8.3 g (0.036 mol) of pale brown fluffy cystals. 36% yield. $^1$H-NMR (CDCl$_3$): 1.10 (t, 3H, J=7.4 Hz), 1.93 (m, 2H), 2.79 (3 line m, 2H, J=7.3 Hz), 7.80 (d, 1H, J=8.9 Hz), 8.55 (dd, 1H, J=2.5, 8.8 Hz), 9.14 (bs, 1H).

PREPARATION OF 3-N-ALKYL-2-ALKYLQUINAZOLIN-4(3H)-ONES

A general procedure for the synthesis of 3-N-akylated-quinazolin-4(3H)-ones is given below. Chromatography conditions, yields, and spectral data are given for the compounds prepared by this procedure.

A suspension of 1.1 mmol of NaH in 2 mL of dry DMF at 0° C. under nitrogen was treated with 1 mmol of the quinazolin-4(1H)-one as a solid (most quinazolin-4(1H)-ones prepared were insoluble in DMF). Immediate evolution of hydrogen could be observed as the quinazolin-4(1H)-one was deprotonated and dissolved. After 30 minutes the solution was warmed to room temperature for a further 30 minutes. To this solution cooled to 0° C. was added a solution of 1 mmol of either 4-bromomethyl-2'-t-butoxycarbonylbiphenyl, 4-bromomethyl-2'-cyano-biphenyl or N-triphenylmethyl-5-[2-(4'-bromomethylbiphenyl)] tetrazole in 1.5 mL of DMF. After 30 minutes, the reaction mixture was warmed to room temperature and stirred overnight. The solution was concentrated in vacuo, and the residue dissolved in 50 mL of EtOAc. The solution was washed with water (3×10 mL) and brine (2×10 mL). The organic phase was dried over MgSO$_4$, filtered and concentrated in vacuo. The residue was purified as indicated below:

EXAMPLE 17

2-Butyl-3-[(2'-(t-butoxycarbonyl)biphen-4-yl)methyl]-quinazolin-4(3H)-one

The quinazolinone prepared as described in Example 11 was alkylated with 4-bromomethyl-2'-t-butoxycarbonyl-biphenyl. The product was purified by flash chromatography over silica gel eluting with 1% EtOAc/methylene chloride. $^1$H-NMR (300 MHz, CDCl$_3$): 8.32 (m, 1H), 7.76 (m, 2H), 7.46 (m, 2H), 7.38 (m, 1H), 7.32–7.18(m, 5H), 5.46 (bs, 2H), 2.79 (3 line m, 2H), 1.80 (m, 2H), 1.44 (m, 2H), 1.23 (s, 9H), 0.95 (t, 3H).

EXAMPLE 18

2-Butyl-3-[(2'-(cyano)biphen-4-yl)methyl]quinazolin-4(3H)-one

The quinazolinone prepared as described in Example 11 was alkylated with 4-bromomethyl-2'-cyanobiphenyl. The product was purified by MPLC Lobar C silica column eluting with 25% EtOAc/hexane. R$_f$ 0.13 in 30% EtOAc/hexane. $^1$H-NMR (300 MHz, CDCl$_3$): 8.32 (m, 1H), 7.84–7.59 (m, 7H), 5.46 (bs, 2H), 2.79 (3 line m, 2H), 1.80 (m, 2H), 1.44 (m, 2H), 0.94 (t, 3H).

EXAMPLE 19

2-Butyl-3-[(2'-(t-butoxycarbonyl)biphen-4-yl)methyl]-8-methylquinazolin-4(3H)-one The quinazolinone prepared as described in Example 7 was alkylated with 4-bromomethyl-2'-t-butoxycarbonyl-biphenyl. The product was purified by flash chromatography over silica eluting 12.5% EtOAc/hexane. 58% yield. $^1$H-NMR (CDCl$_3$): 0.95 (t, 3H, J=7.3 Hz), 1.23 (s, 9H), 1.44 (m, 2H), 1.85 (m, 2H), 2.62 (s, 3H), 2.79 (dd, 2H, J=7.65, 7.65 Hz), 5.45 (bs, 2H), 7.20–7.50 (m, 8H), 7.59 (dd, 1H, J=1.1, 8.47 Hz), 7.77 (dd, 1H, J=1.6, 7.7 Hz), 8.16 (dd, 1H, J=1.2, 7.7 Hz). FABMS, 483 (M$^+$+1).

EXAMPLE 20

2-Butyl-3-[(2'-(t-butoxycarbonyl)biphen-4-yl)methyl]-6-methylquinazolin-4(3H)-one The quinazolinone prepared as described in Example 1 was alkylated with 4-bromomethyl-2'-t-butoxycarbonyl-biphenyl. The product was purified by flash chromatography over silica gel eluting with 15% EtOAc/hexane, 43% yield. $^1$H-NMR (CDCl$_3$): 0.95 (t, 3H, J=7.3 Hz), 1.23 (s, 9H), 1.43 (m,2H), 1.79 (m, 2H), 2.49 (s, 3H), 2.77 (dd, 2H, J=8.0, 8.0 Hz), 5.46 (bs, 1H), 7.19–7.60 (m, 10H), 7.77 (dd, 1H, J=1.6, 7.6 Hz). FABMS, 483 (M$^+$+1).

EXAMPLE 21

2-Butyl-3-[(2'-(t-butoxycarbonyl)biphen-4-yl)methyl]-6-nitroquinazolin-4(3H)-one The quinazolinone prepared as described in Example 10 was alkylated with 4-bromomethyl-2'-t-butoxycarbonylbiphenyl. The product was purified by flash chromatography over silica gel eluting with 20% EtOAc/hexane, 48% yield. $^1$H-NMR (CDCl$_3$): 0.96 (t, 3H, J=7.38 Hz), 1.25 (s, 9H), 1.45 (m, 2H), 1.83 (m, 2H), 2.84 (dd, 2H, J=8.08 Hz), 5.47 (bs, 2H), 7.20–7.50 (m, 8H), 7.78 (d, 1H, J=9.07 Hz), 8.53 (dd, 1H, J=2.5, 8.8 Hz), 9.18 (d, 1H, J=2.5 Hz). FABMS, m/z 514 (M$^+$+1).

EXAMPLE 22

2-Butyl-3-[(2'-cyanobiphen-4-yl)-methyl]-6-methyl-quinazolin-4(3H)-one

The quinazolinone prepared as described in Example 1 was alkylated with 4-bromomethyl-2'-cyanobiphenyl. The product was purified by MPLC Lobar C silica gel column eluting with 20% EtOAc/hexane, 61% yield. $^1$H-NMR (CDCl$_3$): 0.92 (t, 3H, J=7.5 Hz), 1.42 (m, 2H), 1.77 (m, 2H), 2.48 (s, 3H), 2.77 (dd, 1H, J=8.0, 8.0 Hz), 5.46 (bs, 3H), 7.30 (d, 1H, J=7.9 Hz), 7.40–7.65 (m, 7H), 7.74 (d, 1H, J=7.9 Hz), Hz), 8.09 (s, 1H).

EXAMPLE 23

2-Butyl-3-[(2'-(t-butoxycarbonyl)biphen-4-yl)methyl]-7-methylquinazolin-4(3H)-one The quinazolinone prepared as described in Example 3 was alkylated with 4-bromomethyl-2'-t-butoxycarbonylbiphenyl. The product was purified by flash chromatography over silica eluting with 20% EtOAc/hexane, 62% yield. $^1$H-NMR (CDCl$_3$): 0.95 (t, 3H, J=7.33 Hz), 1.23 (s, 9H), 1.42 (m, 2H), 1.79 (m, 2H), 2.50 (s, 3H), 2.77 (dd, 2H, J=7.9, 7.9 Hz), 5.44 (bs, 2H), 7.20–7.51 (m, 9H), 7.76 (dd, 1H, J=1.31, 7.71 Hz), 8.19 (d, 1H, J=8.13 Hz). Anal (C$_{31}$H$_{34}$N$_2$O$_3$), C, H, N.

EXAMPLE 24

2-Butyl-3-[(2'-(t-butoxycarbonyl)biphen-4-yl)methyl]-naphtho[2,3-e]quinazolin-4(3H)-one The quinazolinone prepared as described in Example 4 was alkylated with 4-bromomethyl-2'-t-butoxycarbonyl-biphenyl. The product was purified by MPLC Lobar B silica gel column eluting with 15% EtOAc/hexane, 3.6% yield (note: low yield due to inseparable side product in starting quinazoline). $^1$H-NMR (CDCl$_3$): 0.97 (t, 3H, J=7.27 Hz), 1.24 (s, 9H), 1.46 (m, 2H), 1.85 (m, 2H), 2.82 (dd, 2H, J=8.2, 8.2 Hz), 5.49 (bs, 1H), 7.2–7.61 (m, 9H), 7.76 (d, 1H, J=7.1 Hz), 7.97 (d, 1H, J=8.6 Hz), 8.06 (d, 1H, J=7.9 Hz), 8.17 (s, 1H), 8.94 (s, 1H).

EXAMPLE 25

2-Butyl-3-[(2'-(t-butoxycarbonyl)biphen-4-yl)methyl]-6,8-dimethylquinazolin-4(3H)-one The quinazolinone prepared as described in Example 6 was alkylated with 4-bromomethyl-2'-t-butoxycarbonyl-biphenyl. The product was purified by MPLC Lobar B silica column eluting with 17% EtOAc/hexane, 47% yield. $^1$H-NMR (CDCl$_3$): 0.95 (t, 3H, J=7.2 Hz), 1.23 (s, 9H), 1.42 (m, 2H), 1.83 (m, 2H), 2.43 (s, 3H), 2.58 (s, 3H), 2.77 (dd, 2H, J=7.7 Hz), 5.44 (bs, 2H), 7.19–7.48 (m, 8H), 7.76 (d, 1H, J=6.2 Hz), 7.95 (s, 1H).

EXAMPLE 26

2-Propyl-3-[(2'-(cyano)biphen-4-yl)methyl]-6-methyl-quinazolin-4(3H)-one

The quinazolinone prepared as described in Example 2 was alkylated with 4-bromomethyl-2-cyanobiphenyl. The product was purified by MPLC Lobar C silica column eluting with 30% EtOAc/hexane, 34% yield. $^1$H-NMR (CDCl$_3$): 8.10 (s, 1H), 7.79–7.25 (m, 10H), 5.49 (bs, 2H), 2.76 (3 line m, 2H), 2.49 (s, 3H), 1.84 (m, 2H), 1.02 (t, 3H, J=7.4 Hz).

EXAMPLE 27

2-Butyl-3-[2'-(t-butoxycarbonyl)biphen-4-yl-methyl]-5-methylquinazolin-4(3H)-one The quinazolinone prepared as described in Example 5 was alkylated with 4-bromomethyl-2'-t-butoxycarbonyl-biphenyl. The product was purified by MPLC Lobar B silica column eluting with 17% EtOAc/hexane. $^1$H-NMR (CDCl$_3$): 0.95 (t, 3H, J=7.3 Hz), 1.22 (s, 9H), 1.43 (m, 2H), 1.79 (m, 2H), 2.76 (dd, 2H, J=7.7, 7.7

Hz), 2.87 (s, 3H), 5.40 (bs, 2H), 7.18–7.59 (m, 10H), 7.77 (dd, 1H, J=1.4, 7.4 Hz).

EXAMPLE 28

6-Isopropyl-2-butyl-3-[(2'-(N-triphenylmethyltetrazol-5-yl)biphen-4-yl)methyl]quinazolin-4(3H)-one The quinazolinone prepared as described in Example 8 was alkylated with N-triphenylmethyl-5-[2-(4'-bromomethylbiphenyl)]tetrazole in the same general manner as above. The product was purified by MPLC Lobar silica column to give a colorless oil, 51% yield. $^1$H-NMR (CDCl$_3$): 0.89 (t, 3H, J=7.27 Hz), 1.33 (d, 6H, J=6.9 Hz), 1.34 (m, 2H), 1.71 (m, 2H), 2.66 (3 line m, 2H, J=7.6 Hz), 3.08 (m, 1H), 5.31 (bs, 2H), 6.90–7.51 (m, 23H), 7.65 (m, 1H), 7.93 (dd, 1H, J=2.7, 7.0 Hz), 8.17 (bs, 2H). FABMS m/z 721 (M$^+$+1) calc. for C$_{48}$H$_{44}$N$_8$O.

EXAMPLE 29

6-Nitro-2-butyl-3-[(2'-(N-triphenylmethyl-tetrazol-5-yl)biphen-4-yl)methyl]quinazolin-4(3H)-one The quinazolinone prepared as described in Example 10 was alkylated with N-triphenylmethyl-5-[2-(4'-bromomethylbiphenyl)]tetrazole in the same general manner as above. The product was purified by flash chromatography over silica gel eluting with 50% CH$_2$Cl$_2$/hexanes and gradually increasing the proportion of EtOAc to 15%, 37% yield. $^1$H-NMR (CDCl$_3$ 300 MHz): 0.90 (t, 3H, J=7.5 Hz), 1.35 (m, 2H), 1.72 (m, 2H), 2.72 (3 line m, 2H, 7.9 Hz), 5.31 (bs, 2H), 6.89–7.00 (m, 8H), 7.12 (d, 2H, J=8.0 Hz), 7.23–7.37 (m, 11H), 7.48 (m, 2H), 7.77 (d, 1H, J=9.0 Hz), 7.92 (m, 1H), 8.53 (dd, 1H, J=2.7, 9.1 Hz), 9.18 (d, 1H, J=2.6 Hz).

EXAMPLE 29B

6-Nitro-2-propyl-3-[(2'-(N-triphenylmethyl-tetrazol-5-yl)biphen-4-yl)methyl]quinazolin-4(3H)-one The quinazolinone prepared as described in Example 16 was alkylated with N-triphenylmethyl-5-[2-(4'-bromomethylbiphenyl)]tetrazole in the general manner as described above. The product was purified by trituration with 50% EtOAc/hexanes to give a 50–70% yield of the desired product. $^1$H-NMR (CDCl$_3$): 0.96 (t, 3H, J=7.4 Hz), 1.78 (m, 2H), 2.69 (3 line m, 2H, J=7.5 Hz), 5.30 (bs, 2H), 6.82–6.98 (m, 6H), 7.11 (d, 2H, J=8.0 Hz), 7.20–7.32 (m, 12H), 7.45 (m, 2H), 7.77 (d, 1H, J=9.0 Hz), 7.93 (dd, 1H, J=6.8, 2.2 Hz), 8.53 (dd, 1H, J=9.0, 2.7 Hz), 9.18 (d, 1H, J=2.6 Hz).

EXAMPLE 30

2-Butyl-3-[(2'-(N-triphenylmethyl-tetrazol-5-yl)biphen-4-yl)methyl]-6-thiomethylquinazolin-4(3H)-one The product of Example 9 was alkylated with N-triphenylmethyl-5-[2-(4'-bromomethylbiphenyl)]tetrazole following the general protocol described above. The product was purified by flash chromatography over silica gel eluting with 20%EtOAc/hexane, 51% yield. $^1$H-NMR (CDCl$_3$ 300 MHz): 0.89 (t, 3H), 1.33 (m, 2H), 1.71 (m, 2H), 2.58 (s, 3H), 2.62 (3 line m, 2H), 5.28 (bs, 2H), 6.85–6.98 (m, 8H), 7.08 (d, 2H), 7.18–7.36 (m, 10H), 7.43 (m, 2H), 7.60 (m, 2H), 7.91 (dd, 1H), 8.07 (d, 1H).

EXAMPLE 31

2-Butyl-3-(4'-fluoro-2'-(N-triphenylmethyltetrazol-5-yl)biphen-4-yl)methyl-6-isopropylquinazolin-4(3H)-one To a solution of 2-butyl-6-isopropylquinazolinone (55.6 mg; 0.228 mmol) (Example 8) in dry DMF (1.5 mL) was added NaH, 80% oil dispersion, (11.8 mg; 1.5 eq). The reaction mixture was allowed to stir for 30 min. under N$_2$. To this was added a solution of N-triphenylmethyl-5-(4-fluoro-4'-bromomethyl-biphen-2-yl)tetrazole (crude) in dry DMF (1.5 mL). The reaction was stirred under N$_2$ for 3 hrs. then quenched with saturated NH$_4$Cl solution. The solvent was removed at high vacuum, replaced by EtOAc, and the insoluable salts filtered off. The product was purified by flash chromatography on a silica column eluting with Hex/EtOAc (35:1) to afford 94.5 mg (56%) of the titled compound. Characteristic peaks $^1$H-NMR (300 MHz, CDCl$_3$) δ 0.87 (t, 3H), 1.30 (d, 6H), 1.68 (m, 2H), 2.63 (t, 2H), 3.05 (q, 1H), 5.28 (s, 2H), 8.13 (s, 1H).

EXAMPLE 32

2-Butyl-6-methyl-3-[(2'-nitrobiphen-4-yl)methyl]-quinazolinone

To a solution of 0.111 g (0.51 mmol) of 2-butyl-6-methylquinazolinone in 4.0 mL of dimethylformamide was added 0.022 g of a 60% oil dispersion of sodium hydride and the resulting mixture was stirred at room temperature under a nitrogen atmosphere. After 30 min hydrogen evolution had ceased, and 0.150 g (0.51 mmol) of 4-bromomethyl-2'-nitrobiphenyl was added to the reaction mixture. Stirring was continued for 2 h at room temperature and then the reaction mixture was partitioned between ethyl acetate and water. The organic layer was extracted, washed with water, brine, then dried (MgSO$_4$), filtered and evaporated. The residual oil was purified on a silica gel flash chromatography column eluted with 25% ethyl acetate-hexane to afford 0.129 g (59%) of the product as a colorless oil which had: $^1$H-NMR (CDCl$_3$) δ 0.91 (t, J=10 Hz, 3H), 1.34–1.47 (m, 2H), 1.69–1.80 (m, 2H), 2.46 (s, 3H), 2.74 (t, J=11 Hz, 2H), 5.43 (s, 2H), 7.18–7.28 (m, 4H), 7.36 (d, J=12 Hz, 1H), 7.45 (t, J=12 Hz, 1H), 7.52–7.62 (m, 3H), 7.83 (d, J=12 Hz, 1H), 8.08 (s, 1H); MS (FAB) m/e 428 (MH$^+$).

EXAMPLE 33

3-[(2'-Aminobiphen-4-yl)methyl]-2-butyl-6-methyl-quinazolin-4(3H)-one

To a solution of 0.127 g (0.30 mmol) of 2-butyl-6-methyl-3-[(2'-nitrobiphen-4-yl)methyl]quinazolinone, from Example 32, in 15 mL of absolute ethanol was added 0.030 g of a 10% palladium on powdered charcoal catalyst and the resulting mixture was hydrogenated under a 35 psig hydrogen atmosphere in a Parr apparatus. After 1 h TLC analysis (50% ethyl acetate-hexane) of the reaction mixture indicated complete reduction. The mixture was filtered, evaporated and dried in vacuo to afford 0.114 g (97%) of a viscous oil which was used directly in the next step without further purification: $^1$H-NMR (CDCl$_3$) δ 0.91 (t, J=10 Hz, 3H), 1.36–1.47 (m, 2H), 1.70–1.82 (m, 2H), 2.47 (s, 3H), 2.77 (t, J=11 Hz, 2H), 3.72 (br s, 2H), 5.44 (s, 2H), 6.70–6.83 (m, 2H), 7.04–7.16 (m, 2H), 7.23 (d, J=14 Hz, 2H), 7.39 (d, J=14 Hz, 2H), 7.56 (s, 2H), 8.08 (s, 1H); MS (FAB) m/e 398 (MH$^+$).

EXAMPLE 34

2-Butyl-6-methyl-3-[(2'-trifluoromethylsulfonamidobiphen-4-yl)-methyl]quinazolin-4(3H)-one To a solution of 0.114 g (0.29 mmol) of the product of Example 33 in 3.0 mL of dichloromethane was added 0.074 g (0.36 mmol) of 2,6-di-tert-butyl-4-methylpyridine and the reaction was stirred at room temperature under a nitrogen atmosphere. Trifluoromethanesulfonic anhydride (0.101 g, 0.36 mmol) was added at once via syringe and the reaction mixture was stirred for 1 hr at room temperature. The reaction mixture was then partitioned between dichloromethane and water and the organic layer was extracted. The organic layer was washed with 1.0N hydrochloric acid, water, dried ($MgSO_4$), filtered and evaporated. The residual oil was purified on a silica gel flash chromatography column eluted with 25% ethyl acetate-hexane. Evaporation of the purified fractions and drying in vacuo afforded 0.049 g (32%) of an off white amorphous solid which had: $^1$H-NMR (CDCl$_3$) δ 0.91 (t, J=10 Hz, 3H), 1.37-1.48 (m, 2H), 1.74-1.85 (m, 2H), 2.46 (s, 3H), 2.75 (t, J=11 Hz, 2H), 5.44 (s, 2H), 6.61 (br s, 1H), 7.21-7.32 (m, 7H), 7.54-7.64 (m, 3H), 8.08 (s, 1H); MS (FAB) m/e 530 (MH+).

EXAMPLE 35

6-Acetoxymethyl-2-butyl-3-[(2'-(N-triphenylmethyltetrazol-5-yl)biphen-4-yl)methyl]quinazolin-4-(3H)-one To a solution of 0.8 g (2.9 mmol) of the product of Example 14 in 30 mL of dry DMF at 0° C. was added 6.13 g (3.0 mmol) of a 0.5M solution of potassium hexamethyl disilazide in toluene. The reaction mixture was stirred for 30 minutes and then treated with a solution of 1.54 g (3.0 mmol) of N-triphenylmethyl-5-[2-(4'-bromomethylbiphenyl)] tetrazole in 6 mL of DMF. The reaction mixture was stirred for 6 hours while allowing the temperature to rise to 25° C. The solution was taken up in 100 mL of EtOAc and washed with water (3×20 mL) and brine (1×20 mL) and dried over MgSO$_4$. The mixture was filtered and concentrated in vacuo and the residue was purified by flash chromatography over silica eluting with 25% EtOAc/hexanes to give 0.71 g of a white foam, 33% yield. $^1$H-NMR (CDCl$_3$): 0.89 (t, 3H, J=7.3 Hz), 1.32 (m, 2H), 1.71 (m, 2H), 2.13 (s, 3H), 2.66 (3 line m, 2H, 7.7 Hz), 5.23 (s, 2H), 5.30 (bs, 2H), 6.88-6.95 (m, 8H), 7.10 (d, 2H, J=8.2 Hz), 7.21-7.35 (m, 11H), 7.46 (m, 2H), 7.71 (m, 2H), 7.92 (m, 1H).

EXAMPLE 36A

5-Acetoxymethyl-2-butyl-3-[(2'-(N-triphenylmethyltetrazol-5-yl)biphen-4-yl)methyl]quinazolin-4(3H)-one The product of Example 15 was alkylated with N-triphenylmethyl-5-[2-(4'-bromomethylbiphenyl)]tetrazole following the method described in Example 30 to give a 57% yield of the title compound. $^1$H-NMR (CDCl$_3$): 0.99 (t, 3H, J=7.0 Hz), 1.32 (m, 2H), 1.71 (m, 2H), 2.18 (s, 3H), 2.64 (3 line m, 2H, J=7.3 Hz), 5.25 (bs, 2H), 5.85 (s, 2H), 6.89-6.97 (m, 8H), 7.10 (d, 2H, 6.2 Hz), 7.22-7.35 (m, 11H), 7.45 (m, 2H), 7.68 (m, 2H), 7.92 (m, 1H).

EXAMPLE 36B

2-Butyl-3-[2'-(t-butoxycarbonyl)biphen-4-yl)methyl]-6-isopropylquinazolin-4(3H)-one To a suspension of sodium hydride (0.034 g of 50% oil suspension) in dry DMF (5 ml) was added 2-n-butyl-6-isopropylquinazolin-4-one (prepared as described in Example 8) (0.2 g, 0.76 mmol) and stirred at room temperature for 1.5 hours. At this stage, 4-bromomethyl-2'-t-butoxycarbonylbiphenyl (0.29 g, 0.77 mMol) was added, and the mixture was stirred at room temperature for 18 hours. The crude product isolated, after work-up as described in the general procedure for alkylation of quinazolin-4(3H)-ones was purified by flash chromatography over silica-gel using methylene chloride containing 1% methanol to give the desired compound as white amorphous solid (0.23 g, 67%). $^1$H-NMR(CDCl$_3$): 0.97 (t 3H, J=7.35 Hz), 1.19 (s, 9H), 1.31 (d, 6H, J=6.9 Hz, 1.45 (m, 2H), 1.81 (m, 2H, 2.95 (t, 2H, J=7.7 Hz), 3.07 (m, 1H), 5.69 (s, 2H), 7.33-7.94 (m, 11H). FAB-MS: m/e 455 (M+H), 909 (2M+H).

ALTERNATIVE PREPARATION OF 2-BUTYL-3-[(2'-(N-TRIPHENYLMETHYL-TETRAZOL-YL)-BIPHEN-4-YL)METHYL]ALKYL-QUINAZOLIN-4(3H)-ONES IN A SINGLE POT REACTION FROM ANTHRANILIC ACIDS

EXAMPLE 37

2-Butyl-7-chloro-3-[(2'-(N-triphenylmethyl-tetrazol-5-yl)biphen-4-yl)methyl]quinazolin-4(3H)-one To 0.17 g (1.0 mmol) of 2-amino-4-chlorobenzoic acid in 1 ml of dry pyridine under N$_2$ was added 0.24 g (2.0 mmol) of valeroyl chloride. The solution was heated for 5 hours. TLC (40% EtOAc/hexanes indicated formation of a non-polar intermediate. To this solution was added 0.45 g (1.0 mmol) of N-triphenylmethyl-5-[2-(4'-aminomethylbiphenyl)]tetrazole and the solution was heated at 120° C. overnight. The solution was taken up in 30 ml of EtOAc and 10 ml of water. The organic phase was washed with water (3×10 ml), sat. NaHCO$_3$ (2×10 ml) and sat. NaCl (1×10 ml). The organic phase was dried over MgSO$_4$, filtered and concentrated in vacuo. The residue was purified by flash chromatography over silica eluting with 20% EtOAc/hexanes to give 0.153 g of an oil, 21% yield. $^1$H-NMR (CDCl$_3$): 0.89 (t, 3H, J=7.4 Hz), 1.32 (m, 2H), 1.69 (m, 2H), 2.65 (3 line m, 2H, J=7.7 Hz), 5.28 (bs, 2H), 6.83-7.50 (m, 23H), 7.69 (d, 1H, J=1.95 Hz), 7.92 (dd, 1H, J=2.22, 6.78 Hz), 8.23 (d, 1H, J=8.52 Hz). FABMS m/z 713 (M++1) calc. for C$_{45}$H$_{37}$N$_6$OCl.

EXAMPLE 38

2-Butyl-6-ethyl-3-[(2'-(N-triphenylmethyl-tetrazol-5-yl)biphen-4-yl)methyl]quinazolin-4(3H)-one As in the procedure described above for Example 37. Purification by flash chromatography eluting with 20% EtOAc/hexane to give a pale yellow oil, 16% yield. $^1$H-NMR (CDCl$_3$): 0.89 (t, 3H, J=7.4 Hz), 1.32 (t, 3H, J=7.5 Hz), 1.3-1.4 (m, 2H), 1.72 (m, 2H), 2.67 (3 line m, 2H), 2.80 (q, 2H, J=7.5 Hz), 5.32 (bs, 2H), 6.90-7.5 (m, 22H), 7.63 (s, 2H), 7.94 (dd, 1H, J=1.5,6.9 Hz), 8.16 (bs, 1H).

FURTHER TRANSFORMATIONS OF-3-N-ALKYL-QUINAZOLIN-4(3H)-ONES BEFORE REMOVAL OF PROTECTING GROUPS

EXAMPLE 39

6-Amino-2-butyl-3-[(2'-(t-butoxycarbonyl)biphen-4-yl)methyl]quinazolin-4(3H)-one 0.11 g (0.21 mmol) of 2-butyl-3-[(2'-(t-butoxycarbonyl)biphen-4-yl)methyl]-6-nitroquinazolin-3(1H)-one (Example 21) was suspended in 7.5 mL of MeOH and hydrogenated over 55 mg of 10% Pd/C under an atmospheric pressure hydrogen blanket. After 1 hour the reaction mixture was filtered through celite and the filtrate concentrated in vacuo. The residue was purified by flash chromatography over silica gel eluting with 50% EtOAc/hexane to give 69 mg (0.14 mmol) of a white foam, 67% yield. $^1$H-NMR (CDCl$_3$): 0.94 (t, 3H, J=7. Hz), 1.23 (s, 9H), 1.41 (m, 2H), 1.79 (m, 2H), 2.74 (3 line m, 2H, J=7.7 Hz), 5.44 (bs, 2H), 7.05-7.57 (m, 10H), 7.77 (d, J=7.5 Hz).

EXAMPLE 40

6-Amino-2-butyl-3-[(2'-(N-triphenylmethyl-tetrazol-5-yl)biphen-4-yl)methyl]quinazolin-4(3H)-one A solution of 3.2 g (4.4 mmol) of the 6-nitroquinazolinone from Example 29 in 100 mL of EtOAc was hydrogenated over night under atmospheric pressure in the presence of 0.5 g of 10% Pd/C. The solution was filtered through celite and the celite was washed with CH$_2$Cl$_2$ to remove any of the yellow coloured product. The filtrate was concentrated in vacuo to give 3.0 g of a pale yellow solid. The material was not purified further, 98% yield. $^1$H-NMR (CDCl$_3$ 300 MHz): 0.89 (t, 3H, J=7.3 Hz), 1.32 (m, 2H), 1.69 (m, 2H), 2.62 (3 line m, 2H, J=7.9 Hz), 4.00 (bs, 2H), 5.29 (bs, 2H), 6.88-7.02 (m, 6H), 7.08-7.15 (m, 4H), 7.22-7.38 (m, 11H), 7.45-7.55 (m, 4H), 7.93 (dd, 1H, J=2.5, 7.0 Hz).

EXAMPLE 41

6-Amino-2-propyl-3-[(2'-(N-triphenylmethyl-tetrazol-5-yl)biphen-4-yl)methyl]quinazolin-4(3H)-one The product of Example 29B was hydrogenated as described in Example 40. The product was purified by flash chromatography over silica gel eluting with 7% Acetone/CH$_2$Cl$_2$ to give a pale yellow solid. 72% yield. $^1$H-NMR (CDCl$_3$): 0.92 (m, 3H, J=7.4 Hz), 1.72 (m, 2H), 2.58 (3 line m, 2H, J=7.7 Hz), 5.56 (bs, 2H), 6.82-7.51 (m, 25H), 7.92 (dd, 1H, J=6.9, 1.9 Hz).

EXAMPLE 42

6-Acetamido-2-butyl-3-[(2'-(N-triphenylmethyl-tetrazol-5-yl)biphen-4-yl)methyl]quinazolin-4(3H)-one To a solution of 0.12 g (0.17 mmol) of the aminoquinazolinone from Example 40 in 2 mL of CH$_2$Cl$_2$ was added 33 mg (0.32 mmol) of triethylamine followed by 10 mg of dimethylaminopyridine. The reaction mixture was cooled to 0° C. and treated with 14 mg (0.19 mmol) of acetyl chloride. The solution was allowed to warm to room temperature at which time a further 0.3 equivalents of acetyl chloride was added and the mixture was stirred overnight. The reaction mixture was concentrated in vacuo and the residue was purified by flash chromatography over silica gel eluting with 50% EtOAc/hexanes containing a gradually increasing concentration of CH$_2$Cl$_2$ to 10% to give 0.073 g of the title compound, 57% yield. $^1$H-NMR (CDCl$_3$ 250 MHz): 0.88 (t, 3H, J=7.08 Hz), 1.32 (m, 2H), 1.70 (m, 2H), 2.19 (s, 3H), 2.64 (3 line m, 2H, J=7.2 Hz), 5.30 (bs, 2H), 6.89-6.98 (m, 8H), 7.09 (d, 2H, J=8.1 Hz), 7.20-7.35 (m, 10H), 7.46 (m, 2H), 7.66 (d, 1H, J=8.8 Hz), 7.73 (bs, 1H), 7.92 (m, 1H), 8.14 (d, 1H, J=8.8, 2.3 Hz).

EXAMPLE 43

2-Butyl-3-[(2'-(N-triphenylmethyl-tetrazol-5-yl)biphen-4-yl)methyl]-6-valeroylamidoquinazolin-4(3H)-one The product of Example 40 was acylated with valeroyl chloride in the same manner as that described in Example 42. The product was purified by flash chromatography over silica gel eluting with 30% EtOAc/hexanes and increasing the concentration of EtOAc to 50% to give an oil, 65% yield. $^1$H-NMR (CDCl$_3$ 300 MHz): 0.87 (t, 3H, J=7.3 Hz), 0.93 (t, 3H, J=7.3 Hz), 1.25-1.45 (m, 4H), 1.72 (m, 4H), 2.38 (t, 2H, J=7.7 Hz), 2.62 (3 line m, 2H, J=7.9 Hz), 5.28 (bs, 2H), 6.91 (m, 8H), 7.08 (d, 2H, J=8.2 Hz), 7.20-7.35 (m, 11H), 7.45 (m, 2H), 7.64 (d, 1H, J=8.9 Hz), 7.73 (bs, 1H), 7.91 (dd, 1H, J=2.6,6.9 Hz), 8.12 (d, 1H, J=2.4 Hz), 8.27 (bd, 1H, J=8.8 Hz).

EXAMPLE 44

2-Butyl-6-(N-carbobenzyloxy)amino-3-[(2'-(N-triphenylmethyl-tetrazol-5-yl)biphen-4-yl)methyl]-quinazolin-4(3H)-one To a suspension of 4 mg (0.12 mmol) of 80% NaH in oil in 1 mL of dry DMF under nitrogen was added at 0° C. a solution of 69 mg (0.1 mmol) of the 6-aminoquinazoline from Example 40. A bright blue solution was formed. After 0.5 hours 18.8 mg (0.1 mmol) of benzylchloroformate was added via syringe. The blue colour rapidly dissipated and the reaction mixture was stirred for 3 hours while allowing the temperature to rise to room temperature. The reaction mixture was concentrated in vacuo and the residue was dissolved in 25 mL of EtOAc and 5 mL of water. The aqueous phase was extracted with EtOAc (2×5 mL) and the combined organic phases were washed with water (1×5 mL) and brine (1×5 mL) and dried over MgSO$_4$. The mixture was filtered and concentrated in vacuo and the residue was purified by flash chromatography over silica gel eluting with 30% EtOAc/hexane to give 51.7 mg (0.62 mmol), 62% yield. $^1$H-NMR (CDCl$_3$ 300 MHz): 0.88 (t, 3H, J=7.3 Hz), 1.32 (m, 2H), 1.68 (m, 2H), 2.60 (3 line m, 2H, J=8.41 Hz), 5.19 (s, 2H), 5.29 (bs, 2H), 6.90 (m, 8H), 7.09 (d, 1H, J=8.2 Hz), 7.2-7.52 (m, 18H), 7.65 (d, 1H, J=8.8 Hz), 7.91 (m, 1H), 8.19 (m, 2H).

EXAMPLE 45

6-(N-Isopropylcarbamoyl)amino-2-propyl-3-[(2'-(N-triphenylmethyl-tetrazol-5-yl)biphen-4-yl)methyl]-quinazolin-4(3H)-one The product of Example 41 was converted to the title compound in the same manner as that described in Example 48. The product was purified by MPLC over silica gel eluting with 65% EtOAc/hexane to give a colorless oil. 72% yield. $^1$H-NMR (CDCl$_3$): 0.91 (t, 3H, J=7.4 Hz). 1.13 (d, 6H, J=6.4 Hz), 1.73 (m, 2H), 2.58 (3 line m, 2H, J=7.8 Hz), 3.98 (m, 1H), 4,79 (d, 1H, J=7.8 Hz), 5.30 (bs, 2H), 6.89-7.98 (m, 10H), 7.10 (d, 2H, J=8.2 Hz), 7.21-7.32 (m, 12H), 7.46 (m, 2H), 7.63 (d, 1H, J=8.9 Hz), 7.92 (m, 2H), 8.15 (2.5, 8.8 Hz).

EXAMPLE 46

6-(N-Benzyl)amino-2-butyl-3-[(2'-(N-triphenylmethyl-tetrazol-5-yl)biphen-4-yl)methyl]quinazolin-4(3H)-one To 100 mg (0.14 mmol) of the amine from Example 40 in 2 mL of EtOH was added 16 mg (0.15 mmol) of benzaldehyde. The reaction mixture was heated to 60° C. for 1 hour, cooled to 0° C. and treated with 0.29 mL (0.29 mmol) of a 1M solution of NaCNBH₃ in THF. The reaction mixture was stirred overnight, concentrated in vacuo, and the residue partitioned between 25 mL of EtOAc and 15 mL of water. The phases were separated and the organic phase was washed with brine (1×25 mL) and dried over MgSO₄. The mixture was filtered and concentrated in vacuo and the residue was purified by flash chromatography over silica gel eluting with 25% EtOAc/hexanes to give 45 mg (0.06 mmol) of a yellow foam. ¹H-NMR (CDCl₃ 300 MHz): 0.88 (t, 3H, J=7.4 Hz), 1.31 (m, 2H), 1.66 (m, 2H), 2.61 (3 line m, 2H, J=7.8 Hz), 4.32 (bs, 1H), 4.43 (bs, 2H), 5.28 (bs, 2H), 6.88 (m, 8H), 7.08 (m, 3H), 7.20–7.53 (m, 19H), 7.91 (d, 1H).

EXAMPLE 47

2-Butyl-6-(N,N-dimethyl)amino-3-[(2'-(N-triphenylmethyl-tetrazol-5-yl)biphen-4-yl)methyl]quinazolin-4(3H)-one To 100 mg (0.138 mmol) of the nitro quinazolinone from Example 29 in 1 mL of EtOAc and 1 mL of MeOH was added 300 mg of formalin followed by 25 mg of 10% Pd/C. The mixture was rapidly stirred under hydrogen at atmospheric pressure overnight. The reaction mixture was filtered and concentrated in vacuo. The residue was purified by flash chromatography over silica gel eluting with 30% EtOAc/hexane to give 30 mg (0.04 mmol) of a white foam, 24% yield. ¹H-NMR (CDCl₃ 300 MHz): 0.88 (t, 3H, J=7.3 Hz), 1.42 (m, 2H), 1.69 (m, 2H), 2.62 (3 line m, 2H, J=7.9 Hz), 3.07 (s, 6H), 5.30 (bs, 2H), 6.90–6.99 (m, 6H), 7.07 (d, 2H, J=8.1 Hz), 7.21–7.37 (m, 13H), 7.45 (m, 3H), 7.57 (d, 1H, J=8.9 Hz), 7.92 (m, 1H).

EXAMPLE 48

2-Butyl-6-(N-isopropylcarbamoyl)amino-3-[(2'-(N-triphenylmethyl-tetrazol-5-yl)biphen-4-yl)methyl]-quinazolin-4(3H)-one To solution of 0.069 g (0.1 mmol) of the aminoquinazolinone from Example 40 in 1 mL of CH₂Cl₂ was added 12.7 mg (0.15 mmol) of isopropylisocyanate. The reaction mixture was stirred for 3 days. The mixture was diluted with 20 mL of EtOAc, washed with water (2×5 mL), brine (1×5 mL) and dried over MgSO₄. The mixture was filtered and concentrated in vacuo and the residue was purified by MPLC over a silica Lobar B column eluting with 50% EtOAc/hexanes to give 59.5 mg (0.07 mmol) of an oil, 76% yield. ¹H-NMR (CDCl₃ 300 MHz): 0.86 (t, 3H, J=7.3 Hz), 1.07 (d, 6H, J=6.5 Hz), 1.29 (m, 2H), 1.68 (m, 2H), 2.59 (3 line m, 2H, J=7.06 Hz), 3.95 (m, 1H), 5.18 (d, 1H, J=7.7 Hz), 5.28 (bs, 2H), 7.12 (m, 6H), 7.07 (d, 2H), 7.19–7.32 (m, 11H), 7.43 (m, 2H), 7.57 (m, 2H), 7.90 (m, 2H), 8.13 (m, 1H).

EXAMPLE 49

6-Acetamido-2-butyl-3-[(2'-butoxycarbonyl)biphen-4-yl)methyl]quinazolin-4-(3H)-one To 20 mg of the product of Example 39 in 0.75 mL of CH₂Cl₂ at room temperature was added 4.3 μL of acetic anhydride. After 6 hours a further 2 μL of acetic anhydride was added to the reaction mixture. The solution was allowed to stir for 7 days, diluted with 10 mL of EtOAc and washed with water (3×5 mL), brine (1×5 mL) and dried over MgSO₄. The solution was filtered and concentrted in vacuo to give 22 mg of a white solid, 100% yield. Attempted dissolution in EtOAc and CH₂Cl₂ for chromatogrphy failed due to insolubility. ¹H-NMR (CD₃OD): 0.65 (t, 3H, J=7.3 Hz), 0.91 (s, 9H), 1.12 (m, 2H), 1.48 (m, 2H), 1.87 (s, 3H), 2.63 (3 line m, 2H, J=7.7 Hz), 5.21 (bs, 2H), 6.92–7.39 (m, 10H), 7.67 (dd, 1H, J=2.5, 8.8 Hz), 8.19 (d, 1H, J=2.5 Hz). FABMS m/z 526 (M⁺+1) calc for C₃₂H₃₅N₃O₄.

SYNTHESIS OF 2-BUTYL-3-[(2'-(CARBOXY)BIPHEN-4-YL)METHYL]-ALKYLQUINAZOLIN-4(3H)-ONES

General procedure for the preparation of the carboxylic acids from the t-butyl esters is as follows:

To 1 mmol of the ester in 1 mL of dry CH₂Cl₂ at room temperature was added 0.5 mL of trifluoroacetic acid. The solution was stirred under N₂ over night and concentrated in vacuo. The residue was reconcentrated in vacuo after dissolving the reaction product in a mixture of 0.5 mL of CH₂Cl₂ and 3 mL of toluene. The residue was allowed to dry in vacuo overnight. Any impurities were removed by flash chromatography.

EXAMPLE 50

6-Acetamido-2-butyl-3-[(2'-(carboxy)biphen-4-yl)methyl]-quinazolin-4(3H)-one

The product of Example 49 was deprotected following the general procedure described above. Purification by flash chromatography eluting with 5:95:1 MeOH:CH₂Cl₂:HOAc to give a white solid, ¹H-NMR (CD₃OD): 0.61 (t, 3H, J=7.43 Hz), 1.12 (m, 2H), 1.42 (m, 2H), 1.86 (s, 3H), 2.52 (3 line m, 2H, J=7.4 Hz), 5.18 (bs, 2H), 6.85–7.22 (m, 8H), 7.19 (d, 1H, J=7.3 Hz), 7.46 (d, 1H, J=7.3 Hz), 7.69 (dd, 1H, J=2.2,8.8 Hz), 8.12 (d, 1H, J=2.22 Hz). FABMS m/z 470 (M⁺+1) calc for C₂₈H₂₇N₃O₄.

EXAMPLE 51

6-Amino-2-butyl-3-[(2'-(carboxy)biphen-4-yl)methyl]-quinazolin-4(3H)-one

The product of Example 39 was deprotected following the general procedure described above. Purification by flash chromatography over silica gel eluting with 60:40:1 EtOAc:hexane:acetic acid. The product is very insoluble when concentrated to give a white solid. ¹H-NMR (CDCl₃): 0.87 (t, 3H, J=7.37 Hz), 1.35 (m, 2H), 1.69 (m, 2H), 2.71 (3 line m, 2H, J=6.9 Hz), 3.2–4.5 (bs, 4H), 5.41 (bs, 2H), 7.05–7.59 (m, 10H), 7.54 (bs, 1H).

EXAMPLE 52

2-Butyl-3-[(2'-(carboxy)biphen-4-yl)methyl]quinazolin-4(3H)-one

The product of Example 17 was deprotected following the general procedure described above. The crude material was purified by flash chromatography eluting with 1:1:38:60 acetic acid/MeOH/hexane/methylene chloride. ¹H-NMR (CDCL₃): 9.60–8.50 (bs, 1H), 8.30 (m, 1H), 7.94 (m, 1H0, 7.71 (m, 2H), 7.58–7.37 (m, 3H), 7.32 (m, 3H), 7.19 (m, 2H), 5.45 (bs, 2H), 2.75 (3 line m, 2H), 1.67 (m, 2H), 1.34 (m, 2H), 0.84 (t, 3H). FABMS m/z 413 (M⁺+1).

EXAMPLE 53

2-Butyl-3-[(2'-(carboxy)biphen-4-yl)methyl]-5-methyl-quinazolin-4(3H)-one

The product of Example 27 was deprotected following the general procedure described above. The crude concentrated reaction mixture was homogeneous by TLC and NMR. $^1$H-NMR (CDCl$_3$): 0.88 (t, 3H, J=7.21), 1.43 (m, 2H), 1.69 (m, 2H), 2.87 (s, 3H), 3.13 (dd, 2H, J=8.0, 8.0 Hz), 5.46 (bs, 2H), 7.21–7.36 (m, 5H), 7.43 (d, 2H, J=8.74 Hz), 7.58 (t, 1H, J=7.4 Hz), 7.69–7.81 (m, 2H), 7.96 (d, 1H, J=7.8 Hz).

EXAMPLE 54

2-Butyl-3-[(2'-(carboxy)biphen-4-yl)methyl]-naphtho[2.3-e]quinazolin-4(3H)-one

The product of Example 24 was deprotected following the general procedure described above. The crude concentrated reaction mixture was homogeneous by TLC and NMR. $^1$H-NMR (CDCl$_3$): 0.91 (t, 3H, J=7.22 Hz), 1.49 (m, 2H), 1.75 (m, 2H), 3.20 (bdd, 2H, J=7.6, 7.6 Hz), 5.52 (bs, 2H), 7.20–7.35 (m, 5H), 7.42 (t, 1H, J=7.7 Hz), 7.55 (t, 1H, J=7.3 Hz), 7.68 (t, 1H, J=7.3 Hz), 7.77 (t, 1H, J=8.0 Hz), 7.94 (d, 1H, J=7.7 Hz), 8.07 (d, 2H, J=8.2 Hz), 8.93 (s, 1H), 11.99 (bs, 1H). FABMS: m/z 463 (M$^+$+1).

EXAMPLE 55

2-Butyl-3-[(2'-(carboxy)biphen-4-yl)methyl]-7-methyl-quinazolin-4(3H)-one

The product of Example 23 was deprotected following the general procedure described above. The product was purified by flash chromatography over silica eluting with 40% EtOAc/hexane/1% acetic acid. $^1$H-NMR (CDCl$_3$): 0.91 (t, 3H, J=7.3 Hz), 1.42 (m, 2H), 1.71 (m, 2H), 2.54 (s, 3H), 3.01 (dd, 2H, J=7.8, 7.8 Hz), 5.44 (bs, 2H), 7.10–7.45 (m, 8H), 7.54 (t, 1H, J=7.5 Hz), 7.69 (s, 1H), 7.93 (d, 1H, J=7.7 Hz), 8.19 (d, 1H, J=8.1 Hz). FABMS: 427 (M$^+$+1).

EXAMPLE 56

2-Butyl-3-[(2'-(carboxy)biphen-4-yl)methyl]-8-methyl-quinazolin-4(3H)-one

The product of Example 19 was deprotected following the general procedure described above. The product was purified by flash chromatography over silica gel eluting with 25% EtOAc/75% hexane/1% acetic acid. $^1$H-NMR (CDCl$_3$): 0.91 (t, 3H, J=7.3 Hz), 1.41 (m, 2H), 1.82 (m, 2H), 2.61 (s, 3H), 2.78 (dd, 2H, J=7.3, 7.3 Hz), 5.44 (bs, 2H), 7.15–7.61 (m, 9H), 7.92 (d, 1H, J=7.3 Hz), 8.15 (d, 1H, J=7.8 Hz). FABMS: 427 (M$^+$+1).

EXAMPLE 57

2-Butyl-3-[(2'-(carboxy)biphen-4-yl)methyl]-6-methyl-quinazolin-4(3H)-one

The product of Example 20 was deprotected following the general procedure described above. The product was purified by flash chromatography over silica gel eluting with 30% EtOAc/70% hexane/1% acetic acid. $^1$H-NMR (CDCl$_3$): 0.89 (3H, t), 1.38 (m, 2H), 1.69 (m, 2H), 2.48 (s, 3H), 2.83 (dd, 2H), 5.41 (bs, 2H), 7.16 (d, 2H), 7.22–7.31 (m, 3H), 7.41 (t, 1H), 7.52 (t, 1H(, 7.59 (m, 1H), 7.68 (d, 1H), 7.91 (d, 1H), 8.08 (s, 1H). FABMS: 427 (M$^+$+1).

EXAMPLE 58

2-Butyl-3-[(2'-(carboxy)biphen-4-yl)methyl]-6-nitroquinazolin-4(3H)-one

The product of Example 21 was deprotected following the general procedure described above. The product was purified by flash chromatography over silica gel eluting with 70:30:1 EtOAc:hexane:acetic acid, 80% yield. $^1$H-NMR (CDCl$_3$): 0.91 (t, 3H, J=7.33 Hz), 1.41 (m, 2H), 1.79 (m, 2H), 2.84 (3 line m, 2H, J=7.98 Hz), 5.45 (bs, 2H), 7.18–7.32 (m, 5H), 7.42 (dd, 1H, J=7.7, 7.7 Hz), 7.55 (dd, 1H, J=6.4, 6.4 Hz), 7.77 (d, 1H, J=9.0 Hz), 7.92 (d, 1H, J=7.4 Hz), 8.51 (dd, 1H, J=2.6, 9.3 Hz), 9.15 (d, 1H, J=2.6 Hz). FABMS m/z 458 (M$^+$+1) calc. for C$_{26}$H$_{23}$N$_3$O$_5$.

EXAMPLE 59A

2-Butyl-3-[(2'-(carboxy)biphen-4-yl)methyl]-6,8-dimethylquinazolin-4(3H)-one

The product of Example 25 was deprotected following the general procedure described above. Purification by flash chromatography over silica gel eluting with 30% EtOAc/hexanes/1% acetic acid. $^1$H-NMR (CDCl$_3$): 0.90 (t, 3H, J=7.3 Hz), 1.40 (m, 2H), 1.80 (m, 2H), 2.43 (s, 3H), 2.57 (s, 3H), 2.77 (3 line m, 2H, J=7.7 Hz), 5.44 (bs, 2H), 7.17–7.42 (m, 7H), 7.53 (dt, 1H, 7.5, 1.4 Hz), 7.90–7.95 (m, 2H). FABMS: 441 (M$^+$+1) calc. for C$_{28}$H$_{28}$N$_2$O$_3$.

ALTERNATIVE METHOD OF PREPARING CARBOXYLIC ACIDS FROM t-BUTYL ESTERS

EXAMPLE 59B

2-Butyl-3-[(2'-carboxybiphen-4-yl)-methyl]-6-isopropylquinazolin-4(3H)-one

A solution of 2-n-butyl-3-[(2'-(t-butoxycarbonyl)biphen-4-yl)-methyl]-6-isopropylquinazolin-4(3H)-one (0.198 g, 0.44 mmol) from Example 36B in a mixture of methylene chloride (3 ml) and anhydrous trifluoro acetic acid (3 ml) containing anisole (0.05 ml) was stirred at room temperature for 4 hours. The solvent was then removed under reduced pressure and the residue was triturated with dry ether to give the solid product, which was then collected by filtration and dried in vacuo over NaOH and P$_2$O$_5$ to give the desired product as the mono trifluoroacetate salt. $^1$H-NMR(CDCl$_3$): 0.91 (t, 3H, J=7.35 Hz), 1.32 (d, 6H, J=6.9 Hz), 1.47 (m, 2H), 1.72 (m, 2H), 3.12 (m, 3H), 5.48 (s, 2H), 7.14–7.96 (m, 11H), 8.16 (d, 1H, J=1.9 Hz). FAB-MS: m/e 399 (M+H).

SYNTHESIS OF 2-BUTYL-3-[(2'-(TETRAZOL-5-YL)BIPHEN-4-YL)METHYL]QUINAZOLIN-4(3H)-ONES FROM TRITYL PROTECTED INTERMEDIATES

EXAMPLE 60

2-Butyl-6-ethyl-3-[(2'-(tetrazol-5-yl)biphen-4-yl)methyl]quinazolin-4(3H)-one

The protected tetrazole from Example 38 (0.116 g, 0.165 mmol), was stirred with 1 ml of a mixture of 1:1:1 HOAc:THF:H$_2$O at 90° C. for 2 hours and then 4 hours at room temperature. The reaction mixture was concentrated in vacuo and the residue was purified by flash chromatography over silica gel eluting with 40:59:1 EtOAc:hexane:HOAc. Recovered 53.4 mg of a white powder, 69% yield. $^1$H-NMR (CDCl$_3$): 0.93 (t, 3H), 1.28 (t, 3H), 1.43 (m, 2H), 1.79 (m, 2H), 2.72 (m, 4H), 5.38 (bs, 2H), 7.18 (bs, 8H), 7.38 (d, 1H), 7.55 (m, 4H), 8.04 (s, 1H), 8.12 (d, 1H).

EXAMPLE 61

2-Butyl-7-chloro-3-[(2'-(tetrazol-5-yl)biphen-4-yl)methyl]quinazolin-4(3H)-one

Prepared as in Example 60 from the product of Example 37. Purification by flash chromatography over silica gel eluting with 40:59:1 EtOAc:hexane:HOAc to give a white powder. $^1$H-NMR (CDCl$_3$): 0.94 (t, 3H, J=7.3 Hz), 1.42 (m, 2H), 1.79 (m, 2H), 2.77 (3 line m, 2H, J=7.6 Hz), 5.37 (bs, 2H), 7.17 (s, 4H), 7.40 (m, 2H), 7.58 (m, 2H), 7.68 (d, 1H, J=1.96 Hz), 8.09 (dd, 1H, J=1.3, 7.4 Hz), 8.15 (d, 1H, J=8.5 Hz). FABMS m/z 471 (M$^+$ +1) calc. for C$_{26}$H$_{13}$N$_6$OCl.

EXAMPLE 62

2-Butyl-6-isopropyl-3-[(2'-(tetrazol-5-yl)biphen-4-yl)methyl]quinazolin-4(3H)-one Prepared as in Example 60 from the product of Example 28. Purification by flash chromatography over silica gel eluting with 40:59:1 EtOAc:hexane:HOAc to give a white powder. $^1$H-NMR (CDCl$_3$): 0.92 (t, 3H, J=7.3 Hz), 1.29 (d, 6H, J=6.9 Hz), 1.42 (m, 2H), 1.76 (m, 2H), 2.75 (3 line m, 2H, J=8.2 Hz), 3.03 (m, 1H), 5.38 (bs, 2H), 7.16 (bs, 4H), 7.38 (dd, 1H, J=1.6, 7.1 Hz), 7.5–7.7 (m, 4H), 8.06 bm, 2H). FABMS m/z 479 (M$^+$ +1) calc. for C$_{29}$H$_{30}$N$_6$O.

EXAMPLE 63

6-Acetoxymethyl-2-butyl-3-[(2'-(tetrazol-5-yl)biphen-4-yl)methyl]quinazolin-4(3H)-one The product of Example 35 was deprotected as in the method for Example 60. The product was purified by flash chromatography over silica gel eluting with 50:49:1 EtOAc:hexane:acetic acid to give a white powder, (92% yield). $^1$H-NMR (CDCl$_3$): 0.90 (t, 3H, J=7.3 Hz), 1.39 (m, 2H), 1.73 (m, 2H), 2.11 (s, 3H), 2.74 (3 line m, 2H, J=7.7 Hz), 5.17 (s, 2H), 5.35 (bs, 2H), 7.08 (m, 4H), 7.39 (dd, 1H), 7.45–7.72 (m, 5H), 7.94 (dd, 1H, J=6.13, 1.5 Hz), 8.17 (d, 1H, J=1.8 Hz). FABMS m/e:509 (M$^+$ +1) calc. for C$_{29}$H$_{28}$N$_6$O$_3$.

EXAMPLE 64

5-Acetoxymethyl-2-butyl-3-[(2'-(tetrazol-5-yl)biphen-4-yl)methyl]quinazolin-4(3H)-one The product of Example 36 was deprotected as in the method for Example 60. The product was purified by flash chromatography over silica gel eluting with 50:50:1 EtOAc:hexane:acetic acid to give a white powder, (78% yield). $^1$H-NMR (CDCl$_3$, 300 MHz): 0.94 (t, 3H, J=7.4 Hz), 0.43 (m, 2H), 1.79 (m, 2H), 2.17 (2, 3H), 2.78 (3 line m, 2H, J=7.8 Hz), 5.34 (s, 2H), 5.78 (s, 2H), 7.17 (s, 4H), 7.38–7.75 (m, 6H), 8.09 (m, 2H). FABMS m/e: 509 (M$^+$ +1) calc. for C$_{29}$H$_{28}$N$_6$O$_3$.

EXAMPLE 65

2-Butyl-6-nitro-3-[(2'-(tetrazol-5-yl)biphen-4-yl)methyl]quinazolin-4(3H)-one

The product of Example 29 was deprotected as in the method described in Example 60. The product was purified by flash chromatography over silica gel eluting with 50:49:1 EtOAc:hexane:acetic acid, 98% yield. $^1$H-NMR (CDCl$_3$, 300 MHz): 0.91 (t, 3H, KJ=7.3 Hz), 1.42 (m, 2H), 1.79 (m, 2H), 2.79 (3 line m, 2H, 7.8 Hz), 5.36 (bs, 2H), 7.14 (s, 4H), 7.37 (dd, 1H, J=1.5, 7.6 Hz), 7.52 (m, 2H), 7.73 (d, 1H, J=8.9 Hz), 7.97 (dd, 1H, J=2.0, 7.5 Hz), 8.48 (dd, 1H, J=9.0, 2.6 Hz), 9.01 (d, 1H, J=2.6 Hz). FABMS m/e: 482 (M$^+$ +1) calc. for C$_{26}$H$_{23}$N$_7$O$_3$.

EXAMPLE 66

6-Amino-2-butyl-3-[(2'-(tetrazol-5-yl)biphen-4-yl)methyl]quinazolin-4(3H)-one

The product of Example 40 was deprotected as in the method for Example 60. The product was purified by flash chromatography over silica gel eluting with 95:5:0.1 CHCl$_3$:MeOH:NH$_4$OH to give a white solid, 68% yield. $^1$H-NMR (CDCl$_3$, 300 MHz): 0.91 (t, 3H, J=7.3 Hz), 1.41 (m, 2H), 1.72 (m, 2H), 2.69 (3 line m, 2H, J=7.8 Hz), 5.35 (bs, 2H), 7.13 (s, 4H), 7.35–7.61 (m, 6H), 8.08 (dd, 1H, J=8.9, 1.7 Hz). FABMS m/e: 452 (M$^+$ +1) calc. for C$_{26}$H$_{25}$N$_7$O.

EXAMPLE 67

6-(N-Benzyl)amino-2-butyl-3-[(2'-(tetrazol-5-yl)biphen-4-yl)methyl]quinazolin-4(3H)-one The product of Example 46 was deprotected in the manner described in Example 60. The product was purified by flash chromatography over silica gel eluting with 5:95:0.01 MeOH:CHCl$_3$:NH$_4$OH to give slightly impure product. The material was purified further by MPLC over silica Lobar A column eluting with 50:50:1 EtOAc:hexane:acetic acid. $^1$H-NMR (CDCl$_3$ 300 MHz): 0.92 (t, 3H, J=7.3 Hz), 1.41 (m, 2H), 1.73 (m, 2H), 2.72 (3 line m, 2H, J=8.1 Hz), 4.39 (s, 2H), 5.35 (bs, 2H), 7.09 (dd, 1H, J=2.7, 8.8 Hz), 7.13 (s, 3H), 7.23–7.40 (m, 8H), 7.43–7.60 (m, 3H), 8.09 (dd, 1H). FABMS m/e: 542 (M$^+$ +1) calc. for C$_{33}$H$_{31}$N$_7$O.

EXAMPLE 68

2-Butyl-6-(N,N-dimethyl)amino-3-[(2'-tetrazol-5-yl)biphen-4-yl)methyl]quinazolin-4(3H)-one The product of Example 47 was deprotected in the manner described in Example 60. The product was purified by flash chromatography over silica gel eluting with 5% MeOH/CHCl$_3$, 95% yield. $^1$H-NMR (CDCl$_3$ 300 MHz): 0.92 (t, 3H, J=7.4 Hz), 1.42 (m, 2H), 1.75 (m, 2H), 2.71 (3 line m, 2H, J=8.2 Hz), 3.03 (s, 6H), 5.36 (bs, 2H), 7.12 (s, 4H), 7.21 (dd, 1H, J=2.9, 9.0 Hz), 7.31 (d, 1H, J=3.0 Hz), 7.37 (m, 1H), 7.52 (m,1H), 8.07, (dd, 1H, J=1.3, 7.2 Hz). FABMS m/e: 480 (M$^+$ +1) calc. for C$_{28}$H$_{29}$N$_7$O.

AN ALTERNATIVE METHOD OF DEPROTECTING THE TRITYL GROUP

EXAMPLE 69

6-Acetamido-2-butyl-3-[(2'-(tetrazol-5-yl)biphen-4-yl)methyl]quinazolin-4(3H)-one To a solution of 0.073 g (0.099 mmol) of the product from Example 42 in 2 mL of MeOH was added 4 drops of conc. HCl. The reaction mixture was stirred for 5 minutes and then made basic by addition of conc. NH$_4$OH. The pH of the solution was adjusted to 5.0 by addition of acetic acid. The reaction mixture was concentrated in vacuo and the residue was taken up in 20 ml of EtOAc. The solution was washed with water (2×5 mL) and brine (1×5 mL) and dried over MgSO$_4$. The mixture was filtered and concentrated in vacuo. The crude product was very insoluble and was consequently purified by trituration with CHCl$_3$, EtOAc and hexanes to give 32 mg of an off white solid, 65% yield. $^1$H-NMR (CD$_3$OD 300 MHz): 0.83 (t, 3H, J=7.3 Hz), 1.32 (m, 2H), 1.62 (2H, m), 2.09 (s, 2H), 2.68 (3 line m, 2H, J=8.1 Hz), 5.37 (bs, 2H), 7.00-7.10 (m, 4H), 7.42-7.61 (m, 5H), 7.89 (dd, 1H, J=2.4, 8.8 Hz), 8.39 (d, J=2.5 Hz). FABMS m/e: 494(M$^+$+1) calc. for C$_{28}$H$_{27}$N$_7$O$_2$.

EXAMPLE 70

2-Butyl-3-[(2'-(tetrazol-5-yl)biphen-4-yl)methyl]-6-valeroylamidoquinazolin-4(3H)-one The product of Example 43 was deprotected in the manner of Example 69. The crude product was purified by trituration with a mixture of EtOAc and hexanes to give a powder, 78% yield. $^1$H-NMR (CDCl$_3$ 300 MHz): 0.91 (t, 3H, J=7.4 Hz), 0.97 (t, 3H, J=7.3 Hz), 1.41 (m, 4H), 1.70 (m, 4H), 2.42 (t, 2H, J=7.6 Hz), 2.75 (3 line m, 2H), 5.46 (bs, 2H), 7.12 (m, 4H), 7.51-7.69 (m, 5H), 7.99 (dd, 1H), 8.48 (d, 1H).

EXAMPLE 71

2-Butyl-6-(N-carbobenzyloxy)amino-3-[(2'-(tetrazol-5-yl)biphen-4-yl)methyl]quinazolin-4(3H)-one The product of Example 44 was deprotected in the manner described in Example 69. The product was purified by MPLC over a silica Lobar A column eluting with 40:59:1 EtOAc:hexane:acetic acid to give a 55% yield of a white solid. $^1$H-NMR (CDCl$_3$, 300 MHz): 0.87 (t, 3H, J=7.4 Hz), 1.32 (m, 2H), 1.69 (m, 2H), 2.65 (3 line m, 2H, J=7.3 Hz), 5.15 (s, 2H), 5.29 (bs, 2H), 6.95 and 7.04 (AB, 4H, J=8.2 Hz), 7.30-7.42 (m, 5H), 7.49-7.59 (m, 3H), 7.72(bs, 1H), 7.98 (d, 1H), 8.06 (s, 1H), 8.12 (bd, 1H). FABMS m/e: 586 (M$^+$+1) calc. for C$_{34}$H$_{31}$N$_7$O$_3$

EXAMPLE 72

2-Butyl-6-(N-isopropylcarbamoyl)amino-3-[(2'-tetrazol-5-yl)biphen-4-yl)methyl]quinazolin-4(3H)-one The product of Example 48 was deprotected following the procedure of Example 69. The product was purified by trituration with EtOAc and hexanes. $^1$H-NMR (CD$_3$OD, 300 MHz): 0.82 (t, 3H, J=7.4 Hz), 1.10 (d, 6H, J=6.6 Hz), 1.29 (m, 2H), 1.40 (m, 2H), 2.65 (3 line m, 2H, J=7.9 Hz), 5.32 (bs, 2H), 6.99 (bs, 4H), 7.38 (m, 2H), 7.49 (m, 3H), 7.79 (dd, 1H, J=2.5, 8.8 Hz), 8.06 (d, 1H, J=2.5 Hz). FABMS m/e: 537 (M$^+$+1) calc. for C$_{30}$H$_{32}$N$_8$O$_2$

EXAMPLE 73

2-Butyl-3-[(2'-(tetrazol-5-yl)biphen-4-yl)methyl]-6-thiomethylquinazolin-4(3H)-one The product of Example 30 was deprotected in the same manner as that described in Example 69. The crude product was purified by flash chromatography over silica gel eluting with 50:49:1 EtOAc:hexane:acetic acid, 83% yield. $^1$H-NMR (CDCl$_3$, 300 MHz): 0.93 (t, 3H, J=7.4 Hz), 1.43 (m, 2H), 1.78 (m, 2H), 2.55 (s, 3H), 2.76 (3 line m, 2H, J=7.9 Hz), 5.38 (bs, 2H), 7.39 (dd, 1H, J=1.6,7.2 Hz), 7.50-7.62 (m, 4H), 7.97 (d, 1H, J=2.1 Hz), 8.07 (dd, 1H, J=1.3, 7.5 Hz). FABMS m/e: 483 (M$^+$+1) calc. for C$_{27}$H$_{26}$N$_6$SO

EXAMPLE 74

6-(N-Isopropylcarbamoyl)amino-2-propyl-3-[(2'-(tetrazol-5-yl)biphen-4-yl)methyl]quinazolin-4(3H)-one The product of Example 45 was deprotected in the manner of Example 69. The product was purified by trituration with EtOAc to give a white solid. 62% yield. $^1$H-NMR (CD$_3$OD): 0.88 (t, 3H, J=7.4 Hz), 1.11 (d, 6H, J=6.6 Hz), 1.63 (m, 2H), 2.64 (3 line m, 2H, J=7.9 Hz), 3.82 (m, 1H), 5.34 (bs, 2H), 7.01 (s, 4H), 7.38-7.53 (m, 7H), 7.79 (dd, 1H, J=2.6, 8.9 Hz).

EXAMPLE 75

2-Butyl-3-(4'-fluoro-2'-(tetrazol-5-yl)biphen-4-yl)methyl-6-isopropylquinazalin-4(3H)-one To a solution of 2-butyl-3-(4'-fluoro-2'-N-triphenylmethyltetrazol-5-yl)biphen-4-yl)methyl-6-isopropylquinazalinone from Example 33 (94.5 mg; 0.128 mmol) in MeOH (4 mL) was added 9N HCl (10 drops). The reaction was allowed to stir overnight. After ca. 15 hrs. the MeOH was removed in vacuo. The product was purified by trituration with Et$_2$O to afford 54.2 mg (80%) of the title compound. Characteristic peaks $^1$H NMR (300 MHz, CD$_3$OD) d 0.86 (t, 3H), 1.38 (d, 6H), 1.52 (m, 2H), 1.69 (m, 2H), 3.08 (t, 2H), 3.20 (m, 1H), 5.60 (s, 2H), 7.19 (d, 2H), 7.33 (d, 2H), 7.74 (d, 1H), 8.00 (dd, 1H), 8.25 (d, 1H); mass spectrum, m/e 497 (m+H calcd for C$_{29}$H$_{29}$N$_6$OF, 497).

SYNTHESIS OF 2-BUTYL-3-[(2'-(TETRAZOL-5-YL)BIPHEN-4-YL)METHYL]QUINAZOLIN-4(3H)-ONES FROM NITRILES

General procedure for the conversion of the biphenyl nitrile to tetrazole is described below:

To a solution of 0.28 mmol of the nitrile dissolved in 2 mL of dry toluene was added 0.56 mmol of trimethylstannyl azide (see prior section for preparation). The reaction mixture was refluxed over night, at which time a further 0.56 mmol of azide was added and the reaction mixture refluxed a further 12 hours. The resulting suspension was suspended in 50 mL of EtOAc and washed with sat. NH$_4$Cl (3×10 mL) and dried over MgSO$_4$. The solution was filtered and concentrated in vacuo. The method of purification and spectral data is shown below.

EXAMPLE 76

2-Butyl-6-methyl-3-[(2'-(tetrazol-5-yl)biphen-4-yl)methyl]quinazolin-4(3H)-one

The product of Example 22 was treated as in the general method above. The residue was purified by flash chromatography over silica gel eluting 60% EtOAc/hexane/1% acetic acid to give 0.08 mmol of pure tetrazole, 32% yield. $^1$H-NMR (CDCl$_3$): 0.92 (t, 3H, J=7.3 Hz), 1.42 (m, 2H), 1.75 (m, 2H), 2.46 (s, 3H), 2.74 (3 line m, 2H, J=7.9 Hz), 5.37 (bs, 2H), 7.11 (bs, 4H), 7.39 (m, 1H), 7.55 (m, 4H), 8.00 (m, 1H). FABMS m/z 451 (M$^+$+1) calc. for C$_{27}$H$_{26}$N$_6$O

EXAMPLE 77

2-Butyl-3-[(2'-(tetrazol-5-yl)biphen-4-yl)methyl]-quinazolin-4(3H)-one

The product of Example 18 was treated as in the general method above. The residue was purified by MPLC over silica gel eluting with 1:40:59 acetic acid:EtOAc:hexanes. The recovered product (R$_f$ 0.27 in 1:39:60 acetic acid:EtOAc:hexanes) was further purified by HPLC on a C8 reverse phase column eluting with 75:25 acetonitrile:water/0.01% TFA to give the product as a white foam, 26% yield. $^1$H-NMR (300 MHz, CDCl$_3$): 11.50-10.30 (bs, 1H), 8.35 (m, 1H), 7.90 (m, 2H), 7.71 (m, 2H), 7.53 (m, 1H), 7.44 (m, 1H), 7.34 (M, 1h), 7.12 (m. 4H), 5.45 (bs, 2H), 3.17 (3 line m, 2H), 1.82 (m, 2H), 1.50 (m, 2H), 0.95 (t, 3H). FABMS m/z 437 (M+ +1).

EXAMPLE 76

6-Methyl-2-propyl-3-[(2'-(tetrazol-5-yl)biphen-4-yl)methyl]quinazolin-4(3H)-one

The product of Example 26 was treated as in the general method above. The crude tetrazole was purified in the same manner as in the 2-butyl case above, 13% yield. $^1$H-NMR (300 MHz, CDCl$_3$): 8.11 (m, 1H), 8.02 (s, 1H), 7.56 (m, 4H), 7.40 (m, 1H), 7.19 (m, 4H), 5.40 (bs, 2H), 2.73 (3 line m, 2H), 2.47 (s, 3H), 1.83 (m, 2H), 1.02 (t, 3H). FABMS m/z 437 (M+ +1). pKa 4.7.

FURTHER TRANSFORMATIONS OF ANTAGONISTS

EXAMPLE 77

2-Butyl-6-hydroxymethyl-3-[(2'-(tetrazol-5-yl)biphen-4-yl)methyl]quinazolin-4(3H)-one A solution of 0.2 g (0.38 mmol) of the product of Example 63 was dissolved in 5 mL of MeOH and was treated with 1 mL of 1N NaOH (1.0 mmol) and stirred over night. The resulting solution was extracted with EtOAc (3×10 mL). The organic phase was washed with water (2×5 mL) and brine (1×5 mL) and dried over MgSO$_4$. The mixture was filtered and concentrated in vacuo and the residue was purified by flash chromatography over silica gel eluting with 80:19:1 EtOAc:hexane:acetic acid to give 0.17 g (0.36 mmol) of a white foam, 93% yield. $^1$H-NMR (CD$_3$OD): 0.88 (t, 3H, J=7.38 Hz), 1.41 (m, 2H), 1.48 (m, 2H), 2.73 (3 line m, 2H, J=8.03 Hz), 4.60 (s, 2H), 5.38 (bs, 2H), 7.08 (m, 4H), 7.20 (m, 1H), 7.50 (m, 2H), 7.61 (m, 2H), 7.77 (dd, 1H, J=2.0, 9.0 Hz), 8.17 (s, 1H). FABMS m/e: 467 (M+ +1) calc. for C$_{27}$H$_{26}$N$_6$O$_2$

EXAMPLE 78

2-Butyl-5-hydroxymethyl-3-[(2'-(tetrazol-5-yl)biphen-4-yl)methyl]quinazolin-4(3H)-one To a solution of 0.2 g (273 mmol) of the product of Example 64 in 8 mL of MeOH was added 20 drops of conc. HCl. The reaction mixture was stirred overnight and the pH was then adjusted to pH 6.0. The MeOH was removed in vacuo and the residue was triturated with 3 mL of EtOAc to give, after drying, 90 mg (1.9 mmol) of a white powder, 71% yield. $^1$H-NMR (CD$_3$OD): 0.92 (t, 3H, J=7.38 Hz), 1.40 (m, 2H), 1.72 (m, 2H), 2.76 (3 line m, 2H, J=8.08 Hz), 5.16 (s, 2H), 5.44 (bs, 2H), 7.13 (m, 4H), 7.52-7.71 (m, 6H), 7.86 (t, 1H, J=7.81 Hz). FABMS m/e: 467 (M+ +1) calc. for C$_{27}$H$_{26}$N$_6$O$_2$

EXAMPLE 79

2-Butyl-6-carboxy-3-[(2'-(tetrazol-5-yl)biphen-4-yl)methyl]quinazolin-4(3H)-one

To a solution of 115 mg (0.25 mmol) of the product of Example 77 in 6 mL of CH$_2$Cl$_2$ was added 600 mg of MnO$_2$ followed by 200 mg of 3 Å molecular sieves. The reaction mixture was stirred for 12 hours and then filtered through celite. The celite was washed with CH$_2$Cl$_2$ (20 mL) and the combined filtrates were concentrated in vacuo to give 65 mg of a white foam. 31 mg (0.067 mmol) of the crude aldehyde intermediate was suspended in 0.4 mL of t-BuOH and treated with 260 uL of 5% NaH$_2$PO$_4$ in water and 780 μL of 0.5N KMnO$_4$ solution. After 1 hour the reaction mixture was concentrated in vacuo and the residue was partitioned between 30 mL water and 60 mL of EtOAc. The aqueous phase was extracted with EtOAc (2×10 mL) and the combined organic phases were washed with brine (1×10 mL) and dried over MgSO$_4$. No product could be detected in this organic phase. The aqueous phase was acidified to pH 1.0 with conc HCl and extracted with EtOAc (3×50 mL). The combined organic phases were washed with water ((2×15 mL) and brine (1×15 mL) and dried over MgSO$_4$. The solution was dried over MgSO$_4$, filtered and concentrated in vacuo to give 20 mg of a white solid, 59% yield. $^1$H-NMR (CD$_3$OD): 0.82 (t, 3H, J=7.3 Hz), 1.31 (m, 2H), 1.68 (m, 2H), 2.74 (3 line m, J=8.03), 5.38 (bs, 2H), 7.08 (m, 4H), 7.48 (m, 2H), 7.58 (m, 2H), 7.62 (d, 1H, J=8.4 Hz), 8.28 (dd, 1H, J=1.9,8.7 Hz), 8.80 (d, 1H, J=1.9 Hz). FABMS m/e: 481 (M+ +1) calc. for C$_{27}$H$_{24}$N$_6$O$_3$

EXAMPLE 80

2-Butyl-5-carboxy-3-[(2'-(tetrazol-5-yl)biphen-4-yl)methyl]quinazolin-4(3H)-one

To 50 mg (0.11 mmol) of the product of Example 78 suspended in 3 mL of CH$_2$Cl$_2$ was added 500 mg of activated MnO$_2$ and a spatula tip full of activated 3 Å molecular sieves. The mixture was vigorously stirred overnight under N$_2$. Earlier experiments had indicated that the resulting aldehyde was very insoluble and had a propensity to adhere to the MnO$_2$. Consequently, the reaction mixture was concentrated in vacuo and the crude mixture treated with 0.6 mL of t-BuOH, 0.42 mL of 5% aqueous NaH$_2$PO$_4$ and 1.25 mL of 0.5N KMnO$_4$. The solvent was removed in vacuo and the residue suspended in a mixture of 40 mL of EtOAc and 40 mL of water. The mixture was then filtered to remove the MnO$_2$ and the solid residue was washed with water and EtOAc. The resulting emulsion was treated with 5 mL of 1N NaOH to make the aqueous phase basic and break up the emulsion. The aqueous phase was extracted with EtOAc (3×50 mL) and then acidified with 1N HCl. The aqueous phase was extracted with EtOAc (3×50 mL) and the combined organic extracts of the acidified solution were washed with brine (1×50 mL) and dried over MgSO$_4$. The mixture was filtered and concentrated in vacuo to give 35.5 mg (0.07 mmol) of a solid, 69% yield. $^1$H-NMR (CD$_3$OD 300 MHz): 0.91 (t, 3H, J=7.38 Hz), 1.39 (m, 2H), 1.72 (m, 2H), 2.77 (7.9 Hz), 5.44 (bs, 2H), 7.14 (AB, 4H, J=9.2 Hz), 7.47-7.79 (m, 6H), 7.82 (t, 1H, J=7.1 Hz). FABMS m/e: 481 (M+ +1) calc. for C$_{27}$H$_{24}$N$_6$O$_3$

EXAMPLE 81

2-Butyl-6-carbomethoxy-3-[(2'-(tetrazol-5-yl)biphen-4-yl)-methyl]quinazolin-4(3H)-one To a suspension of 65 mg (0.14 mmol) of the product from Example 77 in 3 mL of CH$_2$Cl$_2$ was added 650 mg of MnO$_2$ and 200 mg of powdered activated 3A° molecular sieves. The reaction mixture was stirred for 3 hours at which time TLC (70:30:1, EtOAc:hexane:acetic acid) indicated complete conversion to the less polar aldehyde intermediate. The reaction mixture was concentrated in vacuo and the residue was suspended in 3 mL of MeOH. To this suspension was added 35 mg (0.7 mmol) of NaCN and 12 mg (0.21 mmol) of acetic acid. The reaction mixture was stirred over night and then filtered through celite. The solid residue was washed with 20 mL of MeOH. The filtrate was concentrated in vacuo and the residue was redissolved in 65 mL of EtOAc. The solution was washed with water (3×40 mL), brine (1×40 mL) and dried over MgSO$_4$. The mixture was filtered and concentrated in vacuo to give 29 mg of an oil. The product was purified by flash chromatography over silica gel eluting with 50:49:1 EtOAc:hexane:acetic acid to give 19 mg (0.04 mmol) of a white foam, 27% yield. $^1$H-NMR (CDCl$_3$ 300 MHz): 0.93 (t, 3H, J=7.38 Hz), 1.43 (m, 2H), 1.79 (m, 2H), 2.78 (3 line m, 2H, J=8.08 Hz), 3.95 (s, 3H), 5.38 bs, 2H), 7.16 (s, 4H), 7.40 (d, 1H, 1.6 Hz), 7.53 (m, 2H), 7.67 (d, 1H, J=8.5 Hz), 8.04 (dd,1H, J=7.43, 1.6 Hz), 8.34 (dd, 1H, J=8.6, 2.0 Hz), 8.89 (d, 1H, J=1.9 Hz). FABMS m/e: 495 (M$^+$+1) calc. for C$_{28}$H$_{26}$N$_6$O$_3$

EXAMPLE 82

2-Butyl-5-carbomethoxy-3-[(2'-(tetrazol-5-yl)biphen-4-yl)-methyl]quinazolin-4(3H)-one The product of Example 78 was treated as described in Example 81 to give the crude ester. The product was purified by MPLC over a silica gel Lobar A column eluting with 60:40:1 EtOAc:hexane:acetic acid to give a white foam, 38% yield. $^1$H-NMR (CDCl$_3$ 300 MHz): 0.94 (t, 3H, J=7.37 Hz), 1.43 (m, 2H), 1.80 (m, 2H), 2.80 (3 line m, 2H, J=8.2 Hz), 3.96 (s, 3H), 5.34 (bs, 2H), 7.15 (s, 4H)<7.39 (m, 2H), 7.54 (m, 2H), 7.77 (m, 2H), 8.07 (d, 1H). FABMS m/e: 495 (M$^+$+1) calc. for C$_{28}$H$_{26}$N$_6$O$_3$

EXAMPLE 83

2-Butyl-6-(methylsulfonyl)-3-[(2'-(tetrazol-5-yl)-biphen-4-yl)methyl]quinazolin-4(3H)-one To a solution of 0.05 g (0.11 mmol) of the deprotected quinazolinone from Example 73 in 3 mL of acetic acid at room temperature was added 0.5 mL of 30% hydrogen peroxide. The reaction mixture was stirred over night and then concentrated in vacuo. The residue was purified by flash chromatography over silica gel eluting with 65:34:1 EtOAc:hexane:acetic acid. The product was dissolved in toluene and concentrated in vacuo to remove any acetic acid by azeotropic distillation to give 32 mg (0.06 mmol) of a white powder, 62% yield. $^1$H-NMR (CDCl$_3$ 300 MHz): 0.90 (t, 3H, J=7.3 Hz), 1.41 (m, 2H), 1.76 (m, 2H), 2.79 (3 line m, 2H, J=8.03 Hz), 3.10 (s, 3H), 5.34 (bs, 2H), 7.09 (s., 4H), 7.35–7.59 (m, 3H), 7.78 (d, 1H, J=8.7 Hz), 7.88 (dd, 1H, J=1.5,7.6 Hz), 8.18 (dd, 1H, J=2.2,8.6 Hz), 8.75 (d, 1H, J=1.96 Hz). FABMS m/e: 515(M$^+$+1) calc. for C$_{27}$H$_{26}$N$_6$SO$_3$.

EXAMPLE 84

2-Butyl-6-(methylsulfinyl)-3-[(2'-(tetrazol-5-yl)biphen-4-yl)methyl]quinazolin-4(3H)-one To a solution of 43.7 mg (0.1 mol) of the deprotected quinazolinone from Example 73 in 1 mL of acetic acid was added 12.4 mg (0.11 mmol) of a 30% H$_2$O$_2$ solution in water. After stirring overnight TLC (50;30;19:1 EtOAc:hexane:MeOH:acetic acid) indicated that the reaction was incomplete. Addition of a further 12.4 mg of the H$_2$O$_2$ solution gave, after 2 hours, complete conversion to a more polar product. The reaction mixture was concentrated in vacuo and the residue was purified by flash chromatography over silica gel eluting with 50:30:19:1 EtOAc:hexane:MeOH: acetic acid to give 27 mg (0.05 mmol) of a white solid, 50% yield. $^1$H-NMR (CDCl$_3$, 300 MHz): 0.94 (t, 3H, J=7.3 Hz), 1.42 (m, 2H), 1.81 (m, 2H), 2.71 (s, 3H), 2.76 (3 line m, 2H, J=6.0 Hz), 5.31 and 5.57 (AB, 2H, J=16.2 Hz), 7.18 (m, 4H), 7.39–7.61 (m, 3H), 7.83 (d, 1H, J=8.7 Hz), 7.96 (d, 1H, J=7.6 Hz), 8.06 (d, 1H, J=8.7 Hz), 8.62 (d, 1H, J=1.8 Hz). FABMS m/e: 499 (M$^+$+1) calc. for C$_{27}$H$_{26}$N$_6$SO

EXAMPLE 85

2-Butyl-3-[(2'-(N-benzenesulfonyl)carboxamidobiphen-4-yl)-methyl]-6-isopropylquinazolin-4(3H)-one The carboxylic acid (0.05 g, 0.088 mMol), obtained form Example 59B was dissolved in dry THF (1 ml), and to the solution was added 1,1'carbonyl-diimidazole (0.030 g, 0.18 mMol). The mixture was refluxed for 4 hours and then cooled down to room temperature. To the reaction were then added benzenesulfonamide (0.031 g, 0.19 mMol) and DBU (0.029 g), and the mixture was refluxed for 7 hours. The reaction was then concentrated in vacuo, and the residue was treated with 5% aqueous citric acid (5 ml) and extracted with ethyl acetate (3×15 ml). The combined organic layer was washed with brine and then dried ober anhydrous sodium sulfate. The crude product, obtained after removal of the solvent, was purified by flash-chromatography over silica-gel using 2% methanol in methylene chloride to give the titled compound. Yield: 0.015 g (25%, amorphous solid). 1H-NMR(CD$_3$OD): 0.92 (t, 3H, J=7.35 Hz), 1.35 (d, 6H, J=6.9 Hz), 1.40 (m, 2H), 1.71 (m, 2H), 2.76 (t, 2H, J=7.7 Hz), 3.16 (m, 1H), 5.46 (broad s, 2H), 6.86–7.88 (m, 15H), 8.20 (d, 1H, J=1.9 Hz). FAB-MS: m/e 594 (M+H), 616 (M+Na).

PREPARATION OF 1,2 DISUBSTITUTED QUINAZOLIN-4(1H)-ONES

EXAMPLE 86

N-Valeroyl-2-aminobenzonitrile

To a solution of 500 mg 2-aminobenzonitrile (4.23 mmol), 514 mg triethylamine (5.08 mmol), and 50 mg DMAP (0.41 mmol) in 6 mL CH$_2$Cl$_2$ at 0° C. was added 562 mg valeroyl chloride (4.66 mmol) dropwise over 1 minute. The mixture was warmed to room temperature and stirred for 20 minutes. The mixture was then diluted with water and brine and was extracted three times with ether. The combined organic material was dried over MgSO$_4$, stripped of solvent in vacuo, and was purified by flash chromatography over silica eluting with 20% ethyl acetate in hexane to give the title compound. R$_f$ 0.22 in 20% ethyl acetate in hexane. $^1$H-NMR (300 MHz, CDCl$_3$): 8.42 (d, 1H), 7.60–7.10 (m, 2H), 6.72 (m, 1H), 4.40 (br s, 1H), 2.46 (t, 2H), 1.74 (m, 2H), 1.43 (m, 2H), 0.97 (t, 3H)

EXAMPLE 87

N-Valeroyl-N-[(2'-(t-butyoxycarbonyl)biphen-4-yl)methyl]-2-aminobenzonitrile To a solution of 146 mg of the product from Example 86 (0.72 mmol), 250 mg (0.72 mmol) 4-bromomethyl-2'-t-butoxycarbonylbiphenyl, and 119 mg NaI (0.79 mmol) in 4 mL DMF was added 46 mg 60% NaH dispersion in oil (1.15 mmol) at room temperature. After 45 minutes the mixture was diluted with water and brine and then was extracted three times with ether. The combined organic material was dried over MgSO$_4$, stripped off solvent in vacuo, and was purified by MPLC over silica eluting with 20% ethyl acetate in hexane. $R_f$ 0.20 in 20% ethyl acetate in hexane. $^1$H-NMR (300 MHz, CDCl$_3$): 7.75 (d, J=7.7 Hz, 2H), 7.58–7.20 (m, 9H), 6.99 (d, J=7.7 Hz, 1H), 5.60 (d, J=14.5 Hz, 1H), 4.42 (d, J=14.3 Hz, 1H), 2.05 (m, 2H), 1.62 (m, 2H), 1.26 (s, 9H), 1.25 (m, 2H), 0.85 (t, 3H).

EXAMPLE 88

2-Butyl-1-[(2'-(carboxy)biphen-4-yl)methyl]quinazolin-4(1H)-one

To a solution of the purified N-valeroyl-N-[(2'-(t-butoxycarbonyl)biphen-4-yl)methyl]-2-aminobenzonitrile (from Example 87) in 4 mL methanol were added 245 mL 30% H$_2$O$_2$ and 720 mL 3.0 N NaOH at room temperature. The mixture was heated to reflux for 1 hour. An additional 245 mL 30% H$_2$O$_2$ was added and the mixture was refluxed for an additional 45 minutes. The solution was diluted with brine then extracted three times with ether. The combined organic material was dried over MgSO$_4$, stripped of solvent in vacuo, and was flash chromatographed over silica eluting with 25% ethyl acetate in methylene chloride to give a white solid, $R_f$ 0.13 in 25% ethyl acetate in methylene chloride. The solid was stirred in 4 mL CH$_2$Cl$_2$ and 4 mL TFA over 4 hours. The volatiles were removed in vacuo and the crude material was flash chromatographed over silica eluting with 1:4:95 acetic acid/methanol/methylene chloride to give a white crystalline solid. $R_f$ 0.14 in 1:4:95 acetic acid/methanol/methylene chloride. $^1$H-NMR (300 MHz, CD$_3$OD): δ 8.34 (m, 1H), 7.89–7.06 (m, 11H), 5.79 (s, 2H), 3.01 (3 line m, 2H), 1.81 (m, 2H), 1.49 (m, 2H), 0.95 (t, 3H). FABMS m/z 413 (M$^+$+1).

In a similar fashion the following 1,2-dialkylated quinazolin-4(1H)-ones may be prepared:

2-Butyl-1-[(2'-(tetrazol-5-yl)biphen-4-yl)methyl]-quinazolin-4(1H)-one;
2-Propyl-1-[(2'-(tetrazol-5-yl)biphen-4-yl)methyl]-quinazolin-4(1H)-one;
2-Butyl-6-methyl-1-[(2'-tetrazol-5-yl)biphen-4-yl)methyl]quinazolin-4(1H)-one;
6-Methyl-2-pentyl-1-[(2'-(tetrazol-5-yl)biphen-4-yl)methyl]quinazolin-4(1H)-one;
2-Butyl-6-methyl-1-[(2'-(tetrazol-5-yl)biphen-4-yl)methyl]quinazolin-4(1H)-one;
2-Butyl-5-methyl-1-[(2'-(tetrazol-5-yl)biphen-4-yl)methyl]quinazolin-4(1H)-one;
2-Butyl-7-methyl-1-[(2'-(tetrazol-5-yl)biphen-4-yl)methyl]quinazolin-4(1H)-one;
2-Butyl-6-nitro-1-[(2'-(tetrazol-5-yl)biphen-4-yl)methyl]quinazolin-4(1H)-one;
2-Butyl-8-methyl-1-[(2'-(tetrazol-5-yl)biphen-4-yl)methyl]quinazolin-4 (1H)-one;
5-Benzyl-2-butyl-1-[(2'-(tetrazol-5-yl)biphen-4-yl)methyl]quinazolin-4(1H)-one.

FORMULATION EXAMPLES

Typical Pharmaceutical Compositions Containing a Compound of the Invention

A: Dry Filled Capsules Containing 50 mg of Active Ingredient Per Capsule

| Ingredient | Amount per capsule (mg) |
| --- | --- |
| 2-Butyl-6-isopropyl-3-[(2'-(tetrazol-5-yl)biphen-4-yl)methyl]-quinazolin-4(3H)-one | 50 |
| Lactose | 149 |
| Magnesium stearate | 1 |
| Capsule (size No. 1) | 200 |

The 2-butyl-6-isopropyl-3-[(2'-(tetrazol-5-yl)biphen-4-yl)methyl]quinazolin-4(3H)-one can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 2-butyl-6-isopropyl-3-[(2'-(tetrazol-5-yl)biphen-4-yl)methyl]quinazolin-4(3H)-one (25 mg), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide (25 mg) and 2-butyl-6-isopropyl-3-[(2'-(tetrazol-5-yl)biphen-4-yl)methyl]quinazolin-4(3H)-one (50 mg) pregelatinized starch USP (82 mg), microcrystalline cellulose (82 mg) and magnesium stearate (1 mg).

D: Suppository

Typical suppository formulations for rectal administration can contain 2-butyl-6-isopropyl-3-[(2'-(tetrazol-5-yl)biphen-4-yl)methyl]quinazolin-4(3H)-one (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain 2-butyl-6-isopropyl-3-[(2'-(tetrazol-5-yl)biphen-4-yl)methyl]quinazolin-4(3H)-one sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertensive and/or a diuretic and/or angiotensin converting enzyme inhibitor and/or a calcium channel blocker.

What is claimed is:

1. A compound of formula (I):

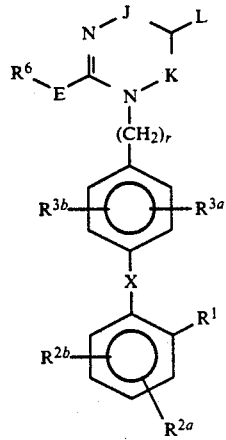 (I)

wherein:
L is connected with J or K to form an aromatic ring as defined below;
J is —C(=M)— or J and L are connected together to form a 6 carbon aromatic ring substituted with $R^{7a}$, $R^{7b}$, $R^{8a}$ and $R^{8b}$;
K is —C(=M)— or K and L are connected together to form a 6 carbon aromatic ring substituted with $R^{7a}$, $R^{7b}$, $R^{8a}$ and $R^{8b}$, provided that only one of J and K is —C(=M)—;
M is O or $NR^{22}$
$R^1$ is
(a) —$CO_2R^4$,
(b) —$SO_3R^5$,
(c) —$NHSO_2R^{23}$,
(d) —$PO(OR^5)_2$,
(e) —$SO_2$—NH—$R^{23}$,

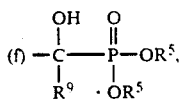

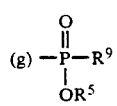

(h) —$SO_2NH$—CO—$R^{23}$,
(i) —$CH_2SO_2NH$—CO—$R^{23}$,
(j) —$CONH$—$SO_2R^{23}$,
(k) —$CH_2CONH$—$SO_2R^{23}$,
(l) —$NHSO_2NHCO$—$R^{23}$,
(m) —$NHCONHSO_2$—$R^{23}$,

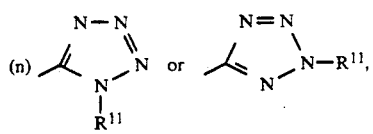

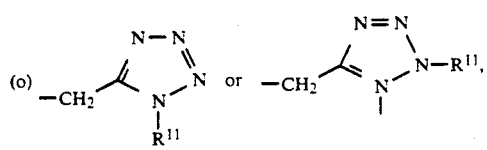

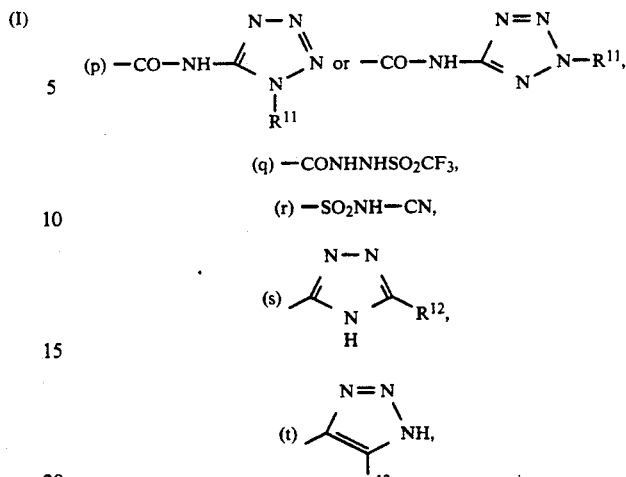

(q) —$CONHNHSO_2CF_3$,
(r) —$SO_2NH$—CN, (u) —$PO(OR^5)(OR^4)$,
(v) —$SO_2NHCONR^4R^{23}$, or
(w) —$CH_2SO_2NHR^{23}$, wherein heteroaryl is an unsubstituted, monosubstituted or disubstituted five or six membered aromatic ring which contains from 1 to 3 heteroatoms selected from the group consisting of O, N or S and wherein the substituents are members selected from the group consisting of —OH, —SH, —$C_1$-$C_4$-alkyl, —$C_1$-$C_4$-alkoxy, —$CF_3$, Cl, Br, F, I, —$NO_2$, —$CO_2H$, —$CO_2$—($C_1$-$C_4$-alkyl), —$NH_2$, —NH($C_1$-$C_4$-alkyl) and —N($C_1$-$C_4$-alkyl)$_2$;

$R^{2a}$ and $R^{2b}$ are each independently
(a) H,
(b) Cl, Br, I, or F,
(c) $NO_2$,
(d) $NH_2$,
(e) $C_1$-$C_4$-alkylamino,
(f) di($C_1$-$C_4$-alkyl)amino,
(g) $SO_2NHR^9$,
(h) $CF_3$,
(i) $C_1$-$C_6$-alkyl,
(j) $C_1$-$C_6$-alkoxy,
(k) $C_1$-$C_6$-alkyl-S-,
(l) $C_2$-$C_6$-alkenyl,
(m) $C_2$-$C_6$-alkynyl,
(n) aryl,
(o) aryl($C_1$-$C_4$-alkyl), or
(p) $C_3$-$C_7$-cycloalkyl;

$R^{3a}$ is
(a) H,
(b) Cl, Br, I, or F,
(c) $C_1$-$C_6$-alkyl,
(d) $C_1$-$C_6$-alkoxy, or
(e) $C_1$-$C_6$-alkoxyalkyl;

$R^{3b}$ is
(a) H,
(b) Cl, Br, I, or F,
(c) $NO_2$,
(d) $C_1$-$C_6$-alkyl,
(e) $C_1$-$C_6$-acyloxy,
(f) $C_3$-$C_7$-cycloalkyl,
(g) $C_1$-$C_6$-alkoxy,
(h) —$NHSO_2R^4$,
(i) hydroxy-($C_1$-$C_4$-alkyl), (j) aryl-$(C_1$-$C_4$-alkyl),
(k) $C_1$-$C_4$-alkylthio,
(l) $C_1$-$C_4$-alkyl sulfinyl,
(m) $C_1$-$C_4$-alkyl sulfonyl,
(n) $NH_2$,
(o) $C_1$-$C_4$-alkylamino,
(p) di($C_1$-$C_4$alkyl)amino-,
(q) fluoro-$C_1$-$C_4$-alkyl,
(r) $-SO_2-NHR^9$,
(s) aryl,
(t) furyl,
(u) $CF_3$,
(v) $C_2$-$C_6$-alkenyl, or
(w) $C_2$-$C_6$-alkynyl;

wherein aryl is phenyl or naphthyl or substituted phenyl or naphthyl with one or two substituents selected from the group consisting of Cl, Br, I, F, $N(R^4)_2$, $CO_2R^4$, $C_1$-$C_4$-alkyl, $C_1$-$C_4$-alkoxy, $NO_2$, $CF_3$, $C_1$-$C_4$-alkylthio, or OH;

$R^4$ is H, aryl, heteroaryl, $C_1$-$C_6$-alkyl, or aryl $C_1$-$C_6$ alkyl;

$R^{4a}$ is aryl, $C_1$-$C_6$-alkyl or aryl $C_1$-$C_6$ alkyl;

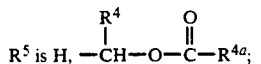

$R^5$ is H, $-\overset{R^4}{\underset{|}{CH}}-O-\overset{O}{\underset{\|}{C}}-R^{4a}$;

E is a single bond, $-NR^{13}(CH_2)_s-$, $-S(O)_x(CH_2-)_s-$ where x is 0 to 2 and s is 0 to 5, $-CH(OH)-$, $-O-$, or $CO-$;

$R^6$ is
(a) phenyl or substituted phenyl with 1 or 2 substituents selected from the group consisting of Cl, Br, I, F, $-O-C_1$-$C_4$-alkyl, $C_1$-$C_4$-alkyl, $-NO_2$, $-CF_3$, $-SO_2NR^9R^{10}$, $-S-C_1$-$C_4$-alkyl, $-OH$, $-NH_2$, $C_3$-$C_7$-cycloalkyl, and $C_3$-$C_{10}$-alkenyl;
(b) $C_1$-$C_6$-alkyl, $C_2$-$C_5$-alkenyl or $C_2$-$C_5$-alkynyl or substituted $C_1$-$C_6$ alkyl, $C_2$-$C_6$ alkenyl or $C_2$-$C_6$ alkynyl with a substituent selected from the group consisting of aryl $C_3$-$C_7$-cycloalkyl, Cl, Br, I, F, $-OR^4$, $CF_3$, $CF_2CF_3$, $-NH_2$, $-NH(C_1$-$C_4$-alkyl), $-N(C_1$-$C_4$-alkyl)$_2$, $-NH-SO_2R^4$, $-COOR^4$, and $-SO_2NHR^9$;
(c) an unsubstituted, monosubstituted or disubstituted heteroaromatic 5 or 6 membered cyclic ring which contains one or two members selected from the group consisting of N, O, S, and wherein the substituents are members selected from the group consisting of $-OH$, $-SH$, $C_1$-$C_4$-alkyl, $C_1$-$C_4$-alkyloxy $-CF_3$, Cl, Br, I, F, or $NO_2$,
(d) $C_3$-$C_7$-cycloalkyl,
(e) perfluoro-$C_1$-$C_4$-alkyl, or
(f) H;

$R^{7a}$ and $R^{7b}$ are independently
(a) H,
(b) $C_1$-$C_6$-alkyl, $C_2$-$C_6$-alkenyl or $C_2$-$C_6$-alkynyl,
(c) Cl, Br, I, or F,
(d) $CF_3$, or
(e) when $R^{7a}$ and $R^{7b}$ are bonded to adjacent carbon atoms, they can be joined to form a phenyl ring;

$R^{8a}$ and $R^{8b}$ are independently
(a) H,
(b) $C_1$-$C_6$-alkyl or substituted $C_1$-$C_6$ alkyl with a substituent selected from the group consisting of $-OH$, -guanidino, $C_1$-$C_4$-alkoxy, $-N(R^4)_2$, $COOR^4$, $-CON(R^4)_2$, $-O-COR^4$, $-aryl$, heteroaryl, $-S(O)_x-R^{23}$, -tetrazol-5-yl, $-CONHSO_2R^{23}$, $-SO_2NH$-heteroaryl, $-SO_2NHCOR^{23}$, $-PO(OR^4)_2$, $-PO(OR^4)R^9$, $-SO_2NH-CN$, $-NR^{10}COOR^{23}$, morpholino, $N-(C_1$-$C_6$-alkyl)piperazine, or $-COR^4$;
(c) $-CO$-aryl,
(d) $-C_3$-$C_7$-cycloalkyl,
(e) $-Cl$, Br, I, or F,
(f) $-OH$,
(g) $-OR^{23}$,
(h) $-C_1$-$C_4$-perfluoroalkyl,
(i) $-S(O)_x-R^{23}$,
(j) $-COOR^4$,
(k) $-SO_3H$,
(l) $-NR^4R^{23}$,
(m) $-NHCOR^{23}$
(n) $-NH-CO_2R^{23}$,
(O) $-SO_2NR^9R^{10}$,
(p) $-NO_2$,
(q) $-NHSO_2R^{23}$,
(r) $-NHCONR^4R^{23}$,

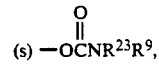

(s) $-\overset{O}{\underset{\|}{O}}CNR^{23}R^9$, (t) aryl or -heteroaryl,
(u) $-NHSO_2CF_3$,
(v) $-SO_2NH$-heteroaryl,
(w) $-SO_2NHCOR^{23}$,
(x) $-CONHSO_2R^{23}$,
(y) $-PO(OR^4)_2$,
(z) $-PO(OR^4)_2$,
(aa) -tetrazol-5-yl,
(bb) $-CONH$(tetrazol-5-yl),
(cc) $-COR^4$,
(dd) $-SO_2NHCN$, (ee) 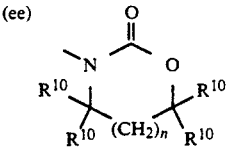

where n = 0 or 1, (ff) $-CO$-heteroaryl, or
(gg) $-NHSO_2NR^{23}R^9$;

$R^9$ is H, $C_1$-$C_5$-alkyl, aryl, or arylmethyl;
$R^{10}$ is H, $C_1$-$C_4$-alkyl;
$R^{11}$ is H, $C_1$-$C_6$-alkyl, $C_1$-$C_4$-alkenyl, $C_1$-$C_4$-alkoxy alkyl, or

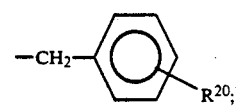

$R^{12}$ is $-CN$, $-NO_2$, $-CF_3$ or $-CO_2R^4$;
$R^{13}$ is H, $(C_1$-$C_4$-alkyl)CO$-$, $C_1$-$C_6$-alkyl, allyl, $C_3$-$C_6$-cycloalkyl, aryl or arylmethyl;
$R^{14}$ is H, $C_1$-$C_8$-alkyl, $C_1$-$C_8$-perfluoroalkyl, $C_3$-$C_6$-cycloalkyl, aryl or arylmethyl;
$R^{15}$ is H, $C_1$-$C_6$-alkyl;
$R^{16}$ is H, $C_1$-$C_6$-alkyl, $C_3$-$C_6$-cycloalkyl, aryl or arylmethyl;

$R^{17}$ is $-NR^9R^{10}$, $-OR^{10}$, $-NHCONH_2$, $-NHCSNH_2$,

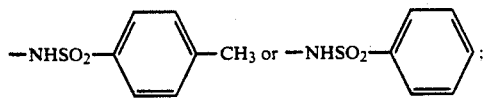

$R^{18}$ and $R^{19}$ are independently $C_1-C_4$-alkyl or taken together are $-(CH_2)_q-$ where q is 2 or 3;

$R^{20}$ is H, $-NO_2$, $-NH_2$, $-OH$ or $-OCH_3$;

$R^{21}$ is H, aryl, $C_1-C_4$-alkyl or $C_1-C_4$-alkyl substituted with a aryl, $-NH_2$, $-NH(C_1-C_4$-alkyl), $-N(C_1-C_4$-alkyl)$_2$, $-CO_2R^4$, $-OH$, $-SO_3H$, or $-SO_2NH_2$ substituent;

$R^{22}$ is
- (a) aryl,
- (b) heteroaryl or,
- (c) $C_1-C_4$-alkyl or $C_1-C_4$alkyl substituted with a substituent selected from the group consisting of aryl, heteroaryl, $-OH$, $-NH_2$, $-NH(C_1-C_4$-alkyl), $-N(C_1-C_4$-alkyl)$_2$, $-CO_2R^4$, Cl, Br, F, I, or $-CF_3$;

$R^{23}$ is
- (a) aryl,
- (b) heteroaryl,
- (c) $C_3-C_7$-cycloalkyl,
- (d) $C_1-C_6$-alkyl or $C_1-C_6$alkyl substituted with a substituent selected from the group consisting of aryl, heteroaryl, $-OH$, $-SH$, $C_1-C_4$-alkyl, $-O(C_1-C_4$-alkyl), $-S(C_1-C_4$-alkyl), $-CF_3$, Cl, Br, F, I, $-NO_2$, $-CO_2H$, $CO_2-C_1-C_4$-alkyl, $-NH_2$, $-NH(C_1-C_4$-alkyl), $-N(C_1-C_4$-alkyl)$_2$, $-PO_3H_2$, $-PO(OH)(O-C_1-C_4$-alkyl), or $-PO(OR^4)R^9$, or
- (e) perfluoro-$C_1-C_4$-alkyl;

X is
- (a) a carbon-carbon single bond,
- (b) $-CO-$,
- (c) $-O-$,
- (d) $-S-$, (e) 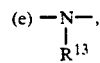

(f) 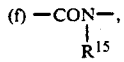

(g) 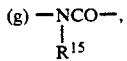

- (h) $-OCH_2-$,
- (i) $-CH_2O-$
- (j) $-SCH_2-$,
- (k) $-CH_2S-$,
- (l) $-NHC(R^9)(R^{10})$,
- (m) $-NR^9SO_2-$,
- (n) $-SO_2NR^9-$,
- (o) $-C(R^9)(R^{10})NH-$,
- (p) $-CH=CH-$,
- (q) $-CF=CF-$,
- (r) $-CH=CF-$,
- (s) $-CF=CH-$,
- (t) $-CH_2CH_2-$,
- (u) $-CF_2CF_2-$, (v) 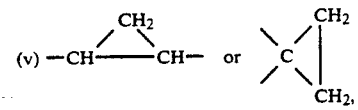

(w) 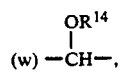

(x) 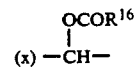

(y) 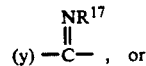, or (z) 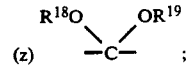;

r is 1 or 2; or a pharmaceutically acceptable salt thereof.

2. A compound of claim 1 wherein:

J is $-C(O)-$;

K and L are connected to form a 6 carbon aromatic ring substituted with $R^{7a}$, $R^{7b}$, $R^{8a}$ and $R^{8b}$;

$R^1$ is
- (a) $-COOH$, (b) 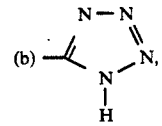

- (c) $-NH-SO_2R^{23}$;
- (d) $-SO_2NH$-heteroaryl,
- (e) $-CH_2SO_2NH$-heteroaryl,
- (f) $-SO_2NH-CO-R^{23}$,
- (g) $-CH_2SO_2NH-CO-R^{23}$,
- (h) $-CONH-SO_2R^{23}$,
- (i) $-CH_2CONH-SO_2R^{23}$,
- (j) $-NHSO_2NHCO-R^{23}$, or
- (k) $-NHCONHSO_2-R^{23}$;

$R^{2a}$ is H;

$R^{2b}$ is H, F, Cl, $CF_3$, $C_1-C_6$-alkyl $C_2-C_4$-alkenyl or $C_2-C_4$-alkynyl;

$R^{3a}$ is H;

$R^{3b}$ is H, F, Cl, $CF_3$, $C_1-C_4$-alkyl, $C_2-C_4$-alkenyl, $C_2-C_4$-alkynyl, $C_5-C_6$-cycloalkyl, $-COOCH_3$, $-COOC_2H_5$, $-SO_2-CH_3$, $NH_2$, $-N(C_1-C_4$-alkyl)$_2$ or $-NH-SO_2CH_3$;

E is a single bond, $-O-$ or $-S-$;

$R^6$ is
- (a) $C_1-C_5$ alkyl or substituted $C_1-C_5$alkyl with a substituent selected from the group consisting of $C_3-C_5$-cycloalkyl, Cl, $CF_3$, $-CCl_3$, $-O-CH_3$, $-OC_2H_5$, $-S-CH_3$, $-S-C_2H_5$, phenyl, or F,
- (b) $C_2-C_5$-alkenyl or $C_2-C_5$-alkynyl, or
- (c) $C_3-C_5$-cycloalkyl;

$R^{7a}$ and $R^{7b}$ are each H;

$R^{8a}$ and $R^{8b}$ are independently
- (a) H,
- (b) $C_1-C_4$-alkyl or substituted $C_1-C_4$-alkyl with an $COOR^4$, $OCOR^{4a}$, OH, or aryl substituent,
- (c) $C_2-C_4$-alkenyl,
- (d) $-OH$,
- (e) $-NO_2$, (f) —NHCOR²³,
(g) —C₁-C₄ alkoxy,
(h) —NHCO₂R²³,
(i) —NR⁴R²³,
(j) Cl, F, or Br,
(k) —CF₃,
(l) —CO₂R₄,
(m) —CO-aryl,
(n) —S(O)ₓ—C₁-C₄-alkyl,
(o) —SO₂—NH—C₁-C₄-alkyl,
(p) —SO₂—NH-aryl,
(q) —NHSO₂CH₃,
(r) aryl, or
(s) —NHCONR⁴R²³;
X is a single bond and;
r is one.

3. A compound of claim 2 wherein:
R¹ is
(a) —COOH,

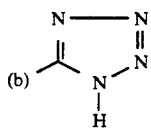

(c) —NH—SO₂—R²³,
(d) —SO₂NH-heteroaryl,
(e) —SO₂NH—CO—R²³, or
(f) —CONH—SO₂R²³;
E is a single bond;
r is one;
R²ᵃ, R²ᵇ, R³ᵃ and R³ᵇ are each H, —C₁-C₆-alkyl, —Cl, —F, —NO₂, or —CF₃;
R⁶ is (C₁-C₄-alkyl), cyclopropyl, —CH₂CH₂CH₂CH₃, —CH₂CH₂CH₃; —C₂-C₅-alkenyl, or -cyclopropylmethyl;
R⁸ᵃ and R⁸ᵇ are each independently H, —C₁-C₄-alkyl, —NO₂, —NR⁴R²³, —O—CH₃, NHCO₂R²³, —Cl, CH₂COOH, —S(O)ₓ—C₁-C₄ alkyl, CH₂O—CO—(C₁-C₄ alkyl), —CO₂R⁴, —F, NHCONR⁴R²³, or —NHCOR²³.

4. A compound of claim 3 wherein:
R¹ is
(a) —COOH,

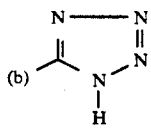

(c) —SO₂—NHCOR²³,
(d) —CONHSO₂R²³, or
(e) —NHSO₂CF₃;
R²ᵃ, R²ᵇ, R³ᵃ and R³ᵇ are each H, —C₁-C₆-alkyl, —Cl, or F;
R⁶ is n-propyl, -ethyl, -n-butyl, -trans-2-butenyl, —CH₂CH₂CF₃, —CH₂CH₂CH₂CF₃; cyclopropyl, or -cyclopropylmethyl; and
R⁸ᵃ and R⁸ᵇ are each independently H, —NO₂, C₁-C₄ alkyl, NH₂, NHCOCH₂, —S(O)ₓ—C₁-C₄ alkyl, —N(CH₃)₂, —OCH₃, —NHCOCH₂NH₂, —NHCOCH₂N(CH)₃)₂, —COOH, —COOCH₃, —CH₂OCOCH₃, Cl, —CH₂COOCH₃, —NHCON(R⁴)₂, —NHCO₂R⁴, —CH₂COOH, —OCH₃, CH₂OH, or NHMe.

5. A compound of claim 4 selected from the group consisting of:
(1) 2-Butyl-1-[(2'-(carboxy)-biphen-4-yl)-methyl]-quinazolin-4(1H)-one;
(2) 2-Butyl-1-[(2'-(tetrazol-5-yl)-biphen-4-yl)-methyl]quinazolin-4(1H)-one;
(3) 2-Propyl-1-[(2'-(tetrazol-5-yl)-biphen-4-yl)-methyl]-quinazolin-4(1H)-one;
(4) 2-Butyl-6-methyl-1-[(2'-(tetrazol-5-yl)-biphen-4-yl)-methyl]quinazolin-4(1H)-one;
(5) 2-Butyl-6-dimethylamino-1-[(2'-(tetrazol-5-yl)-biphen-4-yl)-methyl]quinazolin-4(1H)-one;
(6) 2-Butyl-5-methyl-1-[(2'-(tetrazol-5-yl)-biphen-4-yl)-methyl]quinazolin-4(1H)-one;
(7) 2-Butyl-7-methyl-1-[(2'-(tetrazol-5-yl)-biphen-4-yl)-methyl]quinazolin-4(1H)-one;
(8) 2-Butyl-6-nitro-1-[(2'-(tetrazol-5-yl)-biphen-4-yl)-methyl]quinazolin-4(1H)-one;
(9) 2-Butyl-8-methyl-1-[(2'-(tetrazol-5-yl)-biphen-4-yl)-methyl]quinazolin-4(1H)-one; and
(10) 2-Butyl-5-carboxy-1-[(2'-(tetrazol-5-yl)-biphen-4-yl)-methyl]-5-benzylquinazolin-4(1H)-one.

6. A compound of claim 1 wherein:
K is —C(O)—;
J and L are connected together to form a 6 carbon aromatic ring substituted with R⁷ᵃ, R⁷ᵇ, R⁸ᵃ and R⁸ᵇ;
R¹ is
(a) —COOH,

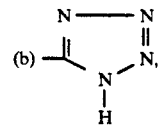

(c) —NH—SO₂R²³,
(d) —SO₂NH-heteroaryl,
(e) —CH₂SO₂NH-heteroaryl,
(f) —SO₂NH—CO—R²³,
(g) —CH₂SO₂NH—CO—R²³,
(h) —CONH—SO₂R²³,
(i) —CH₂CONH—SO₂R²³,
(j) —NHSO₂NHCO—R²³, or
(k) —NHCONHSO₂—R²³;
R²ᵃ is H;
R²ᵇ is H, F, Cl, CF₃, C₁-C₄-alkyl, C₂-C₄-alkenyl, or C₂-C₄-alkynyl;
R³ᵃ is H;
R³ᵇ is H, F, Cl, CF₃, C₁-C₆-alkyl, C₂-C₄-alkenyl, C₂-C₄-alkynyl C₅-C₆-cycloalkyl, —COOCH₃, —COOC₂H₅, —SO₂—CH₃, NH₂, —N(C₁-C₄-alkyl)₂, or —NH—SO₂CH₃;
E is a single bond, —O— or —S—;
R⁶ is
(a) C₁-C₅ alkyl substituted C₁-C₅alkyl with a substituent selected from the group consisting of methyl, ethyl, Cl, CF₃, CCl₃, —O—CH₃, —OC₂H₅, —S—CH₃, —S—C₂H₅, phenyl, or F,
(b) C₂-C₅-alkenyl or C₂-C₅-alkynyl, or
(c) C₃-C₅-cycloalkyl;
R⁷ᵃ and R⁷ᵇ are each H;
R⁸ᵃ and R⁸ᵇ are independently
(a) H,
(b) C₁-C₄-alkyl or substituted C₁-C₄alkyl with COOR⁴, OCOR⁴ᵃ, OH, or aryl substituent,
(c) C₂-C₄-alkenyl, (d) —OH,
(e) —NO$_2$,
(f) —NHCOR$^{23}$,
(g) —C$_1$-C$_4$-alkoxy,
(h) —NHCO$_2$R$^{23}$,
(i) —NR$^4$R$^{23}$,
(j) Cl, F, or Br,
(k) —CF$_3$,
(l) —CO$_2$R$^4$,
(m) —CO-aryl,
(n) —S(O)$_x$—C$_1$-C$_4$-alkyl
(o) —SO$_2$—NH-C$_1$-C$_4$-alkyl,
(p) —SO$_2$—NH—aryl,
(q) —NHSO$_2$CH$_3$,
(r) -aryl, or
(s) NHCONR$^4$R$^{23}$;

X is a single bond or —CO—; and,
r is one.

7. A compound of claim 6 wherein:
R$^1$ is
(a) —COOH,

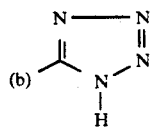

(c) —NH—SO$_2$—R$^{23}$,
(d) —SO$_2$NH—heteroaryl,
(e) —SO$_2$NH—CO—R$^{23}$, or
(f) —CONH—SO$_2$R$^{23}$;

E is a single bond;
r is one;
R$^{2a}$, R$^{2b}$, R$^{3a}$ and R$^{3b}$ are each H, —C$_1$-C$_6$-alkyl, —Cl, —F, —NO$_2$, or —CF$_3$;
R$^6$ is C$_1$-C$_4$-alkyl, cyclopropyl, —CH$_2$CH$_2$CH$_2$CH$_3$, —CH$_2$CH$_2$CF$_3$; —C$_2$-C$_5$-alkenyl, or -cyclopropylmethyl;
R$^{8a}$ and R$^{8b}$ are each independently H, —C$_1$-C$_4$-alkyl, —NO$_2$, —NR$^{10}$R$^{23}$, —OCH$_3$, NHCO$_2$R$^{23}$, —Cl, CH$_2$COOH, —S(O)$_x$—C$_1$-C$_4$-alkyl, CH$_2$OCO—(C$_1$-C$_4$ alkyl), —CO$_2$R$^4$, —F, NHCONR$^4$R$^{23}$, or —NHCOR$^{23}$.

8. A compound of claim 7 wherein:
R$^1$ is
(a) —COOH,

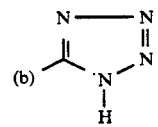

(c) —SO$_2$—NHCOR$^{23}$,
(d) —CONHSO$_2$R$^{23}$, or
(e) —NHSO$_2$CF$_3$;

R$^{2a}$, R$^{2b}$, R$^{3a}$ and R$^{3b}$ are each H, —C$_1$-C$_4$-alkyl, —Cl, or F,
R$^6$ is n-propyl, -ethyl, -n-butyl, -trans-2-butenyl, —CH$_2$CH$_2$CF$_3$, —CH$_2$CH$_2$CH$_2$CF$_3$, cyclopropyl, or -cyclopropylmethyl; and
R$^{8a}$ and R$^{8b}$ are each independently H, —NO$_2$, C$_1$-C$_4$-alkyl, NH$_2$, NHCOCH$_2$, —S(O)$_x$—C$_1$-C$_4$-alkyl, —N(CH$_3$)$_2$, —OCH$_3$, —NHCOCH$_2$NH$_2$, —NHCOCH$_2$N(CH)$_3$)$_2$, —COOH, —COOCH$_3$, —CH$_2$OCOCH$_3$, Cl, —CH$_2$COOCH$_3$, —CH$_2$COOH, —OCH$_3$, —COOMe, CH$_2$OH, NHMe, —NHCON(R$^4$)$_2$ or —NHCO$_2$R$^4$.

9. A compound of claim 8 which is a member of the group consisting of:
(1) 2-Butyl-6-isopropyl-3-[(2'-(tetrazol-5-yl)biphen-4-yl)methyl]quinazolin-4(3H)-one;
(2) 6-Methyl-2-propyl-3-[(2'-(tetrazol-5-yl)biphen-4-yl)methyl]-quinazolin-4(3H)-one;
(3) 2-Butyl-6-(N-isopropylcarbamoyl)amino-3-[(2'-(tetrazol-5-yl)biphen-4-yl)methyl]quinazolin-4(3H)-one;
(4) 2-Butyl-6-carboxy-3-(2'-(tetrazol-5-yl)biphen-4-yl)methylquinazolin-4(3H)-one;
(5) 2-Butyl-5-carboxy-3-(2'-(tetrazol-5-yl)biphen-4-yl)methylquinazolin-4(3H)-one; and
(6) 2-Butyl-5-carbomethoxy-6-methyl-3-(2'-(tetrazol-5-yl)biphen-4-yl)methylquinazolin-4(3H)-one.

10. A compound of claim 1 wherein:
K is —C(=NR$^{22}$)—;
J and L are connected together to form a 6 carbon aromatic ring substituted with R$^{7a}$, R$^{7b}$, R$^{8a}$ and R$^{8b}$;
R$^1$ is
(a) COOH,

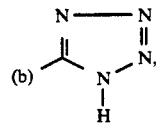

(c) —NH—SO$_2$R$^{23}$,
(d) —SO$_2$NH-heteroaryl,
(e) —CH$_2$SO$_2$NH-heteroaryl,
(f) —SO$_2$NH—CO—R$^{23}$,
(g) —CH$_2$SO$_2$NH—CO—R$^{23}$,
(h) —CONH—SO$_2$R$^{23}$,
(i) —CH$_2$CONH—SO$_2$R$^{23}$,
(j) —NHSO$_2$NHCO—R$^{23}$, or
(k) —NHCONHSO$_2$—R$^{23}$;

R$^{2a}$ is H;
R$^{2b}$ is H, F, Cl, CF$_3$ or C$_1$-C$_6$-alkyl, C$_2$-C$_4$-alkenyl, or C$_2$-C$_4$-alkynyl
R$^{3a}$ is H;
R$^{3b}$ is H, F, Cl, CF$_3$, C$_1$-C$_4$-alkyl, C$_2$-C$_4$-alkenyl, C$_2$-C$_4$-alkynyl; C$_5$-C$_6$-cycloalkyl, —COOCH$_3$, —COOC$_2$H$_5$, —SO$_2$—CH$_3$, NH$_2$, —N(C$_1$-C$_4$-alkyl)$_2$, or —NH—SO$_2$CH$_3$;
E is a single bond, —O— or —S—;
R$^6$ is
(a) C$_1$-C$_5$ alkyl or substituted C$_1$-C$_5$-alkyl with a substituent selected from the group consisting of C$_3$-C$_5$-cycloalkyl, Cl, CF$_3$, CCl$_3$, —O—CH$_3$, —OC$_2$H$_5$, —S—CH$_3$, —S—C$_2$H$_5$ phenyl, or F;
(b) C$_2$-C$_5$-alkenyl or C$_2$-C$_5$-alkynyl, or
(c) C$_3$-C$_5$-cycloalkyl;
R$^{7a}$ and R$^{7b}$ are each H or when R$^{7a}$ and R$^{7b}$ are bonded to adjacent carbon atoms, they can be joined to form a phenyl ring;
R$^{8a}$ and R$^{8b}$ are independently
(a) H,
(b) C$_1$-C$_4$-alkyl or substituted C$_1$-C$_4$-alkyl with an COOR$^4$, OCOR$^{4a}$, OH, or aryl substituent,
(c) C$_2$-C$_4$-alkenyl,
(d) —OH,
(e) —NO$_2$,
(f) —NHCOR$^{23}$, (g) —$C_1$-$C_4$-alkoxy,
(h) —$NHCO_2R^{23}$,
(i) —$NR^4R^{23}$,
(j) Cl, F, or Br,
(k) —$CF_3$,
(l) —$CO_2R^4$,
(m) —CO-aryl,
(n) —$S(O)_x$—$C_1$-$C_4$-alkyl,
(o) —$SO_2$—NH—$C_1$-$C_4$-alkyl,
(p) —$SO_2$—NH-aryl,
(q) —$NHSO_2CH_3$,
(r) aryl, or
(s) —$NHCONR^4R^{23}$;

X is a single bond; and
r is one.

11. A compound of claim 10 wherein:
R$^1$ is
(a) —COOH,

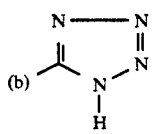

(c) —NH—$SO_2$—$R^{23}$,
(d) —$SO_2$NH—heteroaryl,
(e) —$SO_2$NH—CO—$R^{23}$, or
(f) —CONH—$SO_2R^{23}$;

E is a single bond;
r is one;
$R^{2a}$, $R^{2b}$, $R^{3a}$ and $R^{3b}$ are each H, —$C_1$-$C_6$-alkyl, —Cl, —F, $NO_2$, or $CF_3$;
$R^6$ is $C_1$-$C_4$-alkyl, cyclopropyl, —$CH_2CH_2CH_2CF_3$, —$CH_2CH_2CF_3$, —$C_2$-$C_5$-alkenyl; or -cyclopropylmethyl; and
$R^{8a}$ and $R^{8b}$ are each independently H, —$C_1$-$C_4$-alkyl, —$NO_2$, $NR^{10}R^{23}$, —O—$CH_3$, —Cl, $CH_2COOH$, —$S(O)_x$—$C_1$-$C_4$-alkyl, $CH_2O$—CO—($C_1$-$C_4$-alkyl), $NHCOR^{23}$, —$CO_2R^4$, $NHCO_2R^{23}$ or $NHCOR^4R^{23}$.

12. A compound of claim 11 wherein:
R$^1$ is
(a) —COOH,

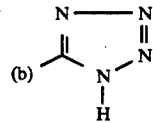

(c) —$SO_2$—$NHCOR^{23}$,
(d) —$CONHSO_2R^{23}$, or
(e) —$NHSO_2CF_3$;
$R^{2a}$, $R^{2b}$, $R^{3a}$ and $R^{3b}$ are each H, —$C_1$-$C_4$-alkyl, —Cl, or F;
$R^6$ is n-propyl, -ethyl, -n-butyl, -trans-2-butenyl, —$CH_2CH_2CF_3$, —$CH_2CH_2CH_2CF_3$, cyclopropyl, or -cyclopropylmethyl;
$R^{8a}$ and $R^{8b}$ are each independently H, —$NO_2$, $C_1$-$C_4$-alkyl, $NH_2$, $NHCOCH_2$, —$S(O)_x$—$C_1$-$C_4$-alkyl, —$N(CH_3)_2$, —$OCH_3$, —$NHCOCH_2NH_2$, —$NHCOCH_2N(CH)_3)_2$, —COOH, —$COOCH_3$, —$CH_2OCOCH_3$, Cl, —$CH_2COOCH_3$, —COOH, —$CH_2COOH$, —$OCH_3$, $CH_2OH$, NHMe, —$NHCON(R^4)_2$ or —$NHCO_2R^4$.

13. A pharmaceutical composition useful in the treatment of hypertension which comprises a pharmaceutically acceptable carrier and a pharmaceutically effective amount of a compound of claim 1.

14. An ophthalmological formulation for the treatment of ocular hypertension comprising an ophthalmologically acceptable carrier and an effective ocular antihypertensive amount of a compound of claim 1.

* * * * *